(12) United States Patent
Tajima

(10) Patent No.: US 8,057,760 B2
(45) Date of Patent: Nov. 15, 2011

(54) REACTION VESSEL, REACTION VESSEL LIQUID INTRODUCING DEVICE, LIQUID INTRODUCING AND REACTION MEASURING DEVICE, AND LIQUID INTRODUCING DEVICE

(75) Inventor: Hideji Tajima, Chiba (JP)

(73) Assignee: Universal Bio Research Co., Ltd, Matsudo-shi, Chiba (JP)

( * ) Notice: Subject to any disclaimer, the term of this patent is extended or adjusted under 35 U.S.C. 154(b) by 0 days.

(21) Appl. No.: 12/776,030

(22) Filed: May 7, 2010

(65) Prior Publication Data

US 2010/0279303 A1    Nov. 4, 2010

Related U.S. Application Data

(62) Division of application No. 11/573,110, filed as application No. PCT/JP2005/014305 on Aug. 4, 2005, now Pat. No. 7,727,480.

(30) Foreign Application Priority Data

Aug. 5, 2004 (JP) ................................. 2004-229952

(51) Int. Cl.
*G01N 21/00* (2006.01)
*C12M 1/00* (2006.01)

(52) U.S. Cl. ......... 422/547; 422/50; 422/417; 422/68.1; 422/82.05; 422/559; 436/164

(58) Field of Classification Search .................. 422/102, 422/68.1, 82.05, 100, 101, 50, 502, 547, 422/548, 559, 417; 436/164
See application file for complete search history.

(56) References Cited

U.S. PATENT DOCUMENTS

| 5,639,428 | A | 6/1997 | Cottingham |
| 6,565,815 | B1 | 5/2003 | Chang et al. |
| 6,660,228 | B1 * | 12/2003 | Chang et al. ................. 422/68.1 |
| 2003/0162285 | A1 | 8/2003 | Tajima |

FOREIGN PATENT DOCUMENTS

JP      08-062225      3/1996
(Continued)

OTHER PUBLICATIONS

International Search Report mailed Dec. 6, 2005 by the Japanese Patent Office in connection with International Application No. PCT/JP2005/014305, 4 pages.

Written Opinion mailed Dec. 6, 2005 by the Japanese Patent Office in connection with International Application No. PCT/JP2005/014305, 5 pages.

(Continued)

*Primary Examiner* — Robert J Hill, Jr.
*Assistant Examiner* — Dwan A Gerido
(74) *Attorney, Agent, or Firm* — Haynes and Boone, LLP

(57) ABSTRACT

The invention relates to a reaction vessel, a reaction vessel liquid introducing device, a liquid introducing and reaction measuring device, and a liquid introducing device, and is directed to being able to perform temperature control of a liquid stored within the reaction vessel with a high accuracy and faithful responsiveness. The reaction vessel comprises: a storage chamber in which a liquid is storable, that has an opening part; a reaction chamber that is formed thinner or narrower than the storage chamber; and at least one flow passage that communicates between the storage chamber or the exterior and the reaction chamber. The reaction vessel is formed such that it is connectable to a liquid introducing section provided externally, and the liquid can be introduced into the reaction chamber by connecting to the liquid introducing section.

12 Claims, 21 Drawing Sheets

FOREIGN PATENT DOCUMENTS

| | | |
|---|---|---|
| JP | 2622327 | 6/1997 |
| JP | 09-262084 | 10/1997 |
| JP | 2000-511435 | 9/2000 |
| JP | 2002-010777 | 1/2002 |
| JP | 2003-500674 | 1/2003 |
| JP | 2003-502656 | 1/2003 |

OTHER PUBLICATIONS

International Preliminary Report on Patentability mailed Sep. 19, 2006 by the Japanese Patent Office in connection with International Application No. PCT/JP2005/014305, 5 pages.

Dwan A. Gerido, Office Action issued on Aug. 11, 2009 in U.S. Appl. No. 11/573,110, U.S. Patent Office, 5 pages.

Dwan A. Gerido, Notice of Allowance, Notice of Allowability, Interview Summary and Examiner's Amendment issued on Jan. 19, 2010 in U.S. Appl. No. 11/573,110, U.S. Patent Office, 10 pages.

Dwan A. Gerido, Notice of Allowance, Notice of Allowability, Interview Summary and Examiner's Amendment issued on Sep. 28, 2010 in U.S. Appl. No. 12/776,085, U.S. Patent Office, 9 pages.

Dwan A. Gerido, Notice of Allowance, Notice of Allowability and Examiner's Amendment issued on Sep. 28, 2010 in U.S. Appl. No. 12/776,131, U.S. Patent Office, 6 pages.

* cited by examiner

REACTION VESSEL, REACTION VESSEL LIQUID INTRODUCING DEVICE, LIQUID INTRODUCING AND REACTION MEASURING DEVICE, AND LIQUID INTRODUCING DEVICE

CROSS REFERENCE

This application is a division of U.S. patent application Ser. No. 11/573,110, filed Aug. 15, 2007, now U.S. Pat. No. 7,727,480, issued Jun. 1, 2010, which is a United States national phase filing of international application no. PCT/JP2005/014305, filed Aug. 4, 2005, which claims priority to Japanese patent application no. 2004-229952, filed Aug. 5, 2004, the disclosures of which are incorporated herein by reference.

TECHNICAL FIELD

The present invention relates to a reaction vessel, a reaction vessel liquid introducing device, a liquid introducing and reaction measuring device, and a liquid introducing device.

BACKGROUND ART

In recent years, the polymerase chain reaction (PCR) method is used in all biology related fields as a DNA amplification method that quickly and easily amplifies specific DNA fragments. The PCR method is a method that designs two primers that are complementary to the template DNA, and reproduces the area between the primers thereof within a test tube (in vitro). The method obtains the PCR products by exponentially amplifying the DNA by repeating temperature cycles wherein a reaction solution containing complementary DNA, primers, nucleotides, and thermostable DNA polymerase is incubated at various temperatures.

A single cycle comprises, with respect to a vessel charged with complementary DNA, the primer, DNA polymerase, nucleotides, and a reaction buffer solution; denaturation of the double stranded DNA into a single strand, annealing of the primer to the single stranded DNA, and incubation at the respective temperature conditions at which a DNA strand that is complementary to the single strand is synthesized, and a single molecule DNA fragment is made into two molecules. In the next cycle, since the DNA fragments synthesized in the previous cycle also become templates, the DNA fragments synthesized after n cycles becomes 2n molecules.

Conventionally, in regard to temperature control, the next heating or cooling of the temperature is performed by accommodating the vessel, which is formed by glass, or the like, charged with complementary DNA, the primer, DNA polymerase, nucleotides and the reaction buffer solution, within a block-shaped housing section of a constant temperature device formed by a material of aluminum, or the like, and heating or cooling the metallic block-shaped housing section and waiting until the liquid temperature becomes a uniform temperature distribution (Patent Document 1).

Consequently, until the reaction liquid within the vessel is heated or cooled, as well as a long time being taken to reach a uniform temperature distribution in the liquid temperature due to the large capacity of the vessel, complex temperature changes occur as a result of the differences in the heat capacity or the specific heat of the housing section and the vessel, and there is a problem in that complex temperature instructions need to be performed in order to perform DNA amplification at a high accuracy.

Incidentally, in the PCR method, temperature control is important, and by changing the temperature cycles, the quality and quantity of the finally obtained PCR products can be changed.

In particular, in real time PCR, a more accurate quantification is performed by detecting and analyzing the generation process of the amplification product of PCR in real time, and a more accurate and quick temperature control is necessary. Consequently, a variety of devices have been proposed (Patent Document 2 to Patent Document 5). However, these apparatuses are large-scale and complex devices in that they are provided with complex flow passages, or used large-scale centrifugal devices, and the like.

On the other hand, the present inventor has disclosed a reaction vessel having a reaction vessel body which is furnished with a reaction chamber that stores the reaction liquid, and a cap member that seals an opening part of the reaction chamber, and in addition a pressing section wherein the cap member presses the reaction liquid, and this has made it possible to perform quick temperature control on a simple device scale without the need for centrifugal force (Patent Document 6).

However, the present inventor, by combining the thinning or capillaration of a liquid of high thermal efficiency, and a reasonable centrifugal process based on the particular shape of the vessel thereof, has reached the idea of performing and obtaining a simultaneous shortening and automation of a consistent process in regard to PCR, and the like, without using a large-scale device.

[Patent Document 1] Publication of Japanese Patent No. 2622327
[Patent Document 2] Japanese Translation of PCT International Application, Publication No. 2000-511435
[Patent Document 3] Japanese Translation of PCT International Application, Publication No. 2003-500674
[Patent Document 4] Japanese Translation of PCT International Application, Publication No. 2003-502656
[Patent Document 5] U.S. Pat. No. 5,958,349
[Patent Document 6] Japanese Unexamined Patent Application, Publication No. 2002-10777

DISCLOSURE OF INVENTION

Problems to be Solved by the Invention

Accordingly, the present invention has been achieved in order to solve the problems mentioned above, and a first object thereof is in providing a reaction vessel, a reaction vessel liquid introducing device, a liquid introducing and reaction measuring device, and a liquid introducing device wherein temperature control of a liquid stored within the vessel can be performed with a high accuracy and faithful responsiveness.

A second object is in providing a reaction vessel, a reaction vessel liquid introducing device, a liquid introducing and reaction measuring device, and a liquid introducing device in which the process can be quickly performed by shortening the time from when a heating or cooling instruction is given until the liquid temperature is uniformly distributed.

A third object is in providing a reaction vessel, a reaction vessel liquid introducing device, a liquid introducing and reaction measuring device, and a liquid introducing device in which a homogeneous reaction and highly accurate optical information is obtained as a result of thinning or capillaration of the liquid in a state where bubbles and gas regions have been removed from within the liquid.

A fourth object is in providing a reaction vessel, a reaction vessel liquid introducing device, a liquid introducing and reaction measuring device, and a liquid introducing device in which consistent processing can be efficiently and automatically performed in regard to the liquid, which is the processing subject.

Means for Solving the Problem

A first aspect of the invention is a reaction vessel being a vessel that has: a storage chamber in which a liquid is storable, that has an opening part; a reaction chamber that is formed thinner or narrower than the storage chamber; and at least one flow passage that communicates between the storage chamber or the exterior and the reaction chamber, and the vessel is formed such that it is connectable to a liquid introducing section provided externally, and the liquid can be introduced into the reaction chamber by connecting to the liquid introducing section.

Here, the "storage chamber" is a portion in which the liquid is storable, and is provided to simplify the introduction of the liquid into the reaction chamber. The introduction of the liquid into the storage chamber is performed from the opening part, or through the flow passage.

The size or the thickness of the storage chamber is a size or a thickness at which the introduction of the liquid from the opening part to the storage chamber can basically be easily performed by gravity alone, or a size or a thickness in which it is possible to install a rotating body on the opening part.

The "reaction chamber" is a thinness (narrowness) level at which the introduction of the liquid is not easily performed by gravity alone in a state where the contamination of gas has been eliminated. The thickness or the width of the reaction chamber is, for example, 0.1 millimeters to 3 millimeters. Accompanying this, the handled liquid quantity corresponds to, for example, a few μliters to 300 μliters. According to this quantity, the processing time of the PCR method corresponds to approximately several minutes to several tens of minutes. For example, for the shape of the reaction chamber, the size of the largest side face is, for instance, a square shape with a length and width of 5 mm or 3 mm, or a circular shape with a radius of 5 mm or 3 mm, and a thickness of approximately 1 mm, and accordingly, in the case of a square shape, the capacity thereof is 25 μliters or 9 μliters.

The "flow passage" is a portion that communicates the interval between the storage chamber or the exterior and the reaction chamber, and is a portion at which passage of liquid is exclusively performed. For example, it is a portion that is formed narrower or thinner compared to the storage chamber, or, for example, at the interval between a thinned reaction chamber, the width thereof is narrowly formed, or, at the interval between a capillarated reaction chamber, for example, it is a portion having a different thickness to the reaction chamber. As a result of communication using a flow passage, the introduction of the liquid can be performed with certainty, the vessel is compactly formed or the sealing of the reaction chamber is simplified, and it is easy to position the reaction chamber farther away from the rotation axis than the storage chamber. In order to introduce the liquid into the reaction chamber in a state where the contamination of gas has been eliminated, for example, this is performed by utilizing a centrifugal force or a suction force.

The reason for providing the "reaction chamber" is for improving the efficiency of the heating process such that by introducing the liquid into the reaction chamber, in regard to the liquid, at the very least, the heat transmission time in the thickness direction thereof is shortened, heat or temperature is transferred to the liquid in a short time, and a temperature distribution such that the liquid temperature promptly becomes uniform can be achieved. Accordingly, the heating or the cooling can be performed by bringing a solid or a liquid heating and cooling medium into contact with, or close to, the reaction chamber, or by ventilating hot air or cold air by means of a dryer. Furthermore, the reaction chamber is heated or cooled by means of the heating and cooling medium, for example, by mounting in the wall with the largest area amongst the walls that enclose the reaction chamber, or by sandwiching from both sides with respect to the wall along the normal direction of the wall with the largest area. In a case where a target material, and the like, has been labeled with a fluorescent material, in order to obtain the optical information resulting from the fluorescence thereof, for example, this large wall is irradiated with an excitation light, and light is received from the same large wall, or from a small wall.

The "vessel" has a portion (here, it is the storage chamber) in which the liquid is storable, and as long it has something of the manner thereof, it may be a dispensing tip form having, in addition to one opening part, a liquid suction and discharge part. Since the vessel has an opening part in the storage chamber, in order to achieve the function as a vessel, there is a need for it to be connected such that liquid does not come out from the opening part to the outside, even in a case where the liquid introducing section is a rotating body and the vessel is connected to the rotating body. That is to say, the opening part is not connectingly installed facing downwards or facing sideways without being blocked by a rotating body or another lid member thereof. Accordingly, in a case where the opening part is not blocked by a cap or the like, there is a need for the opening part to be open facing upwards when it is used as a vessel or when it is connected to a rotating body such that the liquid is storable, and in regard to when it is installed on the rotating body of the vessel, the direction in which the opening part thereof is open and the rotation axis of the rotating body thereof become parallel in the vertical direction. A cap that blocks the opening part may be provided on the opening part.

In regard to the vessel, in a case where it has a reaction chamber that has only one opening or that is communicated with one flow passage, it is denoted as a fluid storage section, and in a case where it has a reaction chamber that has two or more openings or that is communicated with two or more flow passages, it is denoted as a fluid circuit. The dispensing tip form vessel or a number of the vessels disclosed in the embodiments mentioned below correspond to fluid circuits. In the case of a fluid circuit, the introduction of the liquid is performed from a portion of the openings or the flow passages provided on the reaction chamber, and by discharging gas from the other openings or flow passages, the introduction of the liquid can efficiently and smoothly performed. Furthermore, since contamination by gas or bubbles in the liquid introduced to the housing chamber can be even more certainly prevented, it becomes possible to perform uniform and highly accurate temperature control and measure accurate optical information with respect to the liquid within the reaction chamber. Hence, a portion of the openings or the flow passages of the reaction chamber are necessarily communicated with the storage chamber.

The "liquid introducing section" introduces the liquid from the storage chamber to the reaction chamber, or from the exterior to the reaction chamber, or when the liquid is moved from the storage chamber through the reaction chamber to the exterior, or from the exterior through the reaction chamber to the storage chamber, it is a section that has a function of introducing the liquid to the reaction chamber, and it is provided such that it can be connected to the vessel. For the introduction of the liquid, for example, a rotation mechanism of the vessel that introduces to the reaction chamber by means of applying centrifugal force to the liquid, or a nozzle provided with a suction and discharge mechanism that introduces to the reaction chamber by means of suction of the liquid, is used.

The "connection" includes installation, engagement, engaging insertion, engaging attachment, engaging fitting, linking, threading, close contact, or adhesion of the reaction vessel to the liquid introducing section, or accommodation or installation of the entire reaction vessel in the liquid introducing section, or other installation, contact, and accommodation methods of the same level as these that take into consideration the gist of the invention. In regard to the rotating body, there is a case where it is connected at the upper side of the reaction vessel, and a case where it is connected at the lower side of the reaction vessel. Since it "has one flow passage", it is necessary for the reaction chamber to have at least one opening that introduces or discharges liquid or gas.

According to the reaction vessel of the first aspect of the invention, the liquid can be easily thinned and capillarated by introducing the liquid from the storage chamber to the reaction chamber. By using this reaction vessel, temperature control of the liquid can be performed with a high accuracy and a faithful responsiveness.

By thinning or capillarating the liquid by means of the reaction vessel or the reaction vessel liquid introducing device, the time from giving the instruction for heating or cooling with respect to the liquid until the liquid temperature becomes a uniform temperature distribution is shortened, and the process can be quickly and efficiently performed.

According to the reaction vessel or the reaction vessel liquid introducing device, by utilizing centrifugal force, and the like, thinning or capillaration can be performed in a state where contamination by bubbles or gas has been removed from within the liquid. Accordingly, at the time of temperature control, a homogeneous temperature distribution is obtained, and furthermore, highly accurate optical information can be measured.

Moreover, according to the reaction vessel, it is communicated by providing one flow passage between the storage chamber or the exterior and the reaction chamber. As a result, the interval between the reaction chamber and the storage chamber can be separated in terms of distance. Accordingly, for the reaction vessel liquid introducing device, which is based on centrifugal force, a large centrifugal force can be applied to the liquid that is to be introduced. Furthermore, for the reaction vessel liquid introducing device, which is based on suction and discharge forces, by communicating the interval between the exterior and the reaction chamber through a narrow flow passage, it becomes possible to insert the end section of the flow passage into various vessels. Moreover, it becomes easier to suction and easier to handle even a small quantity of liquid. Furthermore, by blocking the flow passage, it becomes easier to make the reaction chamber sealable.

Moreover, according to the reaction vessel, a storage chamber is provided for the reaction vessel, and by making the liquid temporarily storable in the storage chamber, the introduction of the liquid into the reaction chamber can be simplified.

Furthermore, by detachably providing the reaction vessel with respect to the liquid introducing section such as a rotating body provided to the exterior, the reaction vessel can be disposably formed, and hence the process can be inexpensively performed.

A second aspect of the invention is a reaction vessel wherein at least a portion of the reaction chamber has a translucence or a semi-translucence.

Here, the reason for making "a reaction chamber in which a portion is translucent or semi-translucent" is in order to obtain the optical information within the reaction chamber, and, for example, it is for measuring the quantity or concentration of genetic material, such as DNA, which has been labeled with fluorescence, and the like, by real time PCR.

Here, "real time PCR" refers to a method of performing PCR while measuring the amplification quantity of DNA in real time. In real time PCR, electrophoresis is unnecessary, and this has the advantage in that the amplification is observable during the temperature cycles, and quantitative results are obtained. Methods that use normal fluorescent test reagents include the cycling probe method, the intercalator method, the Taqman probe method, and the Molecular Beacon method.

According to the second aspect of the invention, since at least a portion of the reaction chamber has translucence or semi-translucence, then in regard to real time PCR, and the like, the optical information within the reaction chamber can be easily obtained. In a case where the reaction chamber is not translucent or semi-translucent, the optical information can be obtained by providing an optical waveguide within the reaction chamber.

A third aspect of the invention is a reaction vessel wherein the opening part has a cap that is connectable to the opening part such that it is detachable.

Here, the cap is one that is able to seal the opening part, and the opening part and the cap are connected by, for example, installation and contact methods, such as installation, engagement, threading, engaging fitting, engaging insertion, linking, close contact, and adhesion. Furthermore, the cap, for example, may be installably provided between the lower end section of the rotating body of the liquid introducing section by means of installation, and the like. Consequently, the leaking of liquid or gas from the opening part can be prevented.

According to the third aspect of the invention, by providing a cap that is connectable to the opening part such that it is detachable, the leaking of the liquid that is stored in the storage chamber, from the opening part to the exterior can be prevented. Furthermore, in a case where the liquid introducing section can be connected to the cap such that it is detachable, the contact between the liquid and the liquid introducing section can also be prevented.

In particular, in a case where the liquid introducing section is the rotating body, if a cap is provided on the lower end section of the rotating body such that it is detachable, and such that it covers the same, and the opening part of the vessel is made to be connected through the cap, in a case where high-speed rotation of the rotating body is performed, cross-contamination from splashing of the liquid and the rotating body directly coming into contact with the liquid within the vessel is avoided with certainty. Furthermore, by preventing the splashing of the liquid to the upper part, the liquid is pushed back to the lower side, and a more efficient introduction of the liquid into the reaction chamber can be achieved.

A fourth aspect of the invention is a reaction vessel wherein the flow passage and the reaction chamber are formed by a tabular frame having grooves or holes, and a film of a soft material that covers the frame from one side or from both sides. Here, the "film" includes laminates.

According to the fourth aspect of the invention, by forming the tabular frame, which has grooves or holes, by a film of a soft material that covers it from one side or from both sides, even if the reaction vessel is a complex construction, a reaction vessel having a sealable reaction chamber can be easily and inexpensively produced.

A fifth aspect of the invention is a reaction vessel wherein the flow passage is one that communicates between the reaction chamber and the storage chamber, the liquid introducing section is a rotatable rotating body, and the reaction vessel is connectable to the rotating body, and at the time of connection, a rotation axis of the rotating body passes through the vessel, the reaction chamber is formed such that it is positioned farther away from the rotation axis than the storage chamber, and is rotatable together with the rotating body.

Since "at the time the reaction vessel is connected to the rotating body, the rotation axis of the rotating body passes through the vessel, and the reaction chamber is formed such that it is positioned farther away from the rotation axis than the storage chamber", the vessel is rotatable about its own axis by means of the rotating body. The "rotation axis" is different to a specific rotation axle, and denotes an abstract central line of rotation.

The "object rotates about its own axis" refers to the object rotating about a rotation axis that passes through the object, and it is a concept that contrasts revolution, in which an object rotates about a rotation axis provided to the exterior of the object thereof. The liquid stored in the storage chamber, as a result of the high-speed rotation of the rotating body, moves to the reaction chamber that is connected at a position farther away than the storage chamber with respect to the rotation axis as a result of a centrifugal force, and since gas has a smaller specific gravity than liquid, it moves in a direction closer to the axis than the liquid, and the liquid can be introduced into the reaction chamber in a state where it is not contaminated by gas. Furthermore, if the reaction chamber is placed on the underside of the storage chamber, gravity can also be used. Therefore, the introduction of the liquid into the reaction chamber can be made even easier. Here, "high-speed rotation" represents, for example, several hundred rpm to several thousand rpm.

Furthermore, since "the reaction chamber is positioned farther away from the rotation axis than the storage chamber", for example, as shown in FIG. 1, there is a case in which it comprises a storage chamber having an opening part, and a reaction chamber that is communicated with the storage chamber and is formed in a layer form that is thinner than the storage chamber, or, there is a case in which it comprises a narrow tubular or thin layer form reaction chamber that extends diagonally downwards from the lower side of the fat tubular storage chamber, which has an opening part on the upper side. In regard to "positioned farther", for example, the one with the longer distance between the rotation axis and the center of gravity or the center of the portions that are the subject, is determined as the farther object.

Since the "vessel is connectable to a rotatable body", the vessel has a portion that is connectable on the rotating body, that is to say, a connection section. The connection section is, for example, the opening part or another portion of the vessel, or there are cases where it is the whole vessel. Since such a connection section itself is a portion of the vessel or the whole vessel, as a result, the rotation axis passes through the vessel. "Connection" includes, in regard to a portion of the vessel or the whole vessel, installation, engagement, threading, engaging fitting, engaging attachment, engaging insertion, or accommodation of the whole vessel, or other installation methods. There are cases where the rotating body is connected on the upper side of the reaction vessel, and cases where it is connected on the lower side of the reaction vessel. The connection of the reaction vessel to the liquid introducing section may be performed through the cap.

Here, in a case where the opening part and the rotating body are connected by engagement or threading, there is a need for the connection portion of the opening part and the rotating body thereof to match. For example, for a cylinder, there is a need to have a cylindrical inner surface. Furthermore, in a case where the opening part and the rotating body are installed by threading, the rotation direction resulting from the rotating body is the direction in which the rotating body moves forward with respect to the opening part as a result of threading. In this case, as a result, the axis of the opening part and the rotation axis coincide.

Furthermore, for example, if a rotation supporting axle that protrudes out on the lower side of the vessel is provided along the rotation axis, a stable rotation, in which the rotation axis does not deviate, can be applied.

According to the present invention, since the reaction vessel is rotatable about its own axis, the device scale can be reduced without the need to apply a centrifugal force by means of a large centrifugal device. Furthermore, by utilizing a rotatable nozzle mentioned below, processing using the vessel can be consistently automated.

According to the fifth aspect of the invention, the flow passage is provided such that it communicates the interval between the reaction chamber and the storage chamber, and as the liquid introducing section, a rotatable rotating body is provided, the rotation axis of the rotating body passes through the vessel, and the reaction chamber is formed such that it is positioned farther away from the rotation axis than the storage chamber. That is to say, the reaction vessel rotates on its own axis by means of the rotation of the rotating body connected to the reaction vessel, and as a result of this rotation about its own axis, centrifugal force is applied to the liquid, and as a result of centrifugal separation, liquid or solid suspended in the liquid can be introduced with certainty into the reaction chamber in a state where gas and bubbles have been removed. Furthermore, since the liquid is introduced by means of the reaction vessel rotating about its own axis, the liquid can be introduced with certainty without taking up space.

That is to say, since the liquid can be introduced into the reaction chamber by the rotation of the vessel, a large space in which the reaction vessel is revolved around a rotation axis that passes only through the exterior thereof, is unnecessary, and the introduction of the liquid can be achieved by utilizing a small-scale rotation device of basically the size of one vessel.

In a case where the rotation axis of the rotating body is connected to the opening part such that it passes through the opening part of the storage chamber, since the opening part used originally for the introduction of liquid is also used for the installation of the rotating body, there is no need to provide a new rotating body installation section in the vessel, and the structure is simplified.

Furthermore, it is possible to more certainly and easily connect between the rotating body and the reaction vessel by threading or engagement, and particularly in a case where the rotating body is installed by threading, since the rotation of the rotating body can be utilized, it is efficient.

A sixth aspect of the invention is a reaction vessel wherein the rotating body is a rotatable nozzle in which suction and discharge of gas is possible, and the nozzle has a rotation axis along an axial direction thereof.

It is preferable for the "nozzle" to be formed such that it is connectable with not only the vessel, but also with a dispensing tip. Since through a dispensing tip, the dispensing and transport of the liquid, and the like, can also be performed, processing with further diversity can be performed. Furthermore, the nozzle is provided for a dispensing device provided with a suction and discharge device, which performs suction and discharging of the liquid through the nozzle, and it is preferable to make vertical movement and horizontal movement possible by means of technology apparent to those skilled in the art. Consequently, the liquid stored in a vessel provided on the exterior is transportable to a separate vessel.

According to the sixth aspect of the invention, a nozzle that is rotatable on its own axis is used as the rotating body. Consequently, in addition to the thinning or the capillaration of the liquid resulting from the introduction of the liquid into the reaction chamber, it can be utilized for the dispensing of the liquid into the reaction vessel, and it can be applied to a variety of processes. Furthermore, since the rotation axis matches the axis of the nozzle, the rotation radius is small, and the device scale can be restricted.

A seventh aspect of the invention is a reaction vessel wherein; the flow passage comprises a liquid introduction flow passage for introducing the liquid from the storage chamber to the reaction chamber, and a discharge flow passage for discharging gas from the reaction chamber, the liquid introducing section comprises a rotatable rotating body, and the reaction vessel is connectable to the rotating body, and at the time it has been connected, it is formed such that the reaction chamber is positioned farther away from the rotation axis than the storage chamber, and it is rotatable together with the rotating body.

Here, since two flow passages are provided for the reaction chamber, the reaction chamber has two openings which introduce or discharge liquid or gas. Here, the reason for providing the two flow passages of the liquid introduction flow passage and the discharge flow passage is to introduce the liquid into the reaction chamber in a state where it is not contaminated by gas, and to certainly and efficiently remove the gas. In regard to the gas to be discharged by the discharge flow passage, there is a case where it is returned to the storage chamber, and a case where it is discharged to the exterior. Consequently, it is possible to quickly and smoothly perform the introduction of the liquid, and the discharging of the gas.

Furthermore, in regard to the rotation axis of this rotating body, a case where it passes through the vessel, and a case where it does not pass through the vessel, is possible. In the case where it passes through the vessel, it rotates about its own axis, but in the case where it does not pass through, the reaction vessel revolves about the rotation axis.

As a result of the liquid introduction flow passage being formed such that it is positioned farther away from the rotation axis for the case where the rotating body has been connected, than the discharge flow passage, discharging can be smoothly performed since the effect of the centrifugal force on the discharge flow passage is smaller than on the liquid introduction flow passage. In this case, if at least a portion of the discharge flow passage is provided along the rotation axis for the case where the rotating body is connected, the effect of the centrifugal force on the discharge flow passage can be made even smaller. "Connection" has been already explained, and therefore, description is omitted.

The reaction chamber is, for example, formed in an approximate cylindrical shape, and the side face of the reaction chamber has a smaller area than both bottom faces, and it is formed thinner than the storage chamber.

According to the seventh aspect of the invention, by providing a liquid introduction flow passage for introducing the liquid from the storage chamber to the reaction chamber, and a discharge flow passage for discharging gas from the reaction chamber, and using the liquid introducing section as a rotating body, the introduction of the liquid and the discharging of gas are performed using separate flow passages. Therefore the introduction of the liquid and the discharging of gas can be efficiently and quickly performed.

An eighth aspect of the invention is a reaction vessel wherein a deformable soft material is provided for at least a portion of the flow passage or the reaction chamber, and the reaction chamber is sealable by deforming the soft material.

Here, the "soft material" is a material formed from a soft material that is deformable by applying a pressing force, ultrasonic waves, high frequency waves, vibrations, laser, heat, and the like. The soft material is a material that has been formed from, for example, elastic bodies such as rubber, or plastics such as polyethylene or silicone. The soft material includes, for example, the film material that encloses the flow passages or the reaction chamber, or the block shaped material mentioned below that is provided for the flow passage or the reaction chamber.

The deformation of the soft material is, for example, performed by pressing the wall section of the reaction chamber of the flow passages that have been formed by the soft material, or applying ultrasonic waves, high frequency waves, laser, heat, and the like to weld the soft material. In a case where the soft material is formed by an elastic body such as rubber, and it has been deformed by a pressing force, there is a need to maintain the pressing force from the exterior to the elastic body in order to maintain the deformation.

According to the eighth aspect of the invention, a deformable soft material is provided for at least a portion of the flow passage or the reaction chamber, the reaction chamber is sealable by deforming the soft material, and a thinned or capillarated liquid that is not contaminated by gas is easily obtained. Consequently, the discharging of the introduced liquid from within the reaction chamber is prevented, and an efficient and quick introduction of the liquid can be performed.

A ninth aspect of the invention is a reaction vessel wherein the soft material is an elastic block material that is deformable by means of a pressing force, and the interior has a void through which passage of liquid and gas is possible.

Here, the "void" includes pierced holes. As a material that is an "elastic block material" and that has a void in its interior, for example, the elastic valve mentioned below can be given. In order to seal the reaction chamber, there is a need to continuously apply a pressing force to the elastic block material.

According to the ninth aspect of the invention, an elastic block material that is deformable by means of a pressing force and that has a void through which passage of liquid, and the like, is possible, is provided for the flow passage or the reaction chamber, and by applying a pressing force, the liquid can be certainly and easily sealed in the reaction chamber. Furthermore, as a result of this, discharging of the introduced liquid from within the reaction chamber is prevented, and an efficient and quick introduction of the liquid can be achieved.

A tenth aspect of the invention is a reaction vessel comprising, at the time where the reaction vessel is connected to the rotating body, a rotation supporting axle along the rotation axis of the rotating body.

The "rotation supporting axle" is an axle that has been provided such that, accompanying the rotation of the rotating body, smooth rotation of the reaction vessel is made possible. In regard to the rotation supporting axle, for example, in a case such as where the reaction vessel is connected to the rotating body at the opening part of the storage chamber, it is provided such that it protrudes out to the lower part of the reaction vessel, or it may be provided such that the rotation supporting axle that protrudes out to the lower part is made to also protrude out to the upper part, such that the upper end of the rotation supporting axis connects to the rotating body. The rotation supporting axle is also a portion of the reaction vessel. Hence in this case, the rotation axis of the rotating body passes through the vessel, and it corresponds to rotation about its own axis.

According to the tenth aspect of the invention, in a case where the rotation axis of the rotating body passes through the vessel at the time the reaction vessel is connected to the rotating body, by installing a rotation supporting axle that protrudes out on the lower side of the vessel along the rotation axis to a bearing provided to the exterior, and by rotating the rotating body, it is possible for the reaction vessel to rotate in a state where it is stable with respect to the rotation axis.

An eleventh aspect of the invention is a reaction vessel wherein the opening part is, in a state where a rotation axis of the rotating body is passed therethrough, connectable such that it is detachable by means of a lower end section of the rotating body or a detachable cap that is detachable on the lower end section of the rotating body.

According to the eleventh aspect of the invention, at the lower end section of the rotating body, a cap is provided that covers the same, and since the opening part of the vessel is connected via the cap, in a case where high-speed rotation of the rotating body is performed, splashing of the liquid and the rotating body directly coming into contact with the liquid within the vessel is prevented, and cross-contamination can be avoided with certainty. Furthermore, by preventing the splashing of the liquid to the upper part, the liquid is pushed back to the lower side, and a more efficient introduction of the liquid into the reaction chamber can be achieved.

A twelfth aspect of the invention is a reaction vessel wherein the rotating body is a nozzle in which suction and discharging of gas is possible, and the nozzle has a rotation axis in an axial direction thereof, or parallel to the same.

According to the twelfth aspect of the invention, by using a nozzle as the rotating body, it can be utilized as a dispensing device, and a variety of processes can be consistently automated.

A thirteenth aspect of the invention is a reaction vessel comprising a flow passage which, as well as communicating between the storage chamber and the reaction chamber, communicates between the reaction chamber and the exterior, and the liquid introducing section has a nozzle and a suction and discharging section that performs suction and discharging of gas via the nozzle, and the opening part of the storage chamber is connectable by means of the nozzle.

Here, "connection" includes contact and installation methods such as installation, engagement, threading, engaging fitting, engaging attachment, engaging insertion, welding, or close contact.

Furthermore, the reaction chamber is, for example, communicated with the storage chamber via the upper section, and in regard to the suction and discharging port, for example, it is provided on the lower end of the flow passage that communicates at the lower section of the reaction chamber. Here, by forming the flow passage with a small diameter, it is possible to handle various vessels provided on the exterior. The size of the storage chamber is a size that can introduce the fluid into the reaction chamber by suction of the fluid, or a size that makes the suction and discharging by the nozzle possible. As a result of the consequent suction of the fluid by the nozzle, the fluid is introduced from the suction and discharging port into the reaction chamber.

In regard to the nozzle, it is preferable for it to be provided on a dispensing device in which horizontal movement and vertical movement is possible. Consequently, by moving the nozzle to vessels provided at various positions, it becomes possible to perform a further variety of processes. In regard to the nozzle, rotational movement including revolution is not necessarily made possible, although in a case where rotational movement is made possible, it benefits the homogenization of the liquid.

In regard to the interval between the storage chamber and the reaction chamber, there is a case where they are communicated via a flow passage, or there is a case where they are directly communicated at the interval between the storage chamber and the reaction chamber. In the thirteenth aspect of the invention, since it has two flow passages, the reaction chamber has two openings at the interval with the flow passages.

According to the thirteenth aspect of the invention, the nozzle is used as the liquid introducing section, and the liquid is introduced into the reaction chamber by suction of the liquid to the storage chamber via the reaction chamber by means of the suction and discharging section. Accordingly, the liquid can be introduced with certainty into the reaction chamber without contamination by gas or bubbles. In this case, since there is no need to rotate the nozzle, the mechanism for introducing the liquid into the reaction chamber is simplified.

A fourteenth aspect of the invention is a reaction vessel wherein the reaction chamber is, within a pipette tip comprising a thick diameter section and a thin diameter section that is thinner than the thick diameter section, a gap formed between an outer face of a core which is stored inside an inner face of the pipette tip in which a spacer is intermediately present, and the inner face of the pipette tip, the storage chamber is a space within the thick diameter section formed above the reaction chamber, a thin diameter section of the pipette tip is a flow passage that communicates the exterior and the reaction chamber, and an opening part of the thick diameter section is connectable by means of the nozzle.

The spacer is, for example, a plurality of protrusion sections that protrude out in the outward direction from the outer face of the core, or a protrusion section that protrudes out in the inward direction from the inner face of the pipette tip. There is a need for this gap to be communicated with the thin diameter section and the upper side of the thick diameter section.

In this case, the nozzle serving as the liquid introducing section, is rotatable, and the nozzle may have a rotation axis along the axial direction thereof In this case, as well as simplifying the introduction of the liquid into the reaction chamber by means of the rotation of the nozzle, the homogenization of the liquid can also be performed.

According to the fourteenth aspect of the invention, a core is stored in the pipette tip, the gap formed between the outer face of the core and the inner face of the pipette tip is used as the reaction chamber, the space within the thick diameter section of the upper side of the reaction chamber thereof is made the storage chamber, and a nozzle is connectable to the opening part of the storage chamber, that is to say, the thick diameter section. Accordingly, by suctioning the liquid, which is stored within the vessel provided to the exterior from the thin diameter section by means of the nozzle, from the reaction chamber towards the storage chamber, the liquid can be introduced into the reaction chamber. Furthermore, in regard to the product material produced by a reaction within the reaction chamber, by discharging gas from the nozzle, the product material can be discharged into the vessel from the reaction chamber via the thin diameter section, and the product material can be easily obtained.

A fifteenth aspect of the invention is a reaction vessel wherein a predetermined variety of biological materials are arranged in predetermined positions on the outer face of the core.

Consequently, for example, a target material labeled with a luminescent material, such as a fluorescent material, and a predetermined variety of biological materials are arranged in the predetermined positions, and by introducing the liquid in which the target material is suspended, and reacting the same, by measuring the luminescent position thereof, it is possible to analyze the structure of the target material or analyze the character thereof.

In order to arrange the predetermined biological materials in the predetermined positions on the outer face of the core, in addition to a case where the predetermined biological materials are fixed in the predetermined positions on the outer face of the core, there is a case where the predetermined biological materials are fixed at predetermined positions on a long and narrow shaped medium, such as a fibrous form or a filamentous form, and this is wound around the outer face of the core. In this case, by arranging the biological materials on the medium and winding the arranged medium around the core, the biological materials can be easily collected and arranged. Alternatively, by following along the medium, the luminescent position can be easily detected.

According to the fifteenth aspect of the invention, by fixing a predetermined variety of biological materials at predetermined positions on the outer face of the core, and by measuring the luminescent position of the labeled target material that has reacted with the biological materials, analysis of the target material can be performed.

A sixteenth aspect of the invention is a reaction vessel wherein the reaction chamber is sealable by sealing an interval between the nozzle or the storage chamber and the reaction chamber, and an interval between the reaction chamber and the exterior.

In order to seal the interval between the nozzle and the reaction chamber, for example, a first cap is engagingly insertably provided on the upper section of the storage chamber of the thick diameter section such that it is detachable, and in regard to the cap itself, it is detachably provided such that it is connectable to the nozzle. The cap that is connected to the upper section of the thick diameter section is further made movable in the downward direction of the upper section of the pipette tip, and by moving the cap in the downward direction and making it come into contact with the upper edge of the core stored within the pipette tip, the reaction chamber is sealed from the upper side. Furthermore, in regard to the lower side of the reaction chamber, by engagingly inserting the end of the thin diameter section into a second cap, the reaction chamber is sealed from the top and the bottom.

On the other hand, in order to seal the interval between the storage chamber and the reaction chamber, and the interval between the reaction chamber and the exterior, a portion or all of the flow passage or the reaction chamber is formed by a deformable soft material, and in regard to the sealing of the reaction chamber, it is performed by deforming the soft material. These caps, the movement device, or a pressing device for performing the deformation correspond to a sealing device.

According to the sixteenth aspect of the invention, by means of sealing the reaction chamber, and by quickly and easily preventing the discharging of the liquid, which has been introduced to the reaction chamber, from the reaction chamber, an efficient and quick introduction of the liquid can be performed.

A seventeenth aspect of the invention is a reaction vessel wherein the reaction chamber is formed in an approximate cylindrical shape, a side face of the reaction chamber has a smaller area than both bottom faces, and a height between both bottom faces is formed less than a thickness of the storage chamber.

According to the seventeenth aspect of the invention, by forming the reaction chamber in an approximate cylindrical shape, and by irradiating or receiving light with respect to the side face, uniform optical information can be obtained.

An eighteenth aspect of the invention is a reaction vessel liquid introducing device comprising; one or two or more reaction vessels, and one or two or more liquid introducing sections to which the reaction vessel is connectable such that it is detachable, and the reaction vessel has: a storage chamber in which liquid is storable, that has an opening part; a reaction chamber that is formed thinner or narrower than the storage chamber; and at least one flow passage that communicates between the storage chamber or the exterior and the reaction chamber, and liquid is introduced into the reaction chamber by means of a liquid introducing section.

Here, the "liquid introducing section" is, for example, a rotatable rotating body, which is connectable to the reaction vessel, and a rotational driving section that drives the rotating body, or a nozzle that connects to the reaction vessel and a suction and discharging section that suctions or discharges gas with respect to the nozzle. Furthermore, the rotating body may, at the same time, be the nozzle. Moreover, it is preferable for the liquid introducing section to store test reagents, and the like, or be mutually movable with respect to an external vessel, and the like, in which the test reagents are storable. Consequently, the automation of the processing can be even further advanced.

In order to make it "connectable such that it is detachable", for example, a reaction vessel is arranged before hand, the connection portion of the liquid introducing section is moved and connected as a result of engagement, threading, and the like, and detachment is, for example, performed by moving a plate for stripping the reaction vessel from the connection portion, or rotating in the reverse direction to the direction of threading.

By introducing the liquid from the reaction vessel liquid introducing device storage chamber according to the eighteenth aspect of the invention into the reaction chamber, the liquid can be easily thinned or capillarated. By using this reaction vessel, temperature control of the liquid can be performed with a high accuracy and faithful responsiveness.

By thinning or capillarating the liquid by means of the reaction vessel or the reaction vessel liquid introducing device, the time from giving the heating or cooling instruction until the liquid temperature becomes a uniform temperature distribution is shortened, and the process can be performed quickly and efficiently.

According to the reaction vessel or the reaction vessel liquid introducing device, by utilizing centrifugal force, thinning or capillaration can be performed in a state where contamination of bubbles and gas within the liquid has been removed. Consequently, when temperature control is performed, a uniform temperature distribution is obtained, and furthermore, optical information of a high precision can be measured.

Moreover, according to the reaction vessel, it is communicated by providing one flow passage between the storage chamber or the exterior and the reaction chamber. As a result, the interval between the reaction chamber and the storage chamber can be separated in terms of distance. Accordingly, for the reaction vessel liquid introducing device, which is based on centrifugal force, a large centrifugal force can be applied to the liquid that is to be introduced. Furthermore, for the reaction vessel liquid introducing device, which is based on suction and discharge forces, by communicating the interval between the exterior and the reaction chamber through a narrow flow passage, it becomes possible to insert the end section of the flow passage into various vessels. Moreover, it becomes easier to suction and easier to handle even a small quantity of liquid. Furthermore, by blocking the flow passage, it becomes easier to make the reaction chamber sealable.

Moreover, according to the reaction vessel, a storage chamber is provided for the reaction vessel, and by making the liquid temporarily storable in the storage chamber, the introduction of the liquid into the reaction chamber can be simplified.

Furthermore, by detachably providing the reaction vessel with respect to the liquid introducing section such as a rotating body provided to the exterior, the reaction vessel can be disposably formed, and hence the process can be inexpensively performed.

A nineteenth aspect of the invention is a reaction vessel liquid introducing device wherein the liquid introducing section has a rotatable rotating body, and a rotation driving section that rotationally drives the rotating body, and the reaction chamber of the reaction vessel connected to the rotating body is formed such that it is positioned farther away from the rotation axis of the rotating body than the storage chamber, and the reaction vessel rotates by means of rotation of the rotating body and introduces liquid stored in the storage chamber into the reaction chamber.

According to the present device, centrifugal force is applied to the liquid present in the storage chamber of the reaction vessel, and the liquid can be introduced into the reaction chamber, which is positioned farther away from a rotation axis than the storage chamber, in a state where it is not contaminated by gas. The reaction vessel can use the reaction vessels according to the first aspect of the invention to the fifteenth aspect of the invention.

Here, in regard to the rotation axis, there is a case where it passes through the vessel and it rotates about its own axis, and there is a case where it passes through the outside of the vessel and it revolves. In the case of rotation about its own axis, as well as being able to reduce the device scale, a variety of processes can be performed in a compact device by using the nozzle itself as the rotating body.

In regard to the "connection", this is as explained for the fifth aspect of the invention.

Here, in order to perform rotation about its own axis, there is a need to form the rotation axis of the rotating body connected to the vessel such that it passes through the vessel. In regard to the rotation axis of the rotating body, it is preferable for it to pass through the opening part of the storage chamber and make it connectable to the opening part.

Consequently, the opening part is covered by the rotating body, and the leaking of the liquid from the opening part can be prevented without covering the opening part with a cap, and the like.

According to the nineteenth aspect of the invention, a rotatable rotating body is provided as the liquid introducing section, and the reaction chamber is formed such that it is positioned farther away from the rotation axis than the storage chamber. That is to say, the reaction vessel rotates about its own axis or revolves, as a result of the rotation of the connected rotating body, and by means of this rotation about its own axis or this revolution, centrifugal force is applied to the liquid, and as a result of centrifugal separation, liquid or solid suspended in the liquid can be introduced with certainty into the reaction chamber in a state where gas and bubbles have been removed. Furthermore, in a case where the liquid is introduced by means of the reaction vessel rotating about its own axis, the liquid can be introduced with certainty without taking up space. That is to say, since the liquid can be introduced into the reaction chamber by the rotation of the vessel, a large space in which the reaction vessel is revolved around a rotation axis that passes only through the exterior thereof, is unnecessary, and the introduction of the liquid can be achieved by utilizing a small-scale rotation device of basically the size of one vessel. On the other hand, in a case where revolution is performed, a large centrifugal force can be obtained with a low rotational frequency.

In a case where the rotation axis of the rotating body is connected to the opening part such that it passes through the opening part of the storage chamber, since the opening part used originally for the introduction of liquid is also used for the installation of the rotating body, there is no need to provide a new rotating body installation section in the vessel, and the structure is simplified.

Furthermore, it is possible to more certainly and easily connect between the rotating body and the reaction vessel by threading or engagement, and particularly in a case where the rotating body is installed by threading, since the rotation of the rotating body can be utilized, it is efficient.

A twentieth aspect of the invention is a reaction vessel liquid introducing device wherein the rotating body is a nozzle in which suction and discharging of gas is possible, and a rotation axis of the nozzle runs along an axial direction of the nozzle thereof, or is parallel to the axial direction of the nozzle.

By using the nozzle also as the rotating body, a variety of diverse processes can be consistently performed by connecting a dispensing tip, such as the suction and discharging of the liquid, and a homogenization process of the suspension. Furthermore, although it is necessary for the rotating body to have a movement section that is movable in the vertical direction, if it is also movable in the horizontal direction, by moving the rotating body to vessels provided in various positions, it becomes possible to perform a wider variety of processes.

According to the twentieth aspect of the invention, by using a nozzle as the rotating body, it can be utilized as a dispensing device, and a variety of processes can be consistently automated.

A twenty-first aspect of the invention is a reaction vessel liquid introducing device wherein the flow passage of the reaction vessel comprises a liquid introduction flow passage for introducing liquid from the storage chamber or the exterior to the reaction chamber, and a discharge flow passage for discharging gas from the reaction chamber, and as well as a portion or all of the flow passage or the reaction chamber thereof being formed by a deformable soft material, it comprises a pressing section that seals the reaction chamber by pressing a predetermined portion of the soft material.

Here, in the case of the former combination, the liquid introducing section is a rotating body, and in the case of the latter combination, it is a nozzle and a suction and discharging section. In the latter case, the reaction chamber is, for example, communicated at the upper section of the storage chamber, and the liquid introduction flow passage is a flow passage that extends from the reaction chamber in the downward direction, and by forming the flow passage with a small diameter, it is insertable into a variety of vessels provided on the exterior. Furthermore, the discharge flow passage communicates the interval between the reaction chamber and the storage chamber provided on the upper side thereof, and the nozzle is, for example, connected to the opening part of the upper side of the storage chamber. Hence, it is communicated on the upper side via the discharge flow passage.

According to the present aspect of the invention, in the case of the latter combination, the liquid is introduced into the reaction chamber via the liquid introduction flow passage by means of the suction of fluid by the nozzle, and the gas present in the reaction chamber is suctioned into the nozzle through the storage chamber via the discharge flow passage. At that time, a portion of the liquid may be suctioned into the storage chamber.

According to the twenty-first aspect of the invention, a deformable soft material is provided for at least a portion of the flow passage or the reaction chamber, the reaction chamber is sealable by deforming the soft material, and a thinned or capillarated liquid that is not contaminated by gas is easily obtained. Consequently, the discharging of the introduced liquid from within the reaction chamber is prevented, and an efficient and quick introduction of the liquid can be performed.

A twenty-second aspect of the invention is a reaction vessel liquid introducing device comprising, in regard to the reaction vessel, a flow passage which, as well as communicating between the storage chamber and the reaction chamber, communicates between the reaction chamber and the exterior, and the liquid introducing section has a nozzle and a suction and discharging section that performs suction and discharging of gas via the nozzle, and the opening part of the storage chamber is connectable to a lower end section of the nozzle or is connectable to the lower end section of the nozzle via a cap that is connectable to the nozzle lower end section.

According to the twenty-second aspect of the invention, the nozzle is used as the liquid introducing section, and the liquid is introduced into the reaction chamber by suction of the liquid to the storage chamber via the reaction chamber by means of the suction and discharging section. Accordingly, the liquid can be introduced with certainty into the reaction chamber without contamination by gas or bubbles. In this case, since there is no need to rotate the nozzle, the mechanism for introducing the liquid into the reaction chamber is simplified.

A twenty-third aspect of the invention is a reaction vessel liquid introducing device wherein the reaction chamber of the reaction vessel is a gap formed between an outer face of a core, which is stored in a pipette tip comprising a thick diameter section and a thin diameter section that is thinner than the thick diameter section, and an inner face of the pipette tip, the storage chamber is a space within the thick diameter section formed above the reaction chamber, the thin diameter section of the pipette tip is a flow passage that communicates between the exterior and the reaction chamber, and the opening part of the thick diameter section is connectable by means of the nozzle.

According to the twenty-third aspect of the invention, a core is stored in the pipette tip, the gap formed between the outer face of the core and the inner face of the pipette tip is used as the reaction chamber, the space within the thick diameter section of the upper side of the reaction chamber thereof is made the storage chamber, and a nozzle is connectable to the opening part of the storage chamber, that is to say, the thick diameter section. Accordingly, by suctioning the liquid, which is stored within the vessel provided to the exterior from the thin diameter section by means of the nozzle, from the reaction chamber towards the storage chamber, the liquid can be introduced into the reaction chamber.

Furthermore, in regard to the product material produced by a reaction within the reaction chamber, by discharging gas from the nozzle, the product material can be discharged into the vessel from the reaction chamber via the thin diameter section, and the product material can be easily obtained.

A twenty-fourth aspect of the invention is a reaction vessel liquid introducing device comprising a sealing device that fluidically seals between the nozzle or the storage chamber and the reaction chamber, and between the reaction chamber and the exterior.

Here, as the "sealing device", for example, in regard to the interval between the nozzle and the reaction chamber, a first cap is detachably and engagingly insertably provided on the upper section of the storage chamber of the thick diameter section, and in regard to the cap itself, it is detachably provided such that it is connectable to the nozzle. By further moving the cap that is connected to the upper section of the thick diameter section in the downward direction at the upper section of the pipette tip, and by making it come into contact with the upper edge of the core stored within the pipette tip, the reaction chamber is sealed from the upper side. Furthermore, the lower side of the reaction chamber is sealed as a result of connecting by means of engagingly inserting the end of the thin diameter section into a second cap. That is to say, in a case where the first cap is moved by means of the lower end section of the nozzle, it is a raising and lowering movement device of the nozzle and a horizontal movement device that moves the nozzle to the position at which the second cap is disposed.

According to the twenty-fourth aspect of the invention, by sealing the reaction chamber, a reaction and the measurement thereof can be performed with high reliability in a state where gas has been removed. Furthermore, a quick and efficient introduction of the liquid can be achieved.

A twenty-fifth aspect of the invention is a liquid introducing and reaction measuring device comprising: one or two or more reaction vessels, and one or two or more liquid introducing sections to which the reaction vessel is connectable such that it is detachable, and the reaction vessel is a vessel that has: a storage chamber in which liquid is storable, that has an opening part; a reaction chamber that is formed thinner or narrower than the storage chamber; and at least one flow passage that communicates between the storage chamber or the exterior and the reaction chamber, and as well as further having a heating and cooling section that is able to heat or cool the one or two or more reaction chambers, and an optical information measuring section that obtains optical information within the one or two or more reaction chambers, it causes a reaction with regard to the liquid introduced into the reaction chamber by the liquid introducing section, and measures the optical information thereof.

Here, in regard to the face of the reaction chamber that performs heating or cooling with respect to the reaction chamber, the face that receives the light from the reaction chamber, and the face that irradiates light to the reaction chamber, a case where they are the same face, and a case where they are different faces, is possible.

In regard to the optical information measuring section, at the very least, one or two or more light reception end sections for receiving light from the reaction chamber are provided in contact with, or in the vicinity of, the reaction chamber. In a case where the luminescent material is a fluorescent material, or the like, it has one or two or more irradiation end sections which irradiate excitation light for generating fluorescence.

Furthermore, it is preferable for the interval between the reaction chamber of the reaction vessel, which is connected to the liquid introducing section, and the heating and cooling section or/and the optical information measuring section to be mutually movable. Consequently, the automation and simplification of the processing can be promoted.

According to the twenty-fifth aspect of the invention, heating and cooling is performed by the heating and cooling section provided making contact with, or close to, the reaction chamber of the reaction vessel. Accordingly, a metallic block or the like is not necessary, and in regard to the thinned or capillarated liquid in a state in which it is not contaminated by gas or bubbles, temperature control of the liquid stored within the vessel can be performed with high precision and faithful responsiveness.

Furthermore, by heating or cooling the thinned or capillarated liquid in a state in which it is not contaminated by gas or bubbles, the process can be advanced quickly by shortening the time from giving the heating or cooling instruction until the liquid temperature is uniformly distributed.

Moreover, since the optical information within the reaction chamber is measured in a state where it is not contaminated by gas or bubbles, optical information of a high precision can be obtained.

In particular, if it is made so that the liquid is heated or cooled with the heating and cooling section sandwiched from both sides along the thickness direction, an even quicker and more efficient heating and cooling of the liquid can be performed.

A twenty-sixth aspect of the invention is a liquid introducing and reaction measuring device that further comprises a sealing device for sealing the reaction chamber of the reaction vessel.

Here, the sealing device is, for example, in a case where a part or all of the flow passage of the reaction vessel, or the reaction chamber, is formed by a deformable soft material, a pressing section that seals the reaction chamber by deforming the soft material, and in a case where the reaction chamber is a gap between the inner face of the pipette tip and the outer face of the core stored within the tip, it comprises a first cap, a second cap, and a movement device that moves the first cap in the downward direction and moves the pipette tip to the position of the second cap, and connects the lower end section of the tip thereof to the second cap. Furthermore, the pressing section is a protrusion section provided on the light reception end section mentioned below, or a protrusion section provided on the end face of the irradiation end section of the optical information measuring device. In addition, examples of the sealing device include, an ultrasonic wave radiating device, or a welding device which use high frequency waves, laser, heat, and the like.

According to the twenty-sixth aspect of the invention, by sealing the reaction chamber, a reaction and the measurement thereof can be performed with high reliability in a state where gas has been removed. Furthermore, a quick and efficient introduction of the liquid can be achieved.

A twenty-seventh aspect of the invention is a liquid introducing and reaction measuring device wherein the optical information measuring section comprises one or two or more irradiation end sections that irradiate light to the reaction chamber, and one or two or more light reception end sections that receive light from the reaction chamber, the irradiation end section is provided such that it makes contact with or is in the vicinity of, amongst a plurality of walls that enclose the reaction chamber, at least one wall with the largest area, and the light reception end section is provided such that it makes contact with or is in the vicinity of at least one of the walls excluding the largest wall.

According to the twenty-seventh aspect of the invention, since by irradiating light on the wall with the largest area, a sufficient light quantity can be irradiated to the reaction chamber as a whole, optical information can be efficiently obtained.

A twenty-eighth aspect of the invention is a liquid introducing and reaction measuring device, wherein the optical information measuring section comprises one or two or more irradiation end sections that irradiate light to the reaction chamber, and one or two or more light reception end sections that receive light from the reaction chamber, and the irradiation end section and the light reception end section are provided such that they make contact with or are in the vicinity of one of the walls amongst the plurality of walls that enclose the reaction chamber.

According to the twenty-eighth aspect of the invention, since the irradiation end sections and the light reception end sections are provided at one of the walls of the reaction chamber, as well as being able to make a compact configuration, the number of components can be reduced.

A twenty-ninth aspect of the invention is a liquid introducing and reaction measuring device wherein the optical information measuring section comprises one or two or more irradiation end sections that irradiate light to the reaction chamber, and one or two or more light reception end sections that receive light from the reaction chamber, and the heating and cooling section comprises a heating and cooling end section that performs heating or cooling and is provided such that it makes contact with or is in the vicinity of the reaction chamber, and the irradiation end section of the optical information measuring section and the heating and cooling end section are provided such that they make contact with or are in the vicinity of one of the walls amongst the plurality of walls that enclose the reaction chamber.

Here, the "heating and cooling end section", in addition to a case where one end section performs the heating and the cooling as in a Peltier element, there is a case where it denotes either of a separately provided heating end section or cooling end section, or a case where it denotes both a heating end section and a cooling end section.

According to the twenty-ninth aspect of the invention, by providing the heating and cooling end section and the irradiation end section on one wall, the device scale is reduced, and it can be efficiently arranged.

A thirtieth aspect of the invention is a liquid introducing and reaction measuring device wherein a heating body or a cooling body of the heating and cooling section is provided on the irradiation end section.

As a form thereof, for example, the irradiation end section is an optical system such as a rod lens, another lens, or a transparent body, the heating body is, for example, a resistance wire such as a nichrome wire, and there is a case where it is wound around the optical system, such as a rod lens, or there is a case where the heating body is enclosed within the optical system, such as the rod lens.

Furthermore, a multilayered photosensitive exothermic glass that is built-in to the optical system, such as the rod lens, may be used. Consequently, a heating and cooling end section, a heating end section, or a cooling end section with a translucency can be provided.

According to the thirtieth aspect of the invention, since by providing a heating and cooling end section to the rod lens, the rod lens can be used as a heating and cooling end section, the device scale can be reduced, and the narrow space of the surroundings of the reaction vessel can be effectively utilized.

A thirty-first aspect of the invention is a liquid introducing and reaction measuring device wherein the heating and cooling section is provided such that it makes contact with or is in the vicinity of the reaction chamber, and is a heating end section that performs heating or a cooling end section that performs cooling, and the heating end section or the cooling end section is provided such that it makes contact with or is in the vicinity of one wall with the largest area amongst the plurality of walls that enclose the reaction chamber. Here, together with the heating end section, the irradiation end section may also be provided for the wall. For example, a case where the heating end section and the irradiation end section are joined corresponds to such a case.

According to the thirty-first aspect of the invention, by providing a heating end section or a cooling end section on the wall with the largest area amongst the walls that enclose the reaction chamber, heating and cooling can be efficiently performed.

A thirty-second aspect of the invention is a liquid introducing and reaction measuring device wherein the heating and cooling section comprises a heating and cooling end section that performs heating or cooling, and the heating and cooling end section is relatively provided such that it can approach and separate with respect to the reaction vessel.

By controlling the position of the heating and cooling end section with respect to the reaction vessel, it can made to make contact with, or be in the vicinity of, or separated from, the reaction chamber, and consequently, the heat transmission efficiency can be changed.

In regard to "providing the heating and cooling end section such that it can approach and separate", there is a case where an end portion that is able to heat and cool is provided such that it can approach and separate, a case where only a heating end section is provided such that it can approach and separate, a case where only a cooling end section is provided such that it can approach and separate, and a case where a heating end section and a cooling end section are provided such that they can approach and separate.

According to the thirty-second aspect of the invention, by controlling the position of the heating and cooling end section with respect to the reaction vessel, it can make contact with, or be in the vicinity of, or be separated from the reaction chamber, and consequently, since the heat transmission efficiency can be changed, an efficient and highly accurate temperature control can be performed.

A thirty-third aspect of the invention is a liquid introducing and reaction measuring device wherein the heating and cooling section is one in which either a heating end section that performs heating or a cooling end section that performs cooling is provided for a plurality of regions, and for each region, a predetermined temperature amongst a plurality of types is provided, and an interval between the reaction chamber that is connected to the liquid introducing section, and the heating end section or cooling end section is relatively movably provided such that they are able to mutually approach or make contact.

Consequently, the setting of temperature resulting from a predetermined sequence can be replaced with a sequence that passes through the regions that provide the corresponding temperature, and movement control regarding the movement route and the residence time at each region. At that time, the plurality of regions are, according to the temperature setting sequence of the plurality of types to be set with respect to the reaction chamber, sequentially arranged, for example in a row form, a column form, a circumferential form, or a zig-zag form, such that they have a spacing at a level at which there are no mutual temperature effects. Consequently, the movement distance along the relative movement route in regard to the regions of the reaction chamber is minimized, and temperature control can be efficiently performed.

Furthermore, since they are relatively movable, both the liquid introducing section and the heating and cooling section may be provided such that they move, and for example, it is acceptable for the liquid introducing section to perform the movement between the regions, and in regard to the regions, for the heating end section or the cooling end section to be movably provided such that it can approach and separate with respect to the reaction chamber. An example of a plurality of types of temperatures, for example, is the temperatures that are set in the case of performing PCR. As the relative movement method between the liquid introducing section and the heating end section or the cooling end section, a device that moves the liquid introducing section itself in the vertical direction or the horizontal direction, or, a device that moves the heating end section or the cooling end section, or a combination of both devices thereof, are possible. Furthermore, in regard to the heating end section or the cooling end section, there is a case where only a predetermined temperature is supplyable, and a case where setting of the various temperatures of the same is possible. Moreover, it is acceptable if a region that is set to a given temperature comprises two separate portions, and they are respectively provided in oppositely facing positions such that they sandwich the movement route of the reaction chamber.

According to the thirty-third aspect of the invention, various settings towards the temperature can be executed by means of the relative movement of the liquid introducing section with respect to the regions of the reaction vessel. Consequently, since the temperature control can be replaced by the movement control between the reaction chamber and the regions, transportation processes of various test reagents and liquids, and processes of the same level, can be simplified and standardized. Furthermore, compared to a case where temperature control is performed by raising and lowering the temperature of a heating body, such as an aluminum block, which has a large heat capacity with respect to the reaction vessel, or a cooling body, the energy efficiency is high. Moreover, compared to the temperature raising and lowering control of a heating body, such as an aluminum block, which has a large capacity, or a cooling body, since it is possible to instantly move to a different temperature region, the relaxation time until the temperature stabilizes is shortened, and a high accuracy and a fine temperature control can be performed.

A thirty-fourth aspect of the invention is a liquid introducing and reaction measuring device wherein a gas jetting section is provided in an interval between adjacent regions, which are arranged along a relative movement route direction with respect to the regions of the reaction chamber, which jets gas of a temperature according to the arrangement such that the movement route direction is crossed.

In particular, in a case where the temperature of the reaction chamber is changed to a lower temperature than the temperature set at a given stage, low-temperature gas is jetted to the intervals between the adjacent regions. Consequently, the lowering to the low temperature that has been set can be smoothly performed. The gas jetting section also includes a fan. The gas jetting section is included in the heating and cooling section. The "movement route direction", for example, is a horizontal direction, a vertical direction, or a direction along the circumference. The gas jetting section uses, for example, a gas cylinder.

According to the thirty-fourth aspect of the invention, by jetting gas of a predetermined temperature between the adjacent regions, to which a plurality of temperatures have been set, along the relative movement route, as well as smoothly performing the shifting of the temperature, the mutual temperature effects between the adjacent regions can be blocked.

A thirty-fifth aspect of the invention is a liquid introducing and reaction measuring device wherein the optical information measuring section comprises the light reception end section, and the interval between the reaction chamber connected to the liquid introducing section and the light reception end section is relatively movably provided such that they mutually approach or make contact, and the light reception end section receives the light from the reaction chamber.

Here, it is preferable for the regions for which the light reception end sections are provided to be, including the regions for which the heating and cooling sections are provided, arranged along the relative movement route with respect to the regions of the reaction chamber in the processing sequence thereof. For example, in a case where measurement is performed after temperature setting, they are provided such that they are positioned after the final temperature setting region along the movement route.

According to the thirty-fifth aspect of the invention, the liquid introducing section is relatively movable at the interval between the light reception end sections of the optical information measuring section, and furthermore, the light reception end sections are provided along the relative movement route. Consequently, by matching the arrangement between the processing procedure and the regions, processing can be efficiently performed. Furthermore, since the temperature control and the measurement of the optical information can be performed by the same movement control, the control is simplified.

A thirty-sixth aspect of the invention is a liquid introducing and reaction measuring device wherein the optical information measuring section comprises one or two or more irradiation end sections that irradiate light into the reaction chamber, and the irradiation end sections are detachably provided with respect to the reaction vessel.

By controlling the positions of the irradiation end sections with respect to the reaction vessel, light irradiation with a good efficiency is performed, and furthermore, in a case where the irradiation end sections and the heating end section are joined, it is possible to perform control of heat transmission, heat blocking, and the like.

According to the thirty-sixth aspect of the invention, by controlling the positions of the irradiation end sections with respect to the reaction vessel, light irradiation with a good efficiency is performed, and furthermore, in a case where the irradiation end sections and the heating end section are joined, it is possible to perform control of heat transmission, heat blocking, and the like. Consequently, temperature control and light irradiation can be performed efficiently and with a high accuracy.

A thirty-seventh aspect of the invention is a liquid introducing and reaction measuring device wherein the heating and cooling section comprises a cooling end section that performs cooling, and the cooling end section is a fan that blows air towards the reaction vessel.

Consequently, particularly at the time the heating end section or the irradiation end section is separated from the reaction vessel, by sending in air by means of the fan, heat dissipation of the reaction chamber is promoted, and the heat control can be performed with good efficiency.

According to the thirty-seventh aspect of the invention, particularly in a case where, as a consequence, the heating end section and the irradiation end section are separated from the reaction vessel, and the reaction chamber is cooled, by sending in air by means of the fan, heat dissipation of the reaction chamber is promoted, and the heat control can be performed with good efficiency.

A thirty-eighth aspect of the invention is a liquid introducing and reaction measuring device wherein the reaction chamber of the reaction vessel is formed in a cylindrical shape, is enclosed by two cylindrically shaped large walls and small walls, which are side faces, and is provided with one or two or more light reception end sections that receive the light advancing in the radial direction of the cylinder.

In a case where an irradiation end face is provided for the reaction chamber, it is provided such that the light is irradiated in the radial direction.

According to the thirty-eighth aspect of the invention, by forming the reaction chamber in an approximate cylindrical shape, and by irradiating or receiving light with respect to the side faces, uniform optical information can be obtained.

A thirty-ninth aspect of the invention is a liquid introducing and reaction measuring device wherein the optical information measuring section comprises: two or more irradiation end sections provided at each irradiation position of the two or more reaction chambers of the reaction vessel; a plurality of types of light sources that respectively generate light having a plurality of types of wavelengths; a light source selection section that temporally switches and selects one type of light from amongst the lights from the light sources, and simultaneously introduces it to the irradiation end sections; two or more light reception end sections provided at the light reception positions of the two or more reaction chambers of the reaction vessel; a light reception position selection section that temporally switches and selects the light from the light reception end sections; an optical filter selection section that temporally switches and selects among the plurality of types of optical filters that the light from the selected light reception position is to pass through; and a photoelectric element that sequentially inputs the light, which is the light from the selected light reception position, that has passed through the selected optical filter.

Here, providing a plurality of types of optical filter is, for example, for a case such as where a labeling material for labeling the DNA fragment, and the like, for which the quantity or the concentration is to be measured, that outputs light of a plurality of wavelengths is used in realtime PCR and the like within the reaction chamber. Consequently, by transmitting light having various wavelengths through an optical filter, the presence of the corresponding labeling material, or the quantity thereof, can be measured.

The "photoelectric element" is an electron element utilizing the photoelectric effect, and includes photoelectric cells, photomultipliers, photoconductive cells, phototransistors, photodiodes, and the like.

The irradiation of the light becomes necessary in order emit light by irradiating excitation light to a fluorescent material, and the like, that may be present in the reaction chamber.

According to the thirty-ninth aspect of the invention and a fortieth aspect of the invention, even in a case where two or more labeling materials are used with respect to two or more reaction vessels, the process can be performed using a small number of photoelectric elements by temporally switching the reaction chamber and the type of labeling material that becomes the subject of the labeling material. Therefore the device scale as a whole can be reduced or simplified.

A fortieth aspect of the invention is a liquid introducing and reaction measuring device wherein the optical information measuring section comprises: two or more irradiation end sections provided at each irradiation position of the two or more reaction chambers of the reaction vessel; a plurality of types of light sources that respectively generate light having a plurality of types of wavelengths; a light source irradiation position selection section that temporally switches and selects one type of light from amongst the lights from the light sources, and temporally switches the selected light and introduces it to each light reception end section; two or more light reception end sections provided at the light reception positions of the two or more reaction chambers of the reaction vessel; an optical filter selection section that temporally switches and selects among the plurality of types of optical filters that the light from the selected light reception position is to pass through; and a photoelectric element that sequentially inputs the light that has passed through the selected optical filter.

A forty-first aspect of the invention is a liquid introducing and reaction measuring device wherein the optical information measuring section comprises an irradiation end section that irradiates light to the reaction chamber of the reaction vessel, and a light reception end section that receives the light from the reaction chamber, and a light reception direction and an opening angle with respect to the reaction chamber of the light reception end section is outside of incidence and reflection routes determined based on an irradiation direction of the irradiation end section and a shape of the reaction chamber, and is determined such that the light reception end section receives the light from the reaction chamber.

The irradiation end section and the light reception end section corresponds to, for example, an optical system such as a rod lens, or an end of a fiber. For example, the irradiation end sections are provided in the regions in which the light reception end sections are provided, and in opposing regions that sandwich the movement route through which the reaction chamber, which has a translucency, moves. In this case, so that the optical axis of the irradiation end sections and the optical axis of the light reception end sections, or the incident angle to the reaction chamber and the transmission angle from the reaction chamber achieve a fixed finite angle, the optical system, such as a rod lens or the end of a fiber, is mutually inclined by the angle, or the effect of the irradiation end sections on the light reception end sections is reduced by using a fiber rod glass, and the measurement of the optical information can be made a high accuracy. In regard to the position of the irradiation end sections and the light reception end sections with respect to the reaction chamber, there is a case where they are positioned such that they sandwich the large wall face of the reaction chamber, a case where they are respectively positioned at the large wall face and the small wall face, a case where they are positioned such that they sandwich the small wall face, or a case where they are positioned on the same wall face.

A forty-second aspect of the invention is a liquid introducing device having: one or two or more rotatable rotating bodies; one or two or more vessels that are connectably formed such that they are detachable on the rotating body; and a rotational drive section that rotationally drives the rotating body, and the vessel has: a storage chamber, in which liquid is storable, that has an opening part; and a working chamber that is communicated with the storage chamber and is provided such that the passing of liquid is possible, and a medium that performs a predetermined operation on the liquid interrupts a passage route of the liquid, and the working chamber is formed such that it is positioned farther away from a rotation axis of the rotating body than the storage chamber, and liquid stored in the storage chamber is introduced into the working chamber.

The vessel may be made connectable to the rotating body via a cap.

Here, examples of the "medium" include a stationary phase such as a filter or a column as mentioned below. The filter includes a case where liquid is passed through by means of a plurality of piercing holes or voids that have a predetermined size (pore diameter or the average diameter or length of the voids), and a predetermined material within the liquid is separated, or a case where it is separated by means of adsorption. A case in which the rotation axis of the rotating body passes through the vessel corresponds to rotation about its own axis, and the device scale as a whole can be made smaller. Consequently, for example, it can be utilized in the extraction and the purification of various biological materials, such as nucleic acids, oligonucleotides, and proteins.

A forty-third aspect of the invention is a liquid introducing device wherein the rotating body is a rotatable nozzle in which the suction and discharge of gas is possible, and the nozzle has a rotation axis along an axial direction thereof.

A forty-fourth aspect of the invention is a liquid introducing device wherein the medium is a filter having a predetermined pore diameter.

A forty-fifth aspect of the invention is a liquid introducing device wherein the working chamber comprises a filter chamber that is communicated with the storage chamber and has the filter, and a housing chamber that is communicated with the filter chamber and that is detachably installed with respect to the filter chamber, and liquid that is introduced to the filter chamber as a result of rotation of the rotating body reaches the housing body by passing through the filter.

Here, the material transmitted through the filter is stored in the housing chamber. The interval between the housing chamber and the filter chamber is, for example, connected by an installation member.

A forty-sixth aspect of the invention is a liquid introducing device wherein the medium is a predetermined stationary phase, the working chamber is communicated with a column in which the medium is stored and the column, and comprises a housing chamber that is detachably installed with respect to the column, and liquid introduced into the column as a result of rotation of the rotating body reaches the housing chamber by passing through the column.

Here, the "stationary phase" is a solid or a liquid. In regard to the column, for example, the sample mixture is moved on the column by an appropriate eluent (mobile phase), and it is used to separate by utilizing the difference in movement speed based on the differences in the adsorptivity and the partition coefficient of the components.

A forty-seventh aspect of the invention is a liquid introducing device wherein the working chamber is formed thinner or narrower than the storage chamber.

According to the forty-second aspect of the invention, the forty-fourth aspect of the invention, the forty-fifth aspect of the invention, the forty-sixth aspect of the invention, and the forty-seventh aspect of the invention, by rotating, at the very least, the storage chamber and the various vessels which have a working chamber further away from the rotation axis by connecting to the rotating body, under atmospheric pressure, even in a case where passing of the liquid with respect to the medium provided in the working chamber is difficult, the passing of the liquid can be simplified by utilizing centrifugal force. Furthermore, by performing the introduction of the liquid by connecting various vessels, a wide variety of processes can be performed. Moreover, by achieving the introduction of the liquid by means of the rotation of the vessel about its own axis, the working region is made smaller compared to a case where revolution is utilized, and processing can be efficiently performed. In particular, by using a filter, and the like, that has a function of extracting or purifying nucleic acids, proteins, and the like, as the medium, extraction and purification of biological materials, such as nucleic acids and proteins, can be performed. Then, by combining with the PCR process, processes such as extraction, amplification, expression, and purification of nucleic acids, proteins, and the like, can be consistently performed. Furthermore, according to the forty-fourth aspect of the invention or the forty-fifth aspect of the invention, by providing a detachable housing chamber with respect to the working chamber, since a liquid to which a predetermined operation has been applied is stored and can be easily taken out, it is easy to use. Moreover, according to the forty-sixth aspect of the invention, as well as applying a predetermined operation to the liquid, a process that performs thinning or capillaration of the liquid to which the operation has been applied can be efficiently performed at the same time.

According to the forty-third aspect of the invention, a rotatable nozzle is utilized as the rotating body. Consequently, not only a centrifugal force, but the pressure of suction and discharging can be utilized. Hence dispensing of the liquid into the storage chamber can also be performed. Furthermore, depending on the shape of the vessel, the pressure of suction and discharging can be utilized for the introduction of the liquid to the reaction chamber. Hence a wide variety of processes can be consistently performed.

A forty-eighth aspect of the invention is a liquid introducing and reaction measuring method comprising the steps of: storing a liquid which becomes a processing subject, in a storage chamber of a reaction vessel according the first aspect of the invention to the seventeenth aspect of the invention; introducing the liquid from the storage chamber to the reaction chamber of the reaction vessel; sealing the liquid in the reaction chamber by blocking an opening provided in the reaction chamber, or a flow passage; performing heating and cooling of the liquid sealed in the reaction chamber; and measuring optical information from the reaction chamber.

Here, the "liquid", for example, includes target materials such as nucleic acids, and necessary test reagents. "Storage" is, for example, performed by using a dispensing device. "Introduction" is, for example, performed by connecting the reaction vessel to the nozzle serving as the liquid introducing section, and rotating the reaction vessel, or by using the suction and discharge mechanism of the dispensing device serving as a liquid introducing section.

According to the forty-eighth aspect of the invention, heating and cooling is performed by the heating and cooling section provided making contact with, or close to, the reaction chamber of the reaction vessel. Accordingly, a metallic block or the like is not necessary, and in regard to the thinned or capillarated liquid in a state in which it is not contaminated by gas or bubbles, temperature control of the liquid stored within the vessel can be performed with high precision and faithful responsiveness. Furthermore, by heating or cooling the thinned or capillarated liquid in a state in which it is not contaminated by gas or bubbles, the process can be advanced quickly by shortening the time from giving the heating or cooling instruction until the liquid temperature is uniformly distributed. Furthermore, according to the present aspect of the invention, a series of processes can be automated by using the reaction vessel.

Moreover, since the optical information within the reaction chamber is measured in a state where the reaction chamber is sealed and it is not contaminated by gas or bubbles, optical information of a high precision can be obtained.

In particular, if it is made so that the liquid is heated or cooled with the heating and cooling section sandwiched from both sides along the thickness direction, an even quicker and more efficient heating and cooling of the liquid can be performed.

BEST MODE FOR CARRYING OUT THE INVENTION

Figure 1:
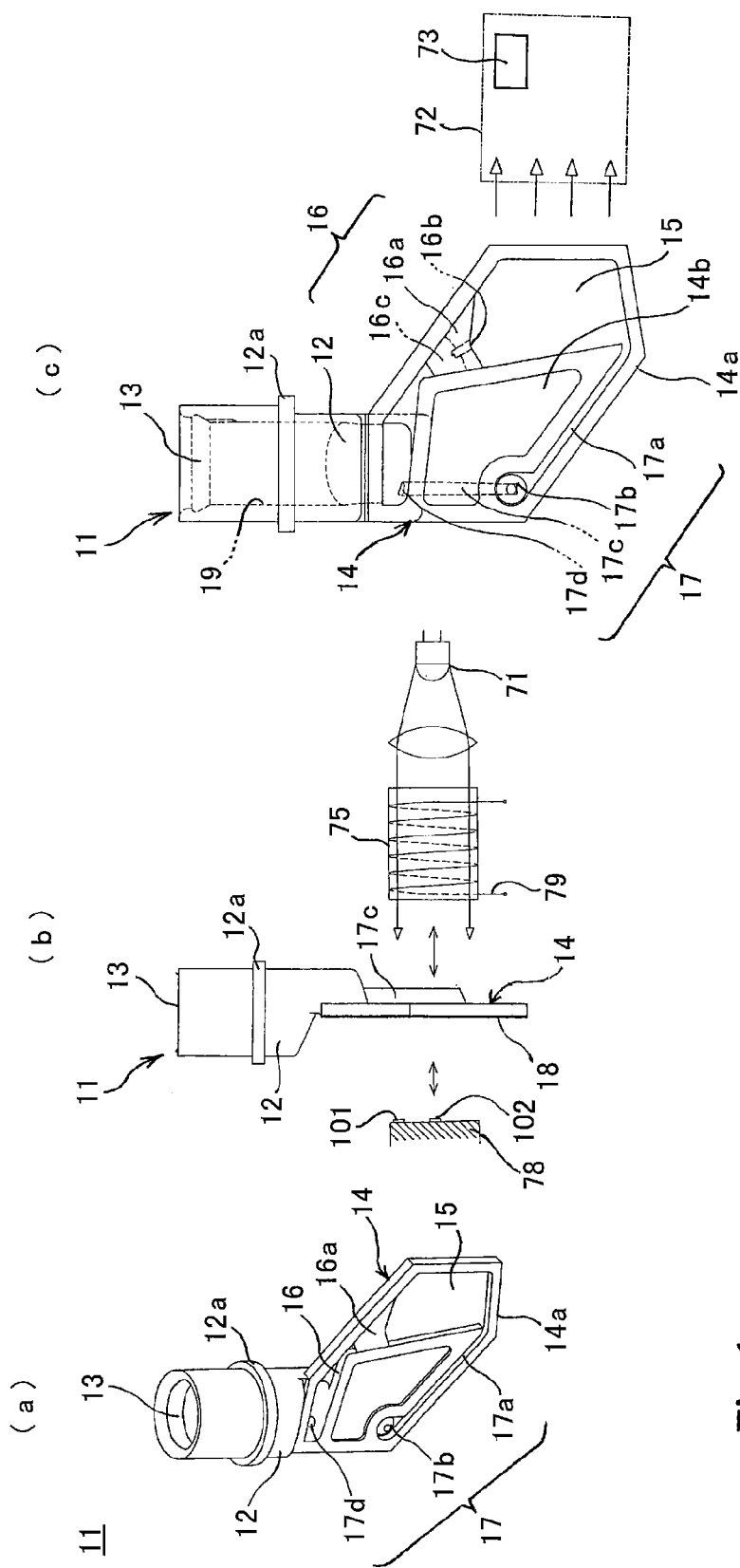
[FIG. 1] is a drawing showing a reaction vessel according to a first embodiment of the present invention.

According to the present invention, by introducing the homogenized suspension into the reaction chamber of the reaction vessel by utilizing centrifugal force or pressure, easy, certain, and uniform thinning or capillaration and sealing is achieved without contamination with bubbles or gas. As a result, the precision and responsiveness of the temperature control of the liquid is increased, and, for example, processes such as the measurement of quantities in real time PCR can be made quicker and more efficient.

Next, embodiments of the present invention are explained based on the drawings. Unless particularly specified, these embodiments should not be interpreted as limiting the present invention. Furthermore, the same parts in the embodiments are denoted by the same reference symbols, and the explanations have been omitted.

FIGS. 1(a),(b), and (c) are a perspective view, a side view, and a front view showing a reaction vessel 11 according to a first embodiment of the present invention. In FIGS. 1(a) and (c), in order to clearly show the interior, it is shown in a state where a transparent film 18, which forms a portion thereof and is a soft material, is removed.

As shown in FIG. 1(a), the reaction vessel 11 comprises: a cylindrical storage chamber 12 in which liquid is storable, which has an opening part 13 in the upper section; a reaction chamber 15 that is communicated with the storage chamber 12 via a liquid introduction flow passage 16 and a discharge flow passage 17 and is formed thinner than the storage chamber 12; and the liquid introduction flow passage 16, and the discharge flow passage 17. The liquid introduction flow passage 16, the discharge flow passage 17, and the reaction chamber 15 are formed in an approximate layer form that sandwiches the same, and the entirety thereof is a translucent reaction section 14. In the reaction vessel 11 according to the present embodiment, since the reaction chamber 15 is communicated with the liquid introduction flow passage 16 and the discharge flow passage 17, it corresponds to the fluid circuit mentioned above. In regard to the opening part 13, a cap 20 mentioned below is engagingly inserted and is connectable, and the cap 20 is further connectable by means of threading to a nozzle 22 mentioned below, serving as a rotating body. Accordingly, the opening part 13 is connectable to the nozzle via the cap 20. That is to say, in regard to the reaction vessel 11, as a liquid introducing section that introduces liquid into the reaction chamber 15, this belongs in a category that introduces by using a rotating body and applying centrifugal force.

The reaction chamber 15 is on the underside of the storage chamber 12, and with respect to the axis of the opening part 13 or the storage chamber 12, it is provided in a position farther away than the storage chamber 12 in terms of the position coordinate of the center of gravity of the chambers. When the reaction vessel 11 is installed on the nozzle 22 mentioned below, serving as a rotating body, the axis of the opening part 13 or the storage chamber 12 matches the rotation axis of the rotating body.

Accordingly, in a case where the rotating body is rotated, a centrifugal force is applied to the liquid within the storage chamber 12, and the liquid is introduced into the reaction chamber 15 of the reaction section 14, which is in a position farther away than the rotation axis. The reaction chamber 15, the liquid introduction flow passage 16, and a portion of the discharge flow passage 17 are provided in a planar frame 14a to which bottomed grooves have been formed, and one facial side of the frame 14a is sealed by the film 18 mentioned below. The liquid introduction flow passage 16 has an entrance at the inner face of the storage chamber 12 and has an exit at the upper portion of the reaction chamber 15, and the discharge flow passage 17 has an entrance at the lower section of the reaction chamber 15 and an exit at the inner bottom face of the storage chamber, and communicates between the reaction chamber 15 and the storage chamber 12.

The liquid introduction flow passage 16 comprises an elastic valve 16a as an elastic block material, which is formed from an elastic body, and the liquid introduction flow passage 16 is blockable by pressing the elastic valve 16a. Furthermore, the discharge flow passage 17 comprises a narrow inclined passage 17a that communicates with the lower section of the reaction chamber 15 and proceeds in a diagonally upward direction, a hole section 17b that protrudes out on the film 18 side such that it is sealable by pressing a small distance of the film 18, and an exit 17d that is provided on the inner bottom section of the storage chamber 12.

As shown in FIG. 1(b), the discharge flow passage 17 comprises a vertical passage 17c that fluidly connects from the hole section 17b to the exit 17d in the vertical direction parallel to the axis of the cylinder of the storage chamber, and the vertical passage 17c is provided such that it somewhat protrudes from the side in which the bottom face of the reaction chamber 15, and the like, of the planar frame 14a is provided. Furthermore, on the side face that opposingly faces the vertical passage 17c of the frame 14a, that is to say, the opening side of the reaction section 14, the film 18 is installed by adhesion, and the like, to the frame 14a such that the opening thereof is blocked, and it blocks the reaction chamber 15, and the openings of the flow passages 16 and 17. The film 18 is formed by a soft material, for example, by polyethylene or silicone, and the like, that is easily deformed by a pressing force. Consequently, although the reaction chamber 15 is enclosed by a plurality of walls, at the time of reaction, the light reception end section 78 of a bundle of fibers, and the like, on which pressing sections 101 and 102 are provided, is arranged such that it is positioned on the exterior of the wall to which this film 18 is provided, and on the wall on the opposite side thereof, a rod lens 75 that irradiates the light from the trigger light source 71, which generates excitation light, is positioned. Here, a resistance wire of the heating body 79 is wrapped around the rod lens 75 in order to make the rod lens 75 function as a heating end section. These light reception end section 78 and rod lens 75 are detachably provided with respect to the large wall of the reaction chamber 15.

By providing a portion of the discharge flow passage 17 near and parallel to the axis, in a case where the reaction vessel 11 is rotated about the axis, the introduction of the liquid through the discharge flow passage 17 by a centrifugal force is lessened.

As shown in FIG. 1(c), the elastic valve 16a of the liquid introduction flow passage 16 comprises on the interior, as mentioned below, a hole section 16b and a void 16c that is sealable by pressing. Furthermore, in regard to the upper portion inner face 19 of the storage chamber 12, the cap 20 mentioned below has an engagable inner diameter. On the outer face of the storage chamber 12, the detaching flange 12a of the reaction vessel 11 is provided. Furthermore, the light from the reaction chamber 15, which stores a fluorescent material, and the like, which luminesces by means of irradiation by excitation light, is, unlike FIG. 1(b), for example, received from a single wall amongst the walls that enclose the reaction chamber. In this example, the light is received from a light reception end section that is positioned on a predetermined small wall, and the light is introduced to the light receiving section 72 through an optical fiber.

Figure 2:
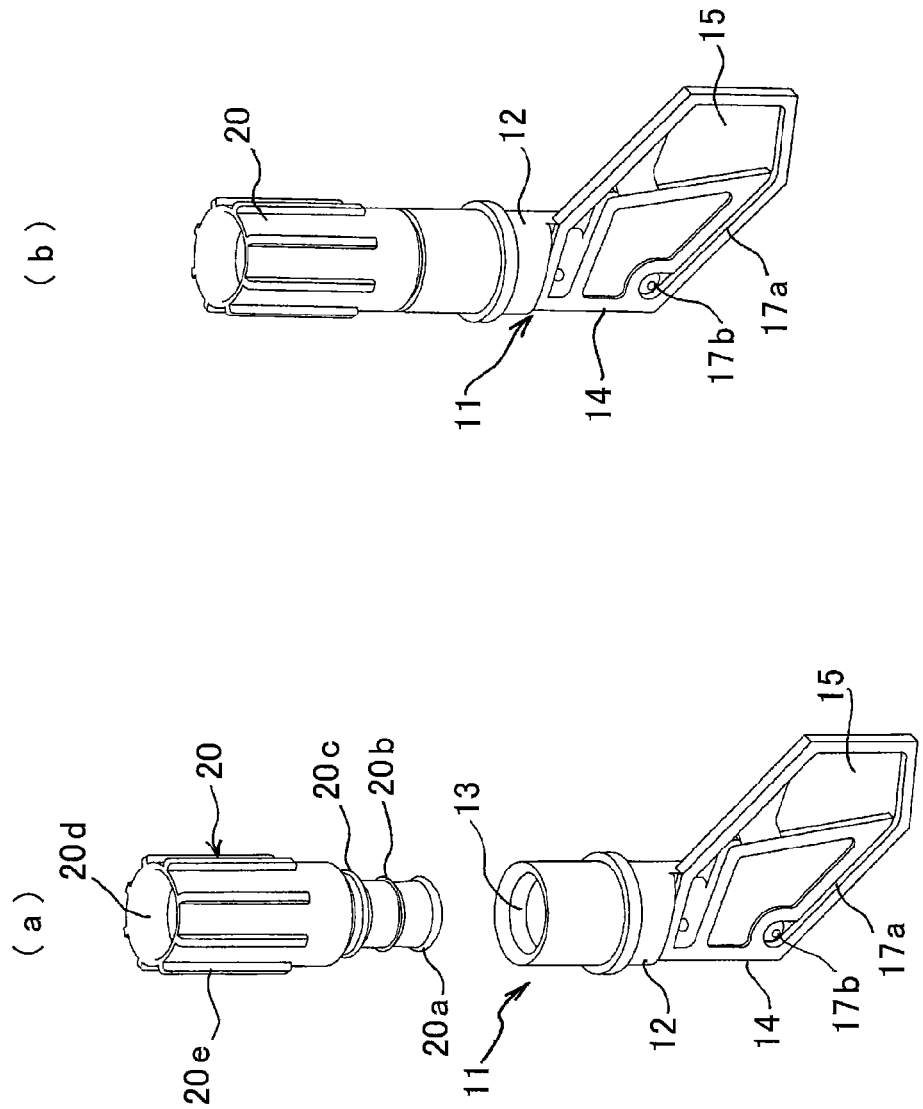
[FIG. 2] is a perspective view showing a reaction vessel and a cap according to the first embodiment of the present invention.

FIG. 2(a) is a perspective view showing the cap 20 that is to be connected to the reaction vessel 11, and the reaction vessel 11.

The cap 20 is a hollow cylinder-shaped member that is engagingly inserted and connected to the opening part 13 of the storage chamber 12 of the reaction vessel 11. The cap 20 has three types of annular protruding sections that make contact with the inner face of the opening part, and they are, from the bottom, airtight rims 20a and 20b, and a locking rim 20c. Furthermore, the inner face of the cap 20 is a nozzle engaging section 20d that engages a nozzle not shown in the drawing. Furthermore, on the outer face of the cap 20, a plurality of protuberances are provided along the axial direction of the cap 20, so that it is engagable with engaging sections 47a and 47b mentioned below, and consequently, the automatic detachment of the cap 20 becomes possible.

FIG. 2(b) is a drawing showing a state where the cap 20 is connected to the reaction vessel 11 by engagement.

Figure 3:
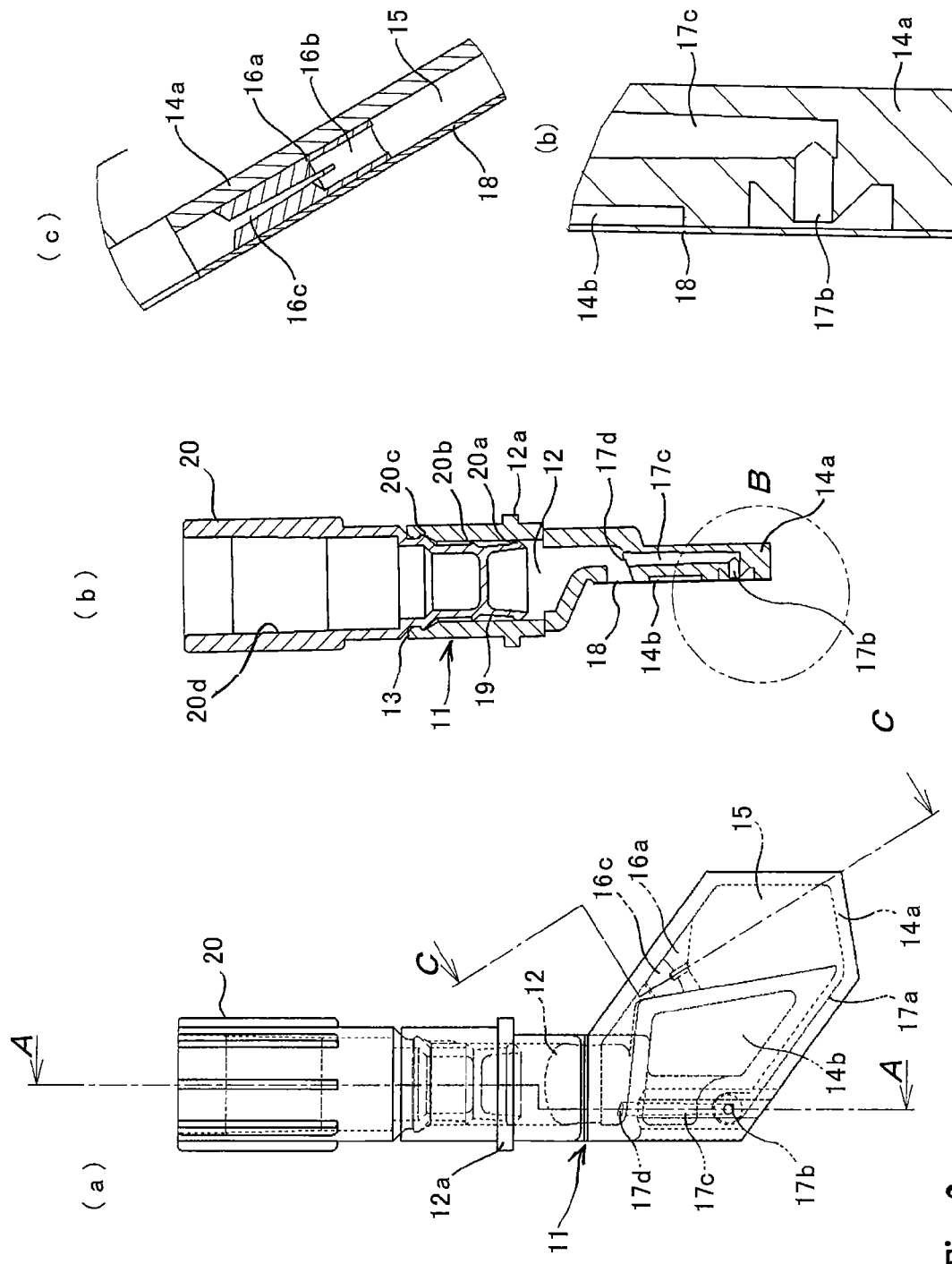
[FIG. 3] is an explanatory drawing of a reaction vessel according to the first embodiment of the present invention.

FIG. 3(a) is a drawing showing a front perspective view for showing the reaction vessel 11 in more detail, and is a state where the cap 20 is engaged and connected to the opening part 13. In the drawing, reference symbol 14b denotes a shallow indentation provided on the frame 14a. A cross-sectional view cut along the AA line thereof is shown in FIG. 3(b). In this drawing, a state where the airtight rims 20a and 20b, and the locking rim 20c, of the cap are making contact with the inner face of the upper portion of the storage chamber 12 is shown. Furthermore, the vicinity of the hole section 17b provided on the lower portion of the vertical passage 17c is shown enlarged in FIG. 3(d). Since the hole section 17b protrudes out to the film 18 side and is provided approaching the film 18 with a given spacing, by pressing the film 18 from the exterior, the hole section 17b is blocked by the film 18, and hence the discharge flow passage 17 is blocked.

Figure 4:
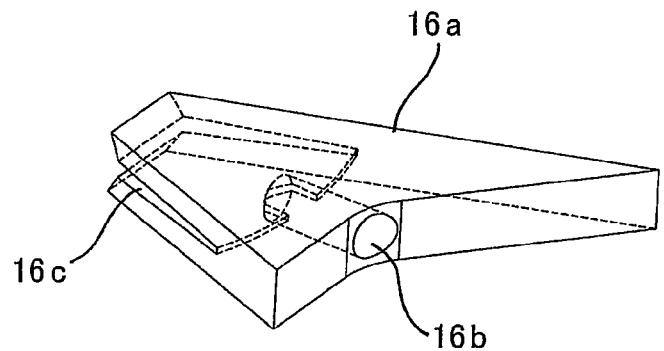
[FIG. 4] is a partially expanded perspective view of a reaction vessel according to the first embodiment of the present invention.

Furthermore, FIG. 3(c) is a drawing showing the main portions of a cross section cut along the CC line of FIG. 3(a). The portion is one exhibiting the liquid introduction flow passage 16 portion to which the elastic valve 16a has been provided, and it is provided between the frame 14a and the film 18. In regard to the elastic valve 16a, as becomes clearer by additionally referring to FIG. 4, it is formed from the hole section 16b, and the void 16c that is communicated with the hole section 16b, and the liquid introduction flow passage 16 can be blocked as a result of blocking the void 16c by pressing the void 16c. Consequently, the liquid introduced into the reaction chamber 15 can be sealed within the reaction chamber 15.

Figure 5:
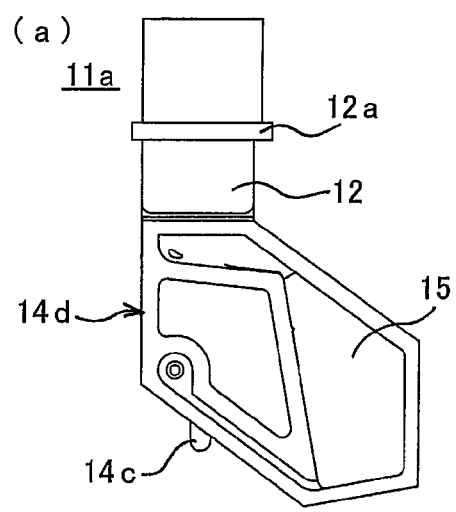
[FIG. 5] is a drawing showing a reaction vessel according to a second embodiment of the present invention.
Figure 5:
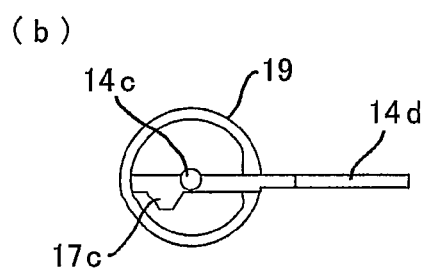

FIG. 5 shows a reaction vessel 11a according to a second embodiment. The reaction vessel 11a differs from the reaction vessel 11 mentioned above in that by providing a rotation supporting axle 14c along the axis of the opening part 13 of the storage chamber 12 on the underside of the reaction section 14 of the reaction vessel 11a, prevention of core deviation at the time of rotation can be achieved.

Figure 6:
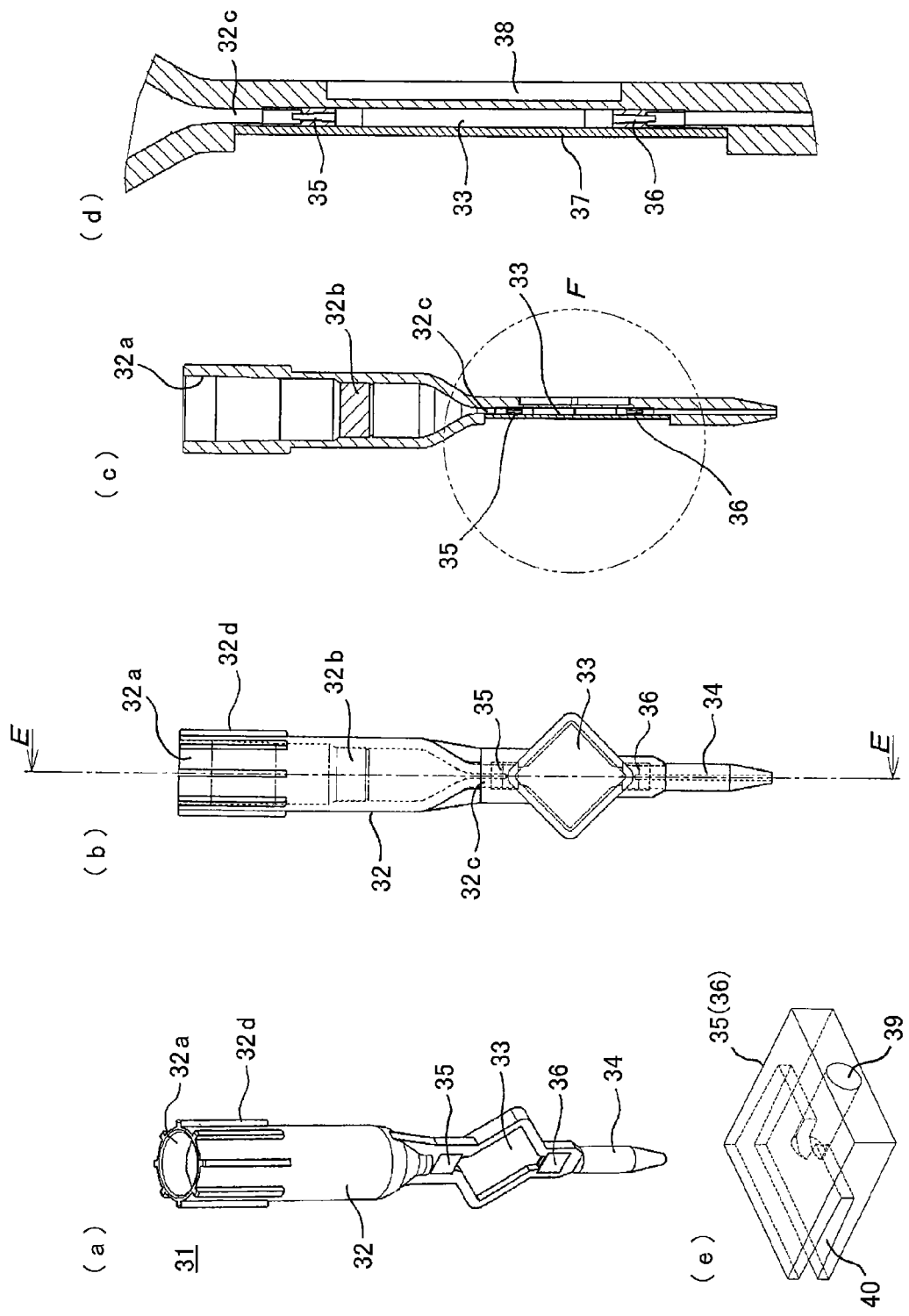
[FIG. 6] is a drawing showing a reaction vessel according to a third embodiment of the present invention.
Figure 7:
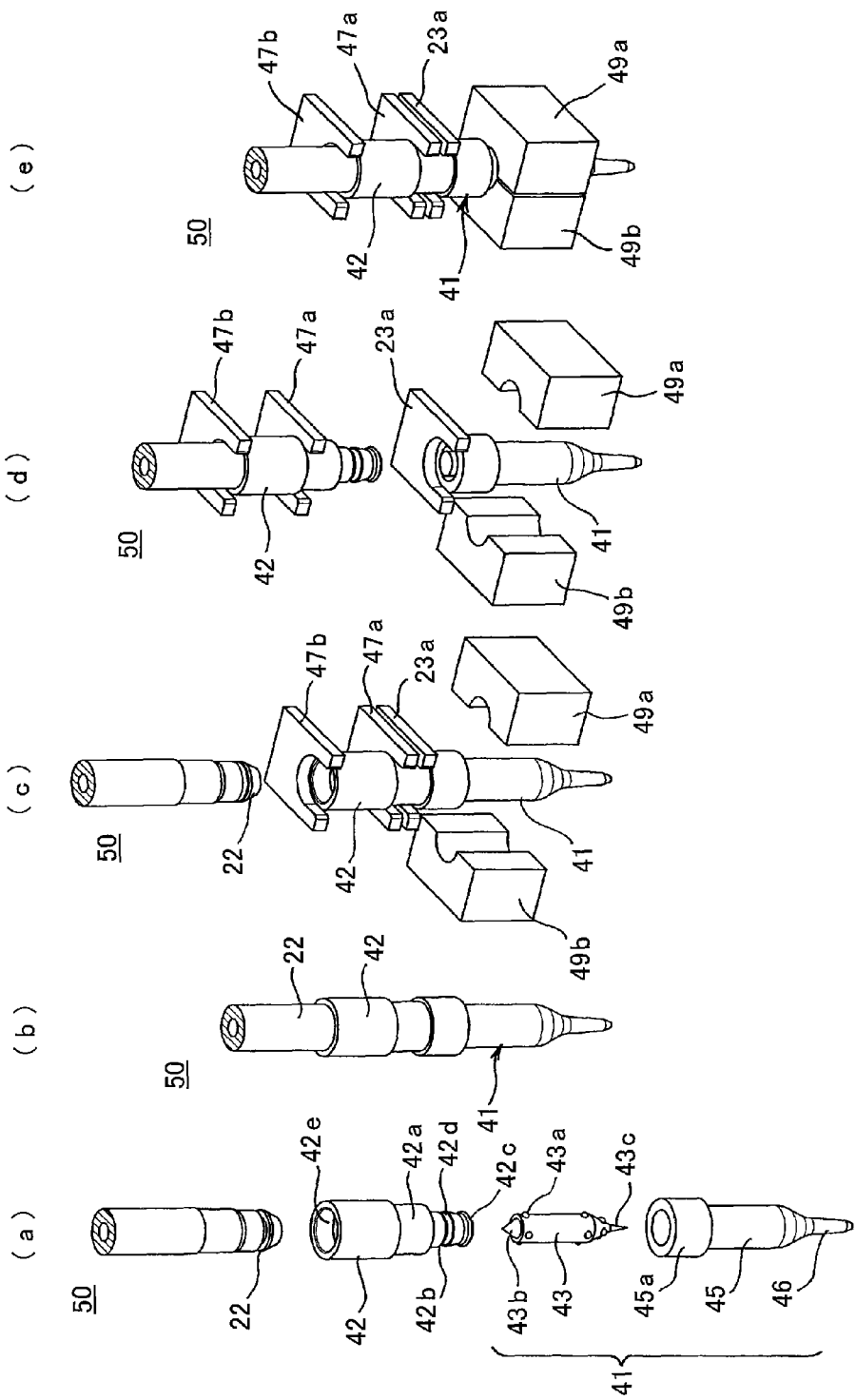
[FIG. 7] is a drawing showing a reaction vessel according to a fourth embodiment of the present invention.

Next, the reaction vessel, which belongs in a category wherein liquid is introduced by the suction and discharging of a nozzle, is explained based on FIG. 6 and FIG. 7.

FIG. 6 shows a reaction vessel 31 according to a third embodiment.

FIG. 6(a) shows a perspective view of the reaction vessel 31, FIG. 6(b) is a front view thereof, FIG. 6(c) is a cross-sectional side view thereof, FIG. 6(d) is an enlarged cross-sectional view of region F shown in FIG. 6(c), and FIG. 6(e) is an enlarged perspective view of a partial portion shown in FIG. 6(d).

The reaction vessel 31 comprises a cylindrical storage chamber 32 that has a thick diameter, a diamond-shaped prismatic reaction chamber 33 that is formed thinner than the storage chamber 32, and a thin diameter section 34 provided on the lower side of the reaction chamber 33 that is formed thinner than the cylinder.

An interval between the storage chamber 32 and the reaction chamber 33, and an interval between the reaction chamber 33 and the exterior, are connected by a flow passage 32c, and a thin diameter section 34, respectively. Consequently, in regard to the reaction vessel 31 according to the present embodiment, since the reaction chamber 33 is communicated with two flow passages, it corresponds to the fluid circuit. Furthermore, blocking positions of the flow passage 32c and the thin diameter section 34 are provided with elastic valves 35 and 36 that are blockable as a result of pressing.

In regard to the storage chamber 32, a nozzle not shown in the drawing is connectable to the opening part 32a thereof by engagement, and in the interior of the storage chamber 32 and on the lower side of the connection portion of the nozzle, for example, a heat insulating filter 32b is provided so as to partition the storage chamber 32. Consequently, the heating and cooling effects towards the reaction chamber 33 can be increased. Furthermore, the lower side of the storage chamber 32 is formed such that it becomes thinner at the end, and is communicated with the flow passage 32c. Furthermore, a plurality of protuberances 32d are provided on the outer face of the storage chamber 32, and by means of the protuberances 32d, it becomes automatically removable as a result of a tip removal plate 23a mentioned below.

One of the large walls of the reaction chamber 33 is lined with a film 37 that is formed from a soft material that is deformable by means of pressing, and in regard to the other large wall, as well as it being formed by the frame of the reaction vessel 31, a depression 38 that covers the reaction chamber 33 is provided on the frame in order to increase the thermal conductivity, and it is thinly formed.

The elastic valves 35 and 36 comprise, as shown in FIG. 6(e), a hole section 39, and a void section 40 that is blockable by means of pressing.

FIG. 7 is a tip-shaped reaction vessel 41 according to a fourth embodiment, and shows a cap 42 through which passage of fluid is possible, and a reaction vessel connection portion in which the tip-shaped reaction vessel 41 is connected to the nozzle 22 of the liquid introducing device 50, which is also a rotatable and vertically and horizontally movable reaction vessel liquid introducing device.

FIG. 7(a) is a disassembled perspective view of the reaction vessel connection portion of the liquid introducing device 50, FIG. 7(b) shows the reaction vessel connection portion of the liquid introducing device 50, and FIG. 7(c) to (e) shows the automatic detachment and connection operations from the liquid introducing device 50 with respect to the tip-shaped reaction vessel 41 at the time of movement using the liquid introducing device 50 to the region in which the heat conducting blocks 49a and 49b have been provided as heating end sections of the heating and cooling section, and heating and cooling is performed.

As shown in FIG. 7(a), the tip-shaped reaction vessel 41 comprises; a cylindrical thick diameter section 45, a thin diameter section 46 that is provided on the lower side of the thick diameter section 45 and that is formed thinner than the thick diameter section 45, an opening part 45a that is provided on the upper side of the thick diameter section 45, has an outer diameter even thicker than the thick diameter section 45, and in which the end section 42b of the cap 42 is engagingly insertable, and a cylindrical core 43 that is stored between the thick diameter section 45 and the thin diameter section 46. A plurality of protrusion sections 43a are provided on the outer circumferential face of the core 43 such that they protrude in the outer direction as spacers for creating a space with the inner circumferential face of the thick diameter section 45 or the thin diameter section 46. The space between the outer circumferential face of this core 43 and the inner circumferential face of the thick diameter section 45 corresponds to the reaction chamber. Furthermore, the space above the core 43 on the upper side of the thick diameter section 45 corresponds to the storage chamber.

Figure 8:
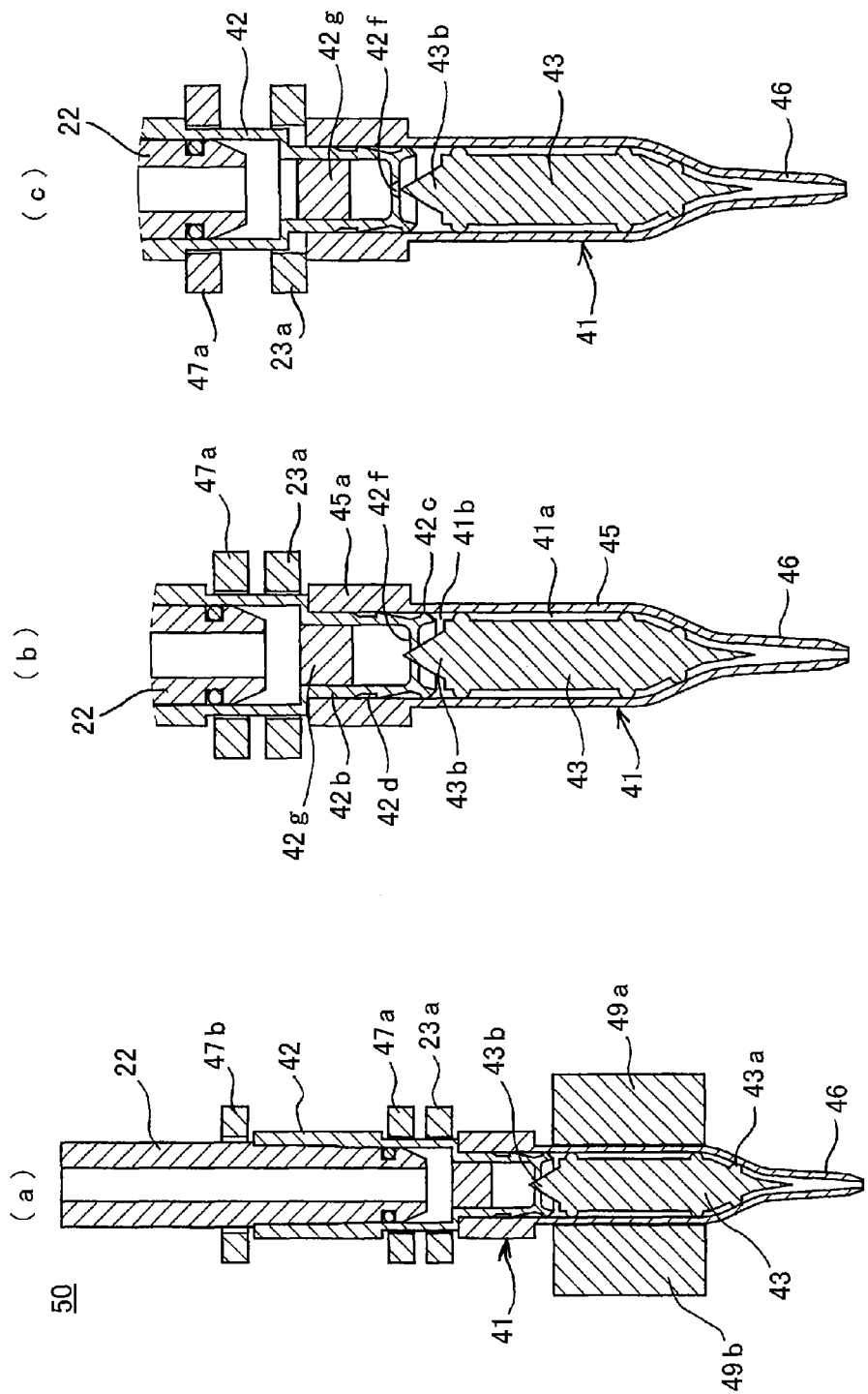
[FIG. 8] is a cross-sectional view of a reaction vessel according to the fourth embodiment of the present invention.

Moreover, the lower end of the core 43 is formed matching the shape of the thin diameter section 46 such that it becomes thinner at the end, and the upper end of the core 43 comprises a blocking section 43b that can disable the passage of fluid by blocking the end section 42b of the cap 42. In this example, the blocking section 43b is formed in a conical shape corresponding to a hole section 42f (refer to FIG. 8) provided on the end section 42b of the cap 42 that expands in the outer direction.

Furthermore, the cap 42 is an entirely hollow approximately cylindrical shape, and it comprises a base section 42a, an end section 42b that has an outer diameter that is formed narrower than the outer diameter of the base section 42a, and an engaging section 42e that has a thicker outer diameter than the outer diameter of the base section 42a to which the end of the nozzle 22 is engagable. A rim 42c that adheres to the inner face of the opening part 45a of the reaction vessel 41, and an annular groove 42d, is provided on the end section 42b.

As shown in FIG. 7(c) to FIG. 7(e), a state in which the reaction vessel 41 has been moved to the heat conducting blocks 49a and 49b of the heating and cooling section by means of a liquid introducing device 50 connected to the nozzle is shown. Furthermore, the liquid introducing device 50 comprises a tip removal plate 23a for stripping the tip-shaped reaction vessel 41, that and has a pierced semicircular notch that is somewhat smaller than the outer diameter of the opening part 45a, and is larger than the outer diameter of the base section 42a of the cap 42. The tip removal plate 23a is movably provided in the vertical direction, and approachably and separatably provided with respect to the reaction vessel 41, and consequently the axis of the nozzle 22. Furthermore, cap engaging sections 47a and 47b that are engagable to the stepped portion of the engaging section 42e of the cap, are provided for the liquid introducing device 50 such that they sandwich the engaging section 42e of the cap 42 from above and below. The cap engaging section 47a of the lower side has a semicircular notch that is larger than the outer diameter of the base section 42a of the cap 42 and is smaller than the engaging section 42e, and the cap engaging section 47b of the upper side has a semicircular notch that is larger than the outer diameter of the nozzle 22 and is smaller than the outer diameter of the engaging section 42e. Furthermore, the distance between the cap engaging section 47a of the upper side and the cap engaging section 47b of the lower side is fixed, and these cap engaging sections 47a and 47b are not only vertically movably provided, but also approachably and separatably provided with respect to the axis of the nozzle 22.

FIG. 7(c) shows a state in which by simultaneously lowering the cap engaging sections 47a and 47b, and the tip removal plate 23a to the lower side, the tip-shaped reaction vessel 41 to which the cap 42 is connected is removed from the nozzle 22, and the thick diameter section of the reaction vessel 41 is supported in a position sandwiched by the heat conducting blocks 49a and 49b.

FIG. 7(d) shows a state in which only the tip removal plate 23a is lowered in a state where the cap 42 is connected to the nozzle 22, and the reaction vessel 41 has been removed from the cap 42.

FIG. 7(e) shows a state in which the reaction vessel 41 is sandwiched by the heat conducting blocks 49a and 49b in a state where the reaction vessel 41 has been connected to the nozzle 22 via the cap 42.

FIG. 8(a) is a cross-sectional view cut at a plane through the axis of the nozzle 22 in FIG. 7(e).

As shown in the enlarged cross-sectional view of the reaction vessel 41 in FIG. 8(b), the gap section 41a enclosed by the outer face of the core 43 and the inner face of the thick diameter section 45 corresponds to the reaction chamber, and the space section 41b formed on the upper side of the thick diameter section 45 and the upper portion of the core 43 corresponds to the storage chamber. Furthermore, the hole section 42f, that has a shape that is blockable by means of the blocking section 43b of the core 43, is pierced through the end section 42b of the cap 42. The hole section 42f is blocked by the blocking section 43b in a state where the end section 42b is most deeply inserted into the opening part 45a of the reaction vessel 41. A partitioning filter 42g is provided on the upper side of the interior of the end section 42b, and the transmission of heat from the reaction chamber to the nozzle 22 is prevented. That is to say, since the reaction vessel 41 according to the present embodiment is provided with two openings in the reaction chamber thereof, it corresponds to the fluid circuit.

In FIG. 8(c), by moving the end section 42b of the cap 42 and the cap engaging sections 47a and 47b in the upper direction, the cap engaging sections 47a and 47b are hooked onto the engaging section 42e of the cap 42, and the cap 42 is somewhat moved in the upper direction. Then, the blocking section 43b of the core 43 is removed from the hole section 42f, and the nozzle 22 is communicated with the reaction vessel 41 via the partitioning filter 42g of the cap 42. Consequently, the thin diameter section 46 of the reaction vessel 41 is inserted into the vessel in which liquid has been stored, and by performing suction of gas by means of the nozzle 22 in a state where the position of the cap 42 is such that the hole section 42f is opened, the liquid is introduced to the space section 41b through the thin diameter section 46 of the reaction vessel 41 and the gap section 41a. Thereafter, it is made a state where the end section 42b of the cap 42 is most deeply inserted into the opening part 45a of the reaction vessel, and as well as the hole section 42f being blocked by the blocking section 43b, as a result of the end of the thin diameter section 46 being inserted into and engaging another cap that is not shown in the drawing, it is possible for liquid to be sealed within the gap section 41a.

Figure 9:
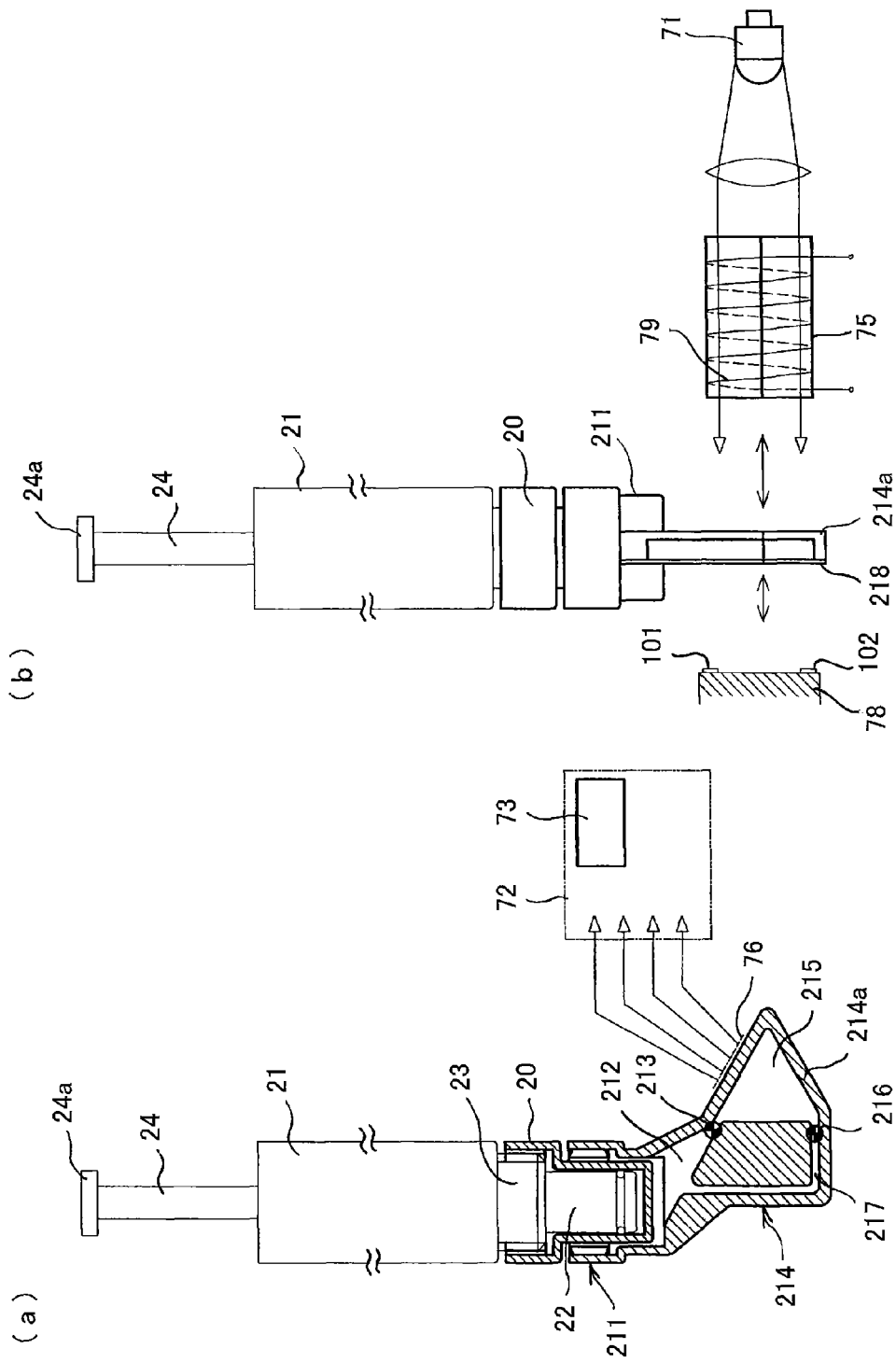
[FIG. 9] is a drawing showing a case where a reaction vessel according to a fifth embodiment of the present invention is connected to a nozzle, and reaction measurement is to be performed.
Figure 10:
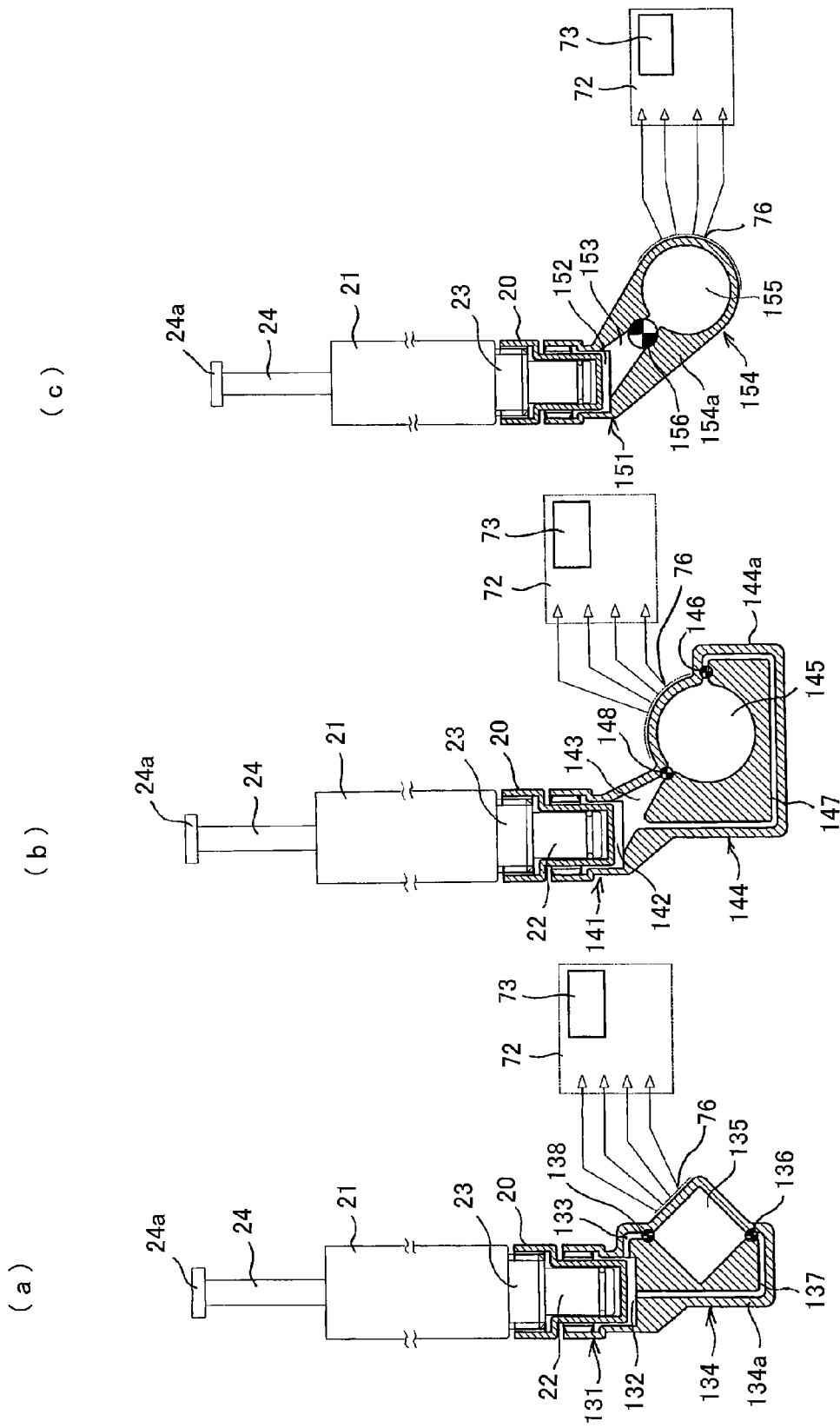
[FIG. 10] is a drawing showing a case where a reaction vessel according to a sixth embodiment to an eighth embodiment of the present invention is connected to a nozzle, and reaction measurement is to be performed.

FIG. 9 shows an example of a reaction vessel 211 according to a fifth embodiment, wherein it is connected to the bottom end section of a nozzle 22 serving as the rotating body of the liquid introducing device 50, via a cap 20, and shows the positional relationship between; a rod lens 75 serving as the irradiation end section of the optical information measuring section, in a case where it has been transported to the reaction measuring position by the liquid introducing device 50, a light reception end section 78 that corresponds to, for example, the end of an optical fiber, and a long and narrow shaped heating body 79 of the heating and cooling section, which has been wrapped around the rod lens 75. In FIG. 9 and FIG. 10, the cap 20, the elastic valve, and the like, have been conceptually shown. In regard to the rod lens 75, to which the heating body 79 has been wrappingly installed, as well as being the irradiation end section, it corresponds to a heating end section.

FIG. 9(a) is a front cross-sectional view showing the reaction vessel 211. The reaction vessel 211 comprises: a storage chamber 212 in which a liquid is storable, that has an opening part; an approximately triangular prism shaped reaction chamber 215 that is communicated with the storage chamber 212 and is formed thinner than the storage chamber 132; and a discharge flow passage 217 that communicates between the storage chamber 212 and the reaction chamber 215. The discharge flow passage 217 and the reaction chamber 215 are formed in a layer form sandwiching the same, and the entirety thereof is provided on a translucent reaction section 214. Reference symbols 213 and 216 of FIG. 9(*a*) denote elastic valves serving as the elastic block members mentioned above, and as a result of pressing by the pressing sections 101 and 102 shown in FIG. 9(*b*), the void is closed, and it is sealable. In regard to the reaction vessel 211 according to the present embodiment, since two openings are provided in the reaction chamber 215 thereof, it corresponds to the fluid circuit.

In regard to the reaction vessel 211, as the rotating body of the liquid introducing device 50, suction and discharge of the fluid is possible, and the inner surface of the upper side of the cap 20 is threaded with the outer surface of the threaded section 23 of a nozzle 22, which is rotatable about the axis thereof, such that it covers the lower end section of the nozzle 22. As a result, contact between the nozzle 22 and the reaction vessel 211 that is to be connected, or with the stored liquid thereof, can be prevented. The outer surface of the cap 20 is threaded, and by threading with the inner surface of the opening part of the reaction vessel 211, the reaction vessel 211 is connected to the nozzle 22. A cylinder (not shown in the drawing) which is communicated with the nozzle 22 and is rotatably provided together with the nozzle 22, is provided on the inner section of the cylindrical element 21, and is rotatably supported on the cylindrical element 21 via a bearing (not shown in the drawing). In order to perform the suction and discharging of the fluid of the nozzle 22, a rod 24 which vertically moves a plunger (not shown in the drawing) that adjusts the pressure within the nozzle 22, is provided within the cylinder. On the upper end of the rod 24, an end section 24*a* which has a larger diameter than the diameter of the rod 24, is provided. The rod 24 which is inserted into the rotatable cylinder, is non-rotatably provided in the nozzle 22 or the cylinder.

In this manner, in the present embodiment, the interval between the threaded section 23 and the cap 20, and the interval between the cap 20 and the opening part of the reaction vessel 211 is connected as a result of threading. Accordingly, it is necessary to thread the threaded portion in the tightening direction by rotation of the nozzle 22 serving as the rotating body.

According to the reaction vessel 211 of the present embodiment, the reaction chamber 215 is provided on the lower side of the storage chamber 212 in a position farther away from the rotation axis than the storage chamber 212, that is to say, the axis of the opening part. Consequently, the liquid that is dispensed into the storage chamber 212 by the dispensing tip by means of the suction and discharging of the nozzle 22, can be introduced into the reaction chamber 215 by the nozzle 22 rotating about the axis thereof, as a result of centrifugal force. When the liquid is introduced into the reaction chamber 215, the air that is present within the reaction chamber 215 is discharged to within the storage chamber 212 through the discharge flow passage 217, and in a case where the reaction chamber 215 is filled with the liquid, it is sealed by pressing the elastic valves 213 and 216. The reaction chamber 215 and the discharge flow passage 217 are provided on a frame 214*a* in which bottomed grooves or depressions have been formed. As shown in FIG. 9(*b*), the opening of the frame 214*a* is blocked by a transparent thin plate or the film 218.

As shown in FIG. 9(*b*), the light reception end section 78, on which pressing sections 101 and 102 that press the elastic valves 213 and 216 have been provided, and the rod lens 75, and the heating body 79, which correspond to an irradiation end section that irradiates excitation light that excites the fluorescent material, are provided such that they sandwich the two large walls of the reaction chamber 215 that have a large area. This light reception end section 78 and this rod lens 75, which has a heating function, are detachably provided with respect to the reaction chamber 215 by means of an opening and closing mechanism 81 shown in FIG. 13.

FIG. 10 shows examples of reaction vessels 131, 141, and 151 according to a sixth embodiment to an eighth embodiment, which are connected to the lower end section of the nozzle 22 serving as the rotating body of the liquid introducing device 50, via the cap 20, and shows the positional relationship between the light reception end section 76 of the optical information measuring section in a case where it has been transported to the reaction measuring position by the liquid introducing device 50. In these cases, the pressing section may be provided not on the light reception end section 76, but, for example, on the rod lens 75 serving as the irradiation end section.

FIG. 10(*a*) is a front cross-sectional view showing the reaction vessel 131 according to the sixth embodiment. The reaction vessel 131 comprises; a storage chamber 132, in which a liquid is storable, that has an opening part, a regular square prismatic reaction chamber 135 that is communicated with the storage chamber 132 and is formed thinner than the storage chamber 132, and a liquid introduction flow passage 133 and a discharge flow passage 137 that communicate between the storage chamber 132 and the reaction chamber 135. The liquid introduction flow passage 133 communicates between the side face of the storage chamber 132 and the upper portion of the reaction chamber 135, and the discharge flow passage 137 communicates between the bottom portion of the reaction chamber 135 and the inner bottom face of the storage chamber 132. Reference symbols 136 and 138 denote elastic valves, which are blockable by pressing.

In regard to the nozzle 22 serving as the rotating body of the liquid introducing device 50, this is as explained in FIG. 9, and the explanation is omitted.

According to the reaction vessel 131 of the present embodiment, the reaction chamber 135 is provided on the lower side of the storage chamber 132 in a position farther away from the rotation axis of the nozzle 22 serving as a rotating body, than the storage chamber 132, that is to say, the axis of the opening part of the storage chamber 132. Consequently, the liquid that is dispensed into the storage chamber 132 by the dispensing tip by means of the suction and discharging of the nozzle 22, can be introduced into the reaction chamber 135 by the nozzle 22 rotating about the axis thereof, as a result of centrifugal force. When the liquid is introduced into the reaction chamber 135, the air that is present within the reaction chamber 135 is discharged to within the storage chamber 132 through the discharge flow passage 137, and in a case where the reaction chamber 135 is filled with the liquid, it is sealed by pressing the elastic valves 136 and 138. The reaction chamber 135, the liquid introduction flow passage 133, and the discharge flow passage 137 are provided on a frame 134*a* to which bottomed grooves or depressions have been formed. The opening of the frame 134*a* is blocked by a film.

FIG. 10(*b*) is a front cross-sectional view showing the reaction vessel 141 according to the seventh embodiment. The reaction vessel 141 comprises; a storage chamber 142, in which a liquid is storable, that has an opening part, a cylindrical reaction chamber 145 that is communicated with the storage chamber 142 and is formed thinner than the storage chamber 142, and a liquid introduction flow passage 143 and a discharge flow passage 147 that communicate between the storage chamber 142 and the reaction chamber 145. The liquid introduction flow passage 143 communicates between the bottom face of the storage chamber 142 and a somewhat upper portion of the reaction chamber 145, and the discharge flow passage 147 connects between a somewhat lower portion of the reaction chamber 145 and the liquid introduction flow passage 143. Reference symbols 146 and 148 denote elastic valves, which are blockable by pressing.

In regard to the nozzle 22 serving as the rotating body of the liquid introducing device 50, this is as explained in FIG. 9, and the explanation is omitted.

According to the reaction vessel 141 of the present embodiment, the reaction chamber 145 is provided on the lower side of the storage chamber 142 in a position farther away from the rotation axis than the storage chamber 142, that is to say, the axis of the opening part of the storage chamber 142. Consequently, the liquid that is dispensed into the storage chamber 142 by the dispensing tip by means of the suction and discharging of the nozzle 22, can be introduced into the reaction chamber 145 by the nozzle 22 rotating about the axis thereof, as a result of centrifugal force. When the liquid is introduced into the reaction chamber 145, the air that is present within the reaction chamber 145 is discharged to within the storage chamber 142 through the discharge flow passage 147, and in a case where the reaction chamber 145 is filled with the liquid, it is sealed by pressing the elastic valves 146 and 148. The reaction chamber 145, the liquid introduction flow passage 143, and the discharge flow passage 147 are provided on a frame 144a in which bottomed grooves or depressions have been formed. The opening of the frame 214a is blocked by a film FIG. 10(c) is a front cross-sectional view showing the reaction vessel 151 according to the eighth embodiment. The reaction vessel 151 comprises; a storage chamber 152, in which a liquid is storable, that has an opening part, a regular square prismatic reaction chamber 155 that is communicated with the storage chamber 152 and is formed thinner than the storage chamber 152, and a liquid introduction flow passage 153 that communicates between the storage chamber 152 and the reaction chamber 155. The liquid introduction flow passage 153 communicates between the bottom face of the storage chamber 152 and the upper portion of the reaction chamber 155. Reference symbol 156 denotes an elastic valve, which is blockable by pressing. In regard to the reaction vessel 151 according to the present embodiment, since the reaction chamber 15 has only one opening, it corresponds to the fluid storage section. On the other hand, in regard to the reaction vessels 131 and 141, since the reaction chambers 135 and 145 respectively have two openings, they correspond to fluid circuits.

In regard to the nozzle 22 serving as the rotating body of the liquid introducing device 50, this is as explained in FIG. 9, and the explanation is omitted.

According to the reaction vessel 151 of the present embodiment, the reaction chamber 155 is provided on the lower side of the storage chamber 152 in a position farther away from the rotation axis of the rotating body than the storage chamber 152, that is to say, the axis of the opening part of the storage chamber 152. Consequently, the liquid that is dispensed into the storage chamber 152 by the dispensing tip by means of the suction and discharging of the nozzle 22, can be introduced into the reaction chamber 155 by the nozzle 22 rotating about the axis thereof, as a result of centrifugal force. When the liquid is introduced into the reaction chamber 155, the air that is present within the reaction chamber 155 is discharged to within the storage chamber 152 through the same liquid introduction flow passage 153, and in a case where the reaction chamber 155 is filled with the liquid, it is sealed by pressing the elastic valve 156. The reaction chamber 155 and the liquid introduction flow passage 153 are provided on a frame 154a to which bottomed grooves or depressions have been formed. The opening of the frame 154a is blocked by a film.

Figure 11:
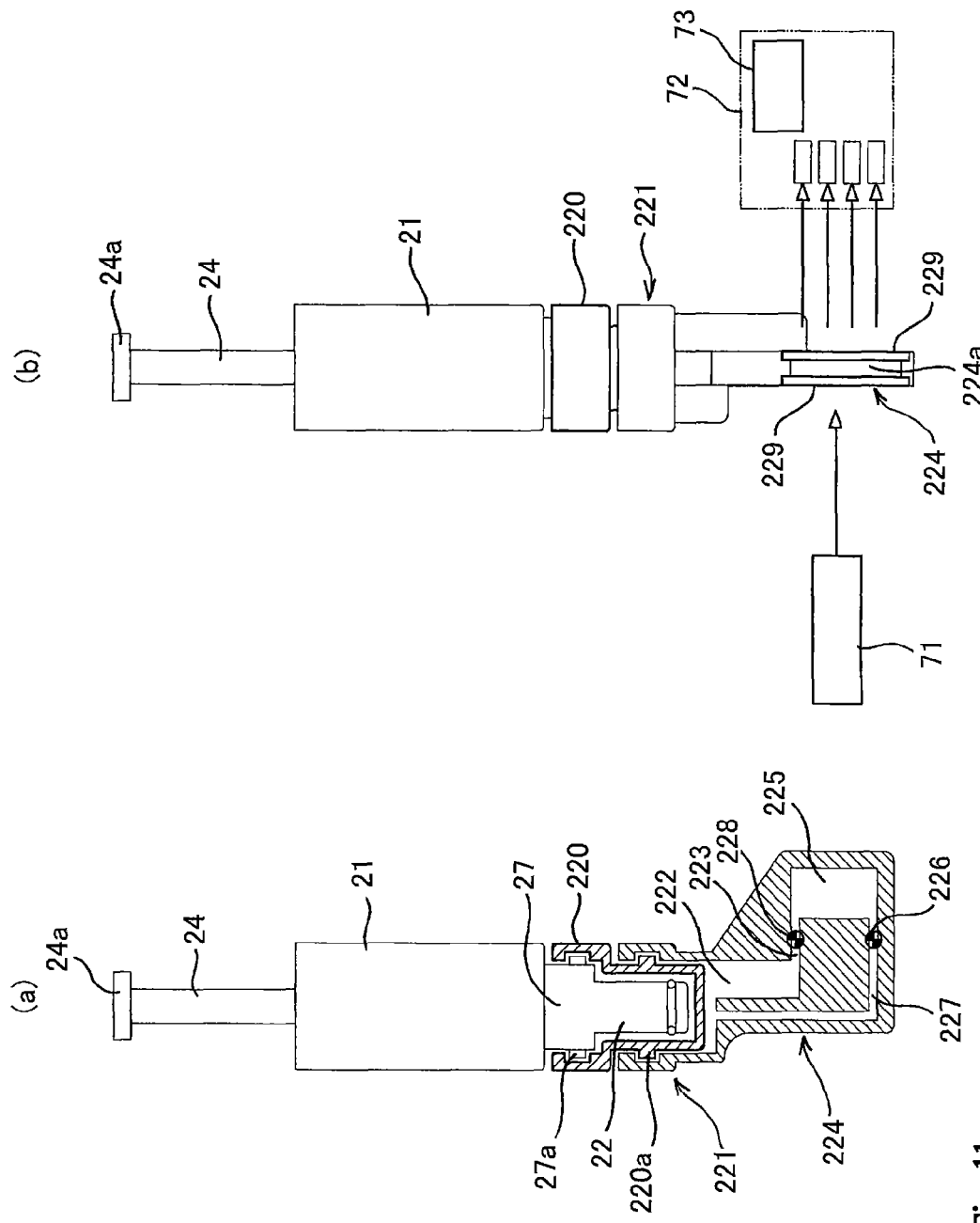
[FIG. 11] is a drawing showing a reaction vessel according to a ninth embodiment of the present invention.

Next, a reaction vessel 221 according to a ninth embodiment is explained based on FIG. 11.

FIG. 11(a) is a front cross-sectional view of the reaction vessel 221. The reaction vessel 221 comprises; a storage chamber 222, in which a liquid is storable, that has an opening part, an approximate square prismatic reaction chamber 225 that is communicated with the storage chamber 222 via an introduction flow passage 223 and as a whole is formed thinner than the storage chamber 222, and a liquid introduction flow passage 223 and a discharge flow passage 227 that communicate between the storage chamber 222 and the reaction chamber 225. Consequently, the reaction vessel 221 corresponds to the fluid circuit. The liquid introduction flow passage 223, the discharge flow passage 227, and the reaction chamber 225 are formed in a layer form in which they are sandwiched from the front and back by a transparent thin plate or a film 229, and the entirety thereof is provided on a translucent reaction section 224. Reference symbols 228 and 226 of FIG. 11 denote, for example, blocking positions at which elastic valves, which are the elastic block members mentioned above, are provided, and as a result of pressing by means of the pressing section shown in FIG. 9(b), the void is closed, and is blockable.

In regard to the reaction vessel 221, as the rotating body of the liquid introducing device 50, suction and discharge of the fluid is possible, and a cap 220 formed from an elastic body, such as rubber, is installed on the nozzle 22, which is rotatable about the axis thereof, such that it covers the lower end section of the nozzle 22 by means of the inner surface of the upper side of the cap 220 engaging a protrusion 27a provided on the outer face of the installation section 27 of the nozzle. As a result, contact between the nozzle 22 and the reaction vessel 211 that is to be connected, or with the stored liquid thereof, can be prevented. On the other hand, the reaction vessel 221 is connected to the cap 220 as a result of engagement with the inner face of the opening part of the reaction vessel 221. A cylinder (not shown in the drawing) which is communicated with the nozzle 22 and is rotatably provided together with the nozzle 22, is provided on the inner section of the cylindrical element 21, and is rotatably supported on the cylindrical element 21 via a bearing (not shown in the drawing). In order to perform the suction and discharging of the fluid of the nozzle 22, a rod 24 which vertically moves a plunger (not shown in the drawing) that adjusts the pressure within the nozzle 22, is provided within the cylinder. On the upper end of the rod 24, an end section 24a which has a larger diameter than the diameter of the rod 24, is provided. The rod 24 which is inserted into the rotatable cylinder, is non-rotatably provided in the nozzle 22 or the cylinder.

Figure 12:
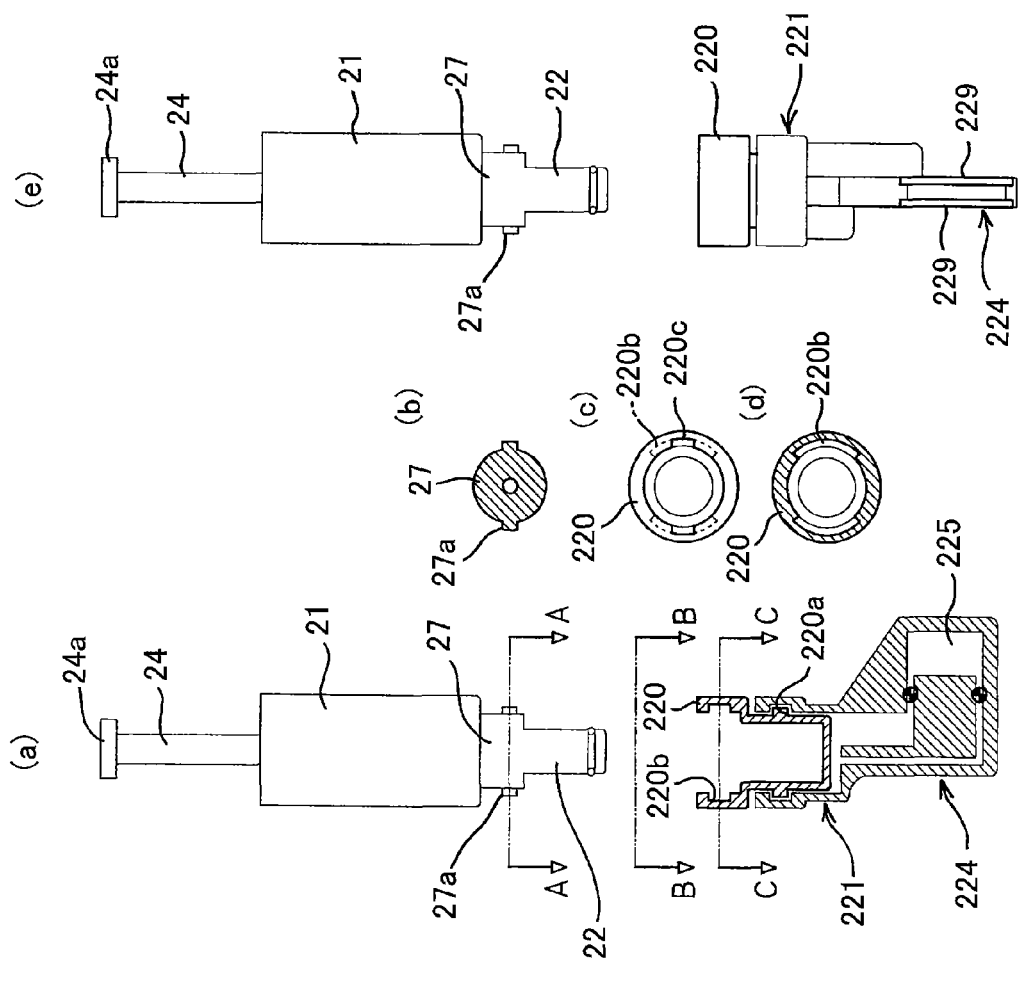
[FIG. 12] is a cross-sectional view and an exploded view of a reaction vessel according to the ninth embodiment of the present invention.

In FIG. 12(a) is shown a partial cross-sectional front view of a state of the reaction vessel 221 fitted with the cap 220, which is in a state where it has been detached from the installation section 27. Furthermore, a cross-sectional view along line AA thereof is shown in FIG. 12(b), a view along line BB is shown in FIG. 12(c), and a cross-sectional view along line CC is shown in FIG. 12(d). Furthermore, FIG. 12(e) shows, as shown in FIG. 12(a), a side view of the reaction vessel 221 fitted with the cap 220, which is in a state where it has been detached from the nozzle 22. The protrusions 27a provided on the installation section 27 of the nozzle 22 are inserted from a notch 220c provided on the upper end of the cap 220 that is formed somewhat larger than the protrusions 27a into side grooves 220b, which have a fixed central angle, provided on the cap 220, and engage the side grooves 220b such that they are sandwiched. On the other hand, in regard to the annular protrusion 220a provided on the outer face of the cap 220, it is inserted and engaged with the annular side groove provided on the inner wall of the storage chamber 222. The outer face of the lower side of the cap 220, which is formed by the elastic body, bonds to the inner face of the upper side of the storage chamber 222 of the reaction vessel 211, and the opening part of the reaction vessel 221 is blocked. Consequently, it is possible to prevent liquid leakage and gas leakage.

In this manner, in the present embodiment, the interval between the installation section 27 and the cap 220 is connected by engagement, and the interval between the lower side outer face of the cap 220 and the opening part of the reaction vessel 221 is bonded. Accordingly, by means of the rotation of the nozzle 22 serving as the rotating body, the reaction vessel 221 is rotated.

According to the reaction vessel 221 of the present embodiment, the reaction chamber 225 is provided on the lower side of the storage chamber 222 in a position farther away from the rotation axis than the storage chamber 222, that is to say, the axis of the opening part. Consequently, the liquid that is dispensed into the storage chamber 222 by the dispensing tip by means of the suction and discharging of the nozzle 22, can be introduced into the reaction chamber 225 by the nozzle 22 rotating about the axis thereof, as a result of centrifugal force. When the liquid is introduced into the reaction chamber 225, the air that is present within the reaction chamber 225 is discharged to within the storage chamber 222 through the discharge flow passage 227, and in a case where the reaction chamber 225 is filled with the liquid, it is sealed by pressing the elastic valves at the blocking positions 226 and 228. The reaction chamber 225, a portion of the storage chamber 222, and the discharge flow passage 227 are provided on a frame 224a in which a hole has been formed.

Figure 13:
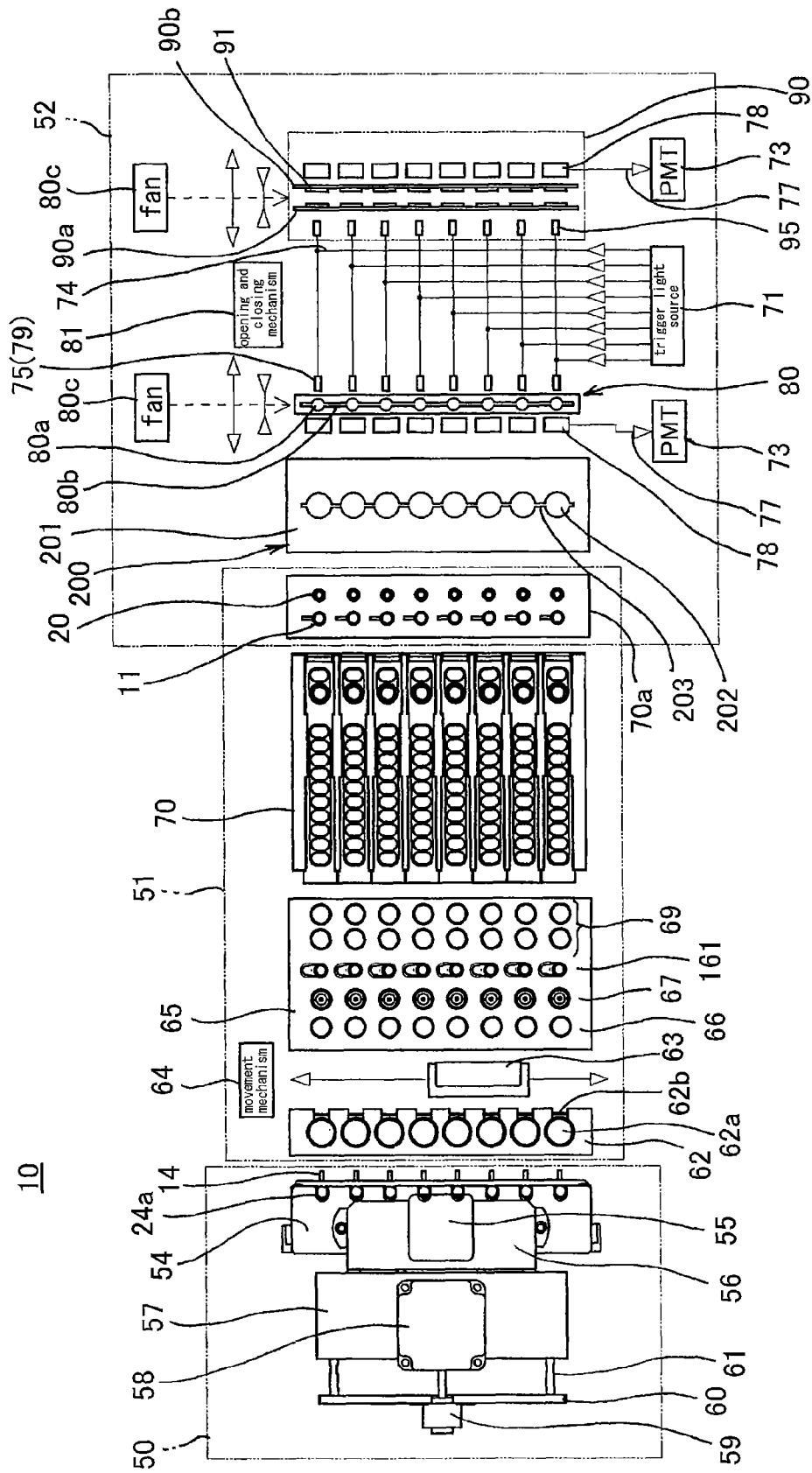
[FIG. 13] is an overall view showing a reaction measurement processing system according to an embodiment of the present invention.

FIG. 13 is a concept diagram showing an entire reaction measurement processing system 10 according to an embodiment of the present invention.

The reaction measurement processing system 10 comprises; the liquid introducing device 50, a liquid treatment area 51 in which measurement preparations such as homogenization, extraction, reaction, transportation, and thinning of suspension liquids containing specimens based on various specimens, test reagents, and the like, are performed, and a reaction measuring area 52 that obtains optical signals for executing real time PCR with respect to a solution that is sealed in the reaction chamber of the reaction vessel.

Figure 14:
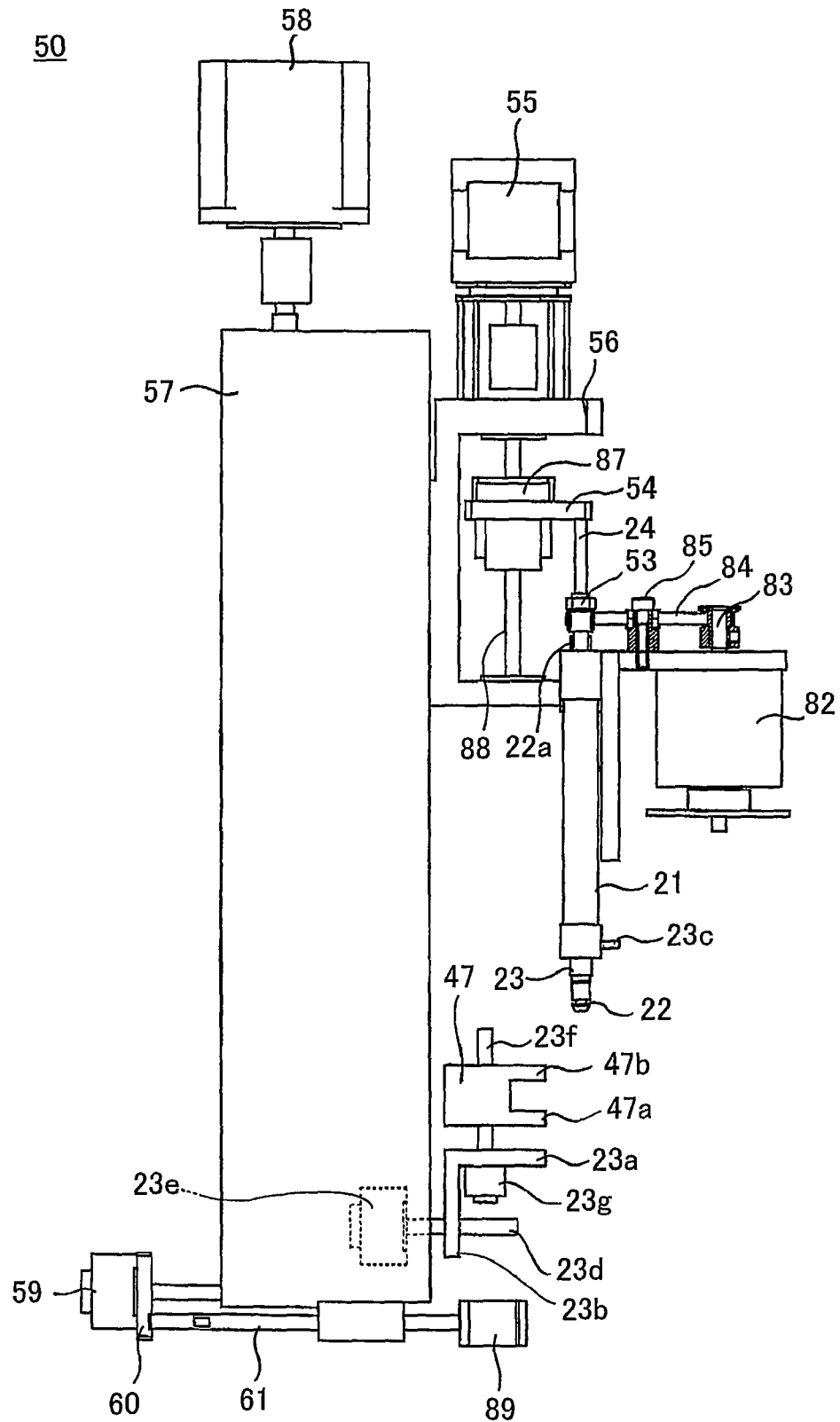
[FIG. 14] is a side view showing a liquid introducing device according to an embodiment of the present invention.

As shown in FIG. 13 or FIG. 14, the liquid introducing device 50 has a plurality of (in this example, eight) nozzles 22 which are rotating bodies, and it is a device in which by connecting various elements on the threaded sections 23 which have been provided in a slightly more upper section than the ends of the nozzles 22, various processes, for example, thinning or capillaration of the liquid, homogenization of the suspension liquid, dispensing of the liquid, transportation, removal of impurities, extraction of the target material, stirring, washing, and the like, are possible. Here, connection includes installation, threading, engagement, engaging insertion, accommodation, and the like.

The liquid introducing device 50 comprises, as shown in FIG. 13 and FIG. 14, a plurality of (in this example, eight) nozzles 22 which are rotating bodies, nozzles 22 that are covered by caps 20 and are provided with a suction and discharging part, threaded sections 23 that are provided in a slightly more upper section than the lower ends of the nozzles 22, that connect to the caps 20 by threading, and rods 24 for sliding the plungers (not shown in the drawing) within the cylinders 22a that are communicated with the nozzles 22. Furthermore, the liquid introducing device 50 comprises, in order to rotate the eight nozzles 22 and the cylinders 22a about the axis center thereof, synchronous pulleys 53 provided on the same center, a motor 82 for rotating the eight nozzles 22 and the cylinders 22a, a motor shaft 83 of the motor 82, and a belt 84 that spans the eight synchronous pulleys 53 and the motor shaft 83. Reference symbol 85 denotes a roller for adjusting the tension of the belt 84. Here, in FIG. 11, the motor 82, the motor shaft 83, the belt 84, and a tension adjustment rotor 85 have been omitted to improve viewability. Furthermore, in FIG. 12, the connection of the reaction vessel 11, and the like, has been omitted.

The eight rods 24 are installed by hooking end sections 24a that protrude in the radial direction with a larger shape than the diameter of the rods 24, to eight notched sections provided on the edge of a drive plate 54, and the drive plate 54 is connected to nut sections 87 that are threaded to ball screws 88. The rods 24 are always biased in the downward direction by a spring that is provided on the cylinders 22a. As a result, in a case where the rods 24 move in the upward direction, they are raised by the nut sections 87, but when they descend in the downward direction, they descend by the spring force, rather than by the nut sections 87. The ball screws 88 are rotationally driven by a motor 55 provided on a supporting member 56, which has a letter-U shaped cross-section, and as a result, the drive plate 54 and the eight rods 24 simultaneously move vertically.

In FIG. 14, reference symbol 23a denotes a tip removal plate for removing the connected dispensing tips. The tip removal plate 23a comprises a supporting section 23b that extends in the downward direction, and is threaded with a ball screw 23d, and the ball screw 23d is rotationally driven by means of a motor 23e. Consequently, by means of the rotation of the motor 23e, the tip removal plate 23a is advancable and retractable with respect to the nozzle 22. The motor 23e, the ball screw 23d, and accordingly, the tip removal plate 23a, are vertically movable by means of a vertical movement mechanism configured by a ball screw mechanism provided within a chassis 57.

An engaging block 47 provided with the cap engaging sections 47a and 47b is threaded to a ball screw 23f. By means of the rotation of the motor 23g, it is possible for the cap engagement sections 47a and 47b to approach or separate with respect to the tip removal plate 23a.

Reference symbol 23c denotes a flow passage for connection to a pressure sensor.

The supporting member 56 is vertically movable independent of the tip removal plate 23a by a vertical movement mechanism that is configured by a ball screw mechanism provided within an enclosure 57. A motor 58 rotationally drives the ball screw. A magnetic force device comprising; a motor 59 for moving a magnet 89 which is for applying or removing a magnetic field from the outside of the dispensing tip connected to the nozzles 22 to within the tip, a horizontal rod 60, a rod 61, and the magnet 89, is provided on the underside of the enclosure 57, and moves the magnet 89 left and right in the figure.

The liquid introducing device 50 is provided such that it is suspended from the upper side, and is movably provided as a result of an X axis Y axis movement mechanism that utilizes a linear movement mechanism (not shown in the drawing), such that it covers all regions of the reaction measurement processing system 10 and other necessary regions.

The liquid treatment area 51 of FIG. 13 comprises; a cartridge vessel 62 having eight specimen storage wells 62a that store the suspensions in which the specimens are suspended, a matrix form vessel 65 having five columns by eight rows, eight cartridge vessels 70 for storing the various test reagents and materials necessary for executing real time PCR, or treatment products, and a holding rack 70a for retaining the eight reaction vessels 11 and the caps 20.

Furthermore, on the specimen storage wells 62a, barcodes 62b are respectively applied showing the information relating to the specimens thereof. The barcodes 62b are read by moving a barcode reading section 63 which reads the barcode, so as to scan the barcode. Reference symbol 64 denotes a movement mechanism of the barcode reading section 63.

The matrix form vessel 65 retains; a column of filter built-in tips 66 for removing impurities by suction and discharging of the liquid following the homogenization process of the suspension containing the specimen, a column of dispensing tips 67, a column of vessels 161 in which filter built-in vessels 161 (or column connection vessels 171) for homogenizing and removing the impurities from the suspension containing the specimen as a result of rotation are arranged, and a column of wells 69 that store the test reagents necessary for PCR.

FIG. 15(a) shows a usage state of a case where the filter built-in tip 66 which is retained on the matrix form vessel 65 of the processing area, is used by connecting it to the liquid introducing device 50.

The filter built-in tip 66 is used by engaging it on the dispensing tip 67. The dispensing tip 67 comprises a flange 67a which is provided on the upper side, a storage section 67b which stores the liquid, an engaging section 67c which is provided on the underside of the storage section 67b and engages the opening part of the filter built-in tip 66, and a small diameter section 67d that is communicated with the storage section 67b, on the underside of the storage section 67b, and which has a thinner diameter than the storage section 67b and has a liquid suction and discharging port.

The filter built-in tip 66 comprises a flange 66a provided on the upper end, a storage chamber 66b that has an opening part which is engagable by means of the engaging section 67c of the dispensing tip, in which the liquid is storable, and with a built-in filter 100, and a small diameter section 66c that is provided on the underside of the storage chamber 66b that is communicated with the storage chamber 66b and that has a smaller diameter than the storage chamber 66b. It is necessary for the filter 100 to have a bore diameter corresponding to the target to be filtered.

Figure 15:
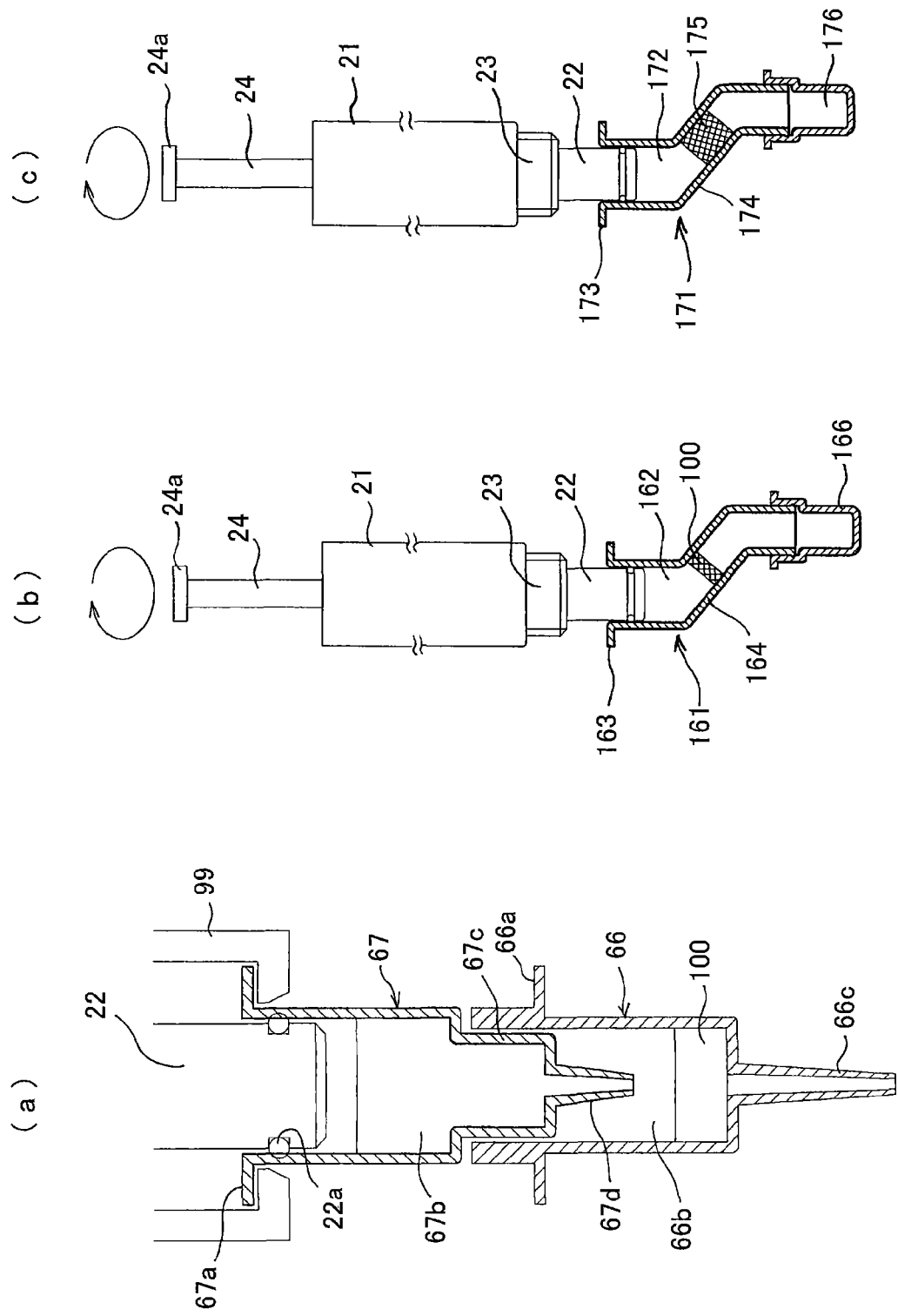
[FIG. 15] is a drawing showing a filter built-in tip, a filter built-in vessel, and a column connection vessel according to an embodiment of the present invention.

In order to remove the impurities, or separate the target material from within the suspension using the filter built-in tip 66, then as shown in FIG. 15, the end sections of the nozzles 22 provided on the liquid introducing device 50 are engaged with the upper end opening part of the dispensing tips 67, and a connection member 99 provided on the liquid introducing device 50, and the flanges 67a provided on the upper ends of the dispensing tips 67 are engaged and connected. Next, by engaging the opening part of the storage chamber 66b of the filter built-in tip 66 with the engaging section 67c of the dispensing tip 67, the filter built-in tip 66 is connected. As a result of suction or discharging of the liquid in such an engaged state such that the liquid passes through the filter 100, the impurities or the target material within the liquid are separated.

Furthermore, instead of connecting the filter built-in tip 66, as shown in FIG. 15(b) or in FIG. 15(c), it is acceptable if the impurities or the target material in the liquid is separated by using the filter built-in vessel 161 or the column connection vessel 171 retained in the matrix form vessel 65 of the liquid treatment area 51, and by utilizing the rotation of the liquid introducing device 50. The filter built-in vessel 161 comprises a cylindrical storage chamber 162 in which liquid is storable, and that has an opening part to which the lower end section of the nozzle 22 is connectable, a filter chamber 164 that is partitioned by a filter 100 that has a predetermined pore diameter and extends in the diagonally downward direction from the storage chamber 162, and a housing chamber 166 that is communicated with the filter chamber 164 and is installed such that it is detachable with respect to the filter chamber 164. Reference symbol 163 denotes a flange used for removal by the tip removal plate 23a.

In regard to the present filter built-in vessel 161, the axis of the opening part, to which the bottom end section of the nozzle 22 is connectable, becomes the rotation axis. Furthermore, the filter chamber 165 is positioned farther away with respect to the axis than the storage chamber 162, and furthermore, the housing chamber 166 is positioned farther away with respect to the axis than the filter chamber 165. Consequently, as a result of the rotation of the nozzle 22, the filter built-in vessel 161 connected to the same rotates, and as a result, the liquid stored in the storage chamber 162 reaches the housing chamber 166 through the filter chamber 164 as a result of the rotation. In regard to the filter built-in vessel 161, the line that connects the storage chamber 162, the depression 163, the filter chamber 164, and the housing chamber 166 creates an approximate acute angle with the axis.

FIG. 15(c) shows the column connection vessel 171. The column connection vessel 171 comprises a cylindrical storage chamber 172 in which liquid is storable, and that has an opening part to which the lower end section of the nozzle 22 is connectable, a column 174 that is communicated with the storage chamber 172 and in which a solid 175 that has a predetermined adsorptivity is stored, and a housing chamber 176 that is communicated with the column 174 and is installed such that it is detachable with respect to the column 174. Reference symbol 173 denotes a flange used for removal by the tip removal plate 23a.

In regard to the present column connection vessel 171, the axis of the opening part, to which the bottom end section of the nozzle 22 is connectable, becomes the rotation axis. Furthermore, the column 174 is, such that it creates an acute angle in the downward direction with respect to the rotation axis, provided such that it extends in the diagonally downward direction thereof with respect to the storage chamber 172, and the column 174 is provided in a position farther away with respect to the rotation axis than the storage chamber 172. Consequently, as a result of the rotation of the nozzle 22 serving as the rotating body, the column connection vessel 171 that is connected to the lower end section of the nozzle 22 rotates, and as a result, the liquid stored within the storage chamber 172 temporarily enters the depression 173, is introduced into the column 174 through the depression 173, and eventually reaches the housing chamber 176.

In FIG. 15(b) or FIG. 15(c), if a depression is provided in the bottom section of the storage chambers 162 and 172, and the filter chamber 164 or the column 174 is communicated via the depression, then even if there is a small quantity of liquid, the liquid can be efficiently moved to the filter chamber 164 or the column 174 by temporarily storing the liquid in the depression.

Furthermore, returning to FIG. 13, the reaction measuring area 52 comprises; a static PCR unit 80 that retains the eight reaction vessels 11 (31, 41, 111, 131, 141, 151, 211, 221) to which the target vessels have been introduced and sealed within the reaction chambers 15 (or 33, 41*a*, 115, 135, 145, 155, 215, 225) such that temperature controls and optical measurements are possible, or a dynamic PCR unit 90 that vertically movably inserts such that temperature controls and optical measurements are possible. The static PCR unit 80 and the dynamic PCR unit 90 are switchingly utilized by means of a switch. In regard to the static PCR unit 80, in order to heat or cool the reaction chamber 15 of the reaction vessel 11 retained in a static state therein, a rod lens 75, in which light reception end sections 78 and wire form heating bodies 79 are wrapped around, is provided such that it is made to sandwich the reaction chambers 15 from both sides along the thickness direction thereof. These light reception end sections 78 and the rod lens 75 are approachably and separatably provided with respect to the reaction chambers 15. These rod lenses 75 correspond to irradiation end sections of the optical information measuring sections that in a case where a fluorescent material is used as a marker material within the reaction chambers 15, irradiates excitation light for obtaining optical information from the marker material onto the irradiation positions inside the reaction chambers 15. Furthermore, it comprises a trigger light source 71 that supplies the excitation light to the rod lenses 75 of the irradiation end sections through optical fibers 74, and a photomultiplier that receives the light from the reaction chambers 15 at the light reception end sections 78 and converts the light received through the optical fibers 77 into an electrical signal.

Figure 21:
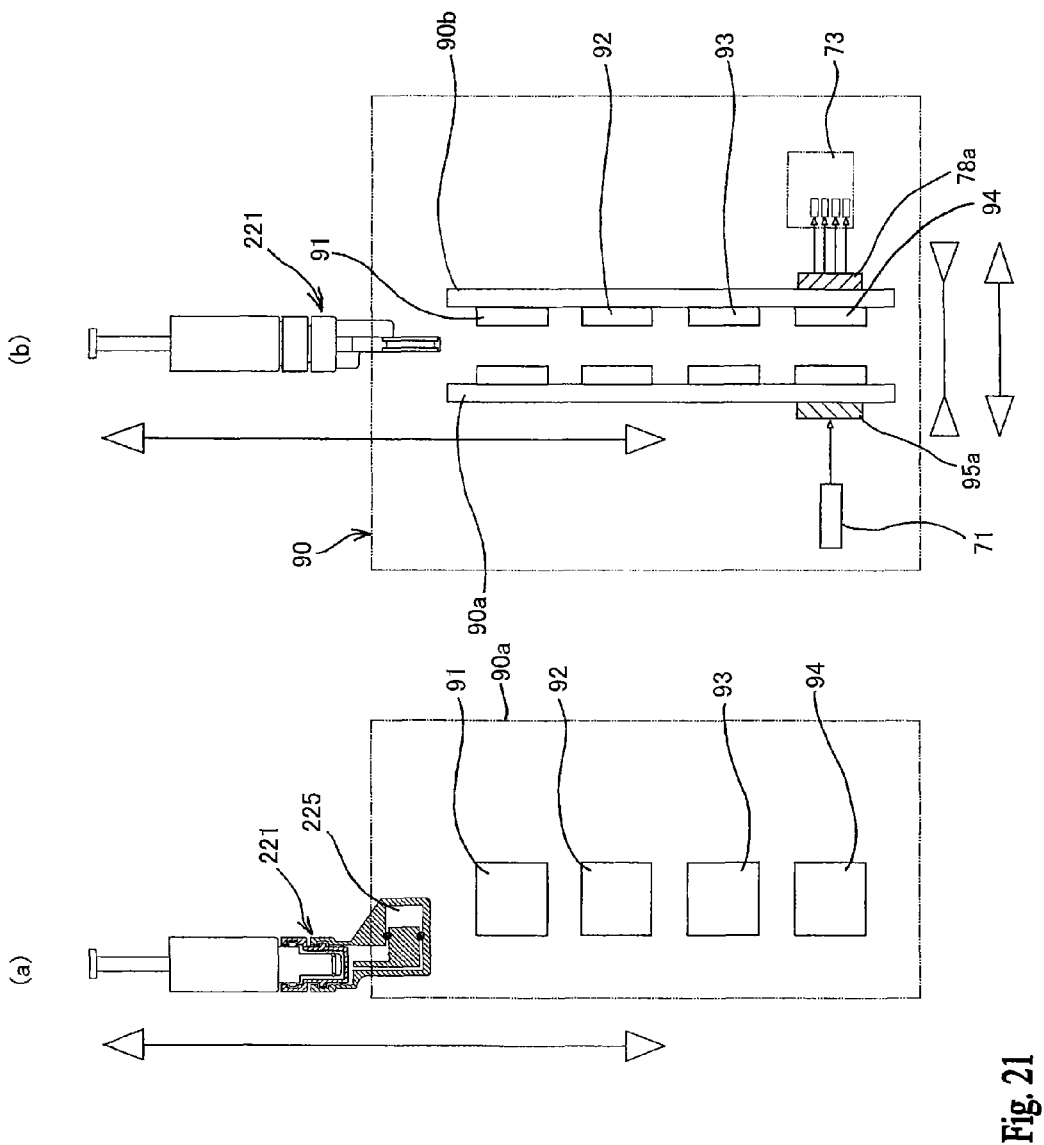
[FIG. 21] is a drawing showing a PCR unit according to an embodiment of the present invention.

On the other hand, in regard to the dynamic PCR unit 90, as shown in FIG. 13 or FIG. 21, two movable walls 90*a* and 90*b* that are provided such that they sandwich the reaction chamber 15 of the reaction vessel 11 along the thickness direction thereof, and regions 91, 92 and 93 at which the movable walls 90*a* and 90*b* are provided and at which a heating end section or a cooling end section is provided for heating or cooling the reaction chamber 15, are arranged in the vertical directions for each reaction vessel 11. Furthermore, at the lowermost section of the row along these regions 91, 92 and 93, there is provided a region 94 at which a light reception end section for optical information measurement is positioned for each reaction vessel 11. On the outside of the movable walls 90*a* and 90*b*, light reception end sections 78 are positioned at the regions 91 to 93, the rod lens 75 for irradiating excitation light is positioned at the region 94, and by fixingly providing them to the movable walls 90*a* and 90*b*, they are provided such that approaching and separating with respect to the reaction chamber 15 is possible. The region 94 is transparently formed, and a fan 80*c* that blows air in a direction along the arrangement of the reaction vessels 11 is provided for the PCR units 80 and 90. By providing a cooling air jetting section in the spaces between the regions 91, 92 and 93 shown in FIG. 21, at which the heating end section or the cooling end section has been provided, the shifting of temperature in a case where the temperature that is set between regions is lowered can be smoothly performed. The opening and closing of the light reception end sections 78, the rod lens 75 (79) of the static PCR unit 80, and the movable walls 90*a* and 90*b* of the movable PCR unit 90 are performed by an opening and closing mechanism 81.

In the dynamic PCR unit 90, since the temperature control and the control of the measurement of the optical information can be replaced by the movement between the regions, the control and the processing is simplified. Furthermore, compared to a case where the temperature of a heating body or a cooling body with a large heat capacity is raised or lowered, since the temperature can be instantaneously changed by means of movement to a different temperature region, the temperature responsiveness with respect to instructions is high, and a highly accurate and fine temperature control can be performed. Consequently, it can be used in processing where accuracy is demanded.

In regard to the reaction vessels 11, they are respectively inserted into the eight holes 80*a* of the PCR unit 80 as shown in FIG. 1(*b*), FIGS. 7(*c*) to 7(*e*), FIG. 9, or FIG. 13, in a state where the opening parts 13 thereof are covered by the caps 20, and are further connected to the nozzles 22, supported by the stepped portions of the flange 12*a* of the opening parts 13, and the reaction section 14 is inserted into the slit 80*b* of the PCR unit 80. On the underside of the PCR unit 80, along the direction of the reaction section 14 thereof, the light reception end section 78 is provided on one wall side thereof, that is to say, the wall side to which the film 18 has been provided, and on the other wall side, the rod lens 75, to which the heating body 79 has been wrapped around, is provided.

The light reception end section 78 and the rod lens 75 are simultaneously or individually detachably provided with respect to the reaction sections 14 by means of an opening and closing mechanism 81. On the light reception end section 78, which is on the side face side on which the films 18 of the reaction sections 14 have been provided, pressing sections 101 and 102 for pressure deforming the elastic valve 16*a* of the film 18 are provided such that they protrude in the normal direction of the side surface of the tabular light reception end section 78, which is the end of a fiber bundle, at points corresponding to the elastic valve 16*a* and the hole section 17*b*, which are the blocking positions. Furthermore, the heating and cooling section comprises a fan 80*c* as a cooling end section. The fan 80*c* is able to blow air along the direction in which the eight reaction vessels 11 have been arranged. For example, in a case where the rod lens 75, to which the heating body 79 has been wrapped around, has been separated from the reaction vessels, by sending in air for dissipating the heat of the reaction chambers, heat control can be performed with good efficiency. When the reaction vessels 11 are installed on the PCR unit 80, the light reception end section 78 and the rod lens 75 are moved to positions farther away from the reaction section 14 by means of the opening and closing mechanism 81, and when the heating and cooling is performed, it is performed in a state where the light reception end section 78 and the rod lens 77 are adjacent or in contact with the reaction section 14. The temperature control for the light reception end section 78 and the heating body 79 is performed by setting; the magnitude of an electrical current applied to the light reception end section 78 and the heating body 79, the distance of the rod lens 75 with respect to the reaction chamber 15, or the timing, strength, and the like, of the ventilation by the fan 80*c*, by program control from an information processing device (not shown in the drawing).

Furthermore, an optical information measuring section for measuring the optical information within the reaction chambers 15, is provided on the reaction measuring area 52. Here, supposing a case where the target material for which the quantity within the reaction chambers 15 is to be measured, is labeled by various fluorescent materials, as shown in FIG. 1(*b*), the optical information measuring section comprises; rod lenses 75 as irradiation end sections for irradiating the eight reaction sections 14, a trigger light source 71 for irradiating excitation light, and in FIG. 1(*c*), it comprises a light receiving section 72 having light reception end sections 78 for receiving the emitted light within the reaction sections 14 at the fixed light reception positions with respect to each of the eight reaction sections 14, that is to say, at the large wall that has the largest inner area amongst the walls that enclose the reaction chambers 15, and a photomultiplier 73 that converts the received light at the light reception end sections 78 into an electrical signal. In the same manner as FIG. 1(c), in FIG. 9(a) or FIG. 10, the rod lens 75, which is the irradiation end section and to which a heating body 79 has been wrapped around, is provided on the wall with the largest area, and the light reception end sections 76 are provided on the wall with the smallest area. However, by providing the rod lens 75, which is the irradiation end section, and the light reception end sections 76 on the same wall, the configuration can be simplified. Furthermore, the rod lens 75 and the rod lens 75, which is the irradiation end section, can be provided on oppositely facing walls.

Figure 16:
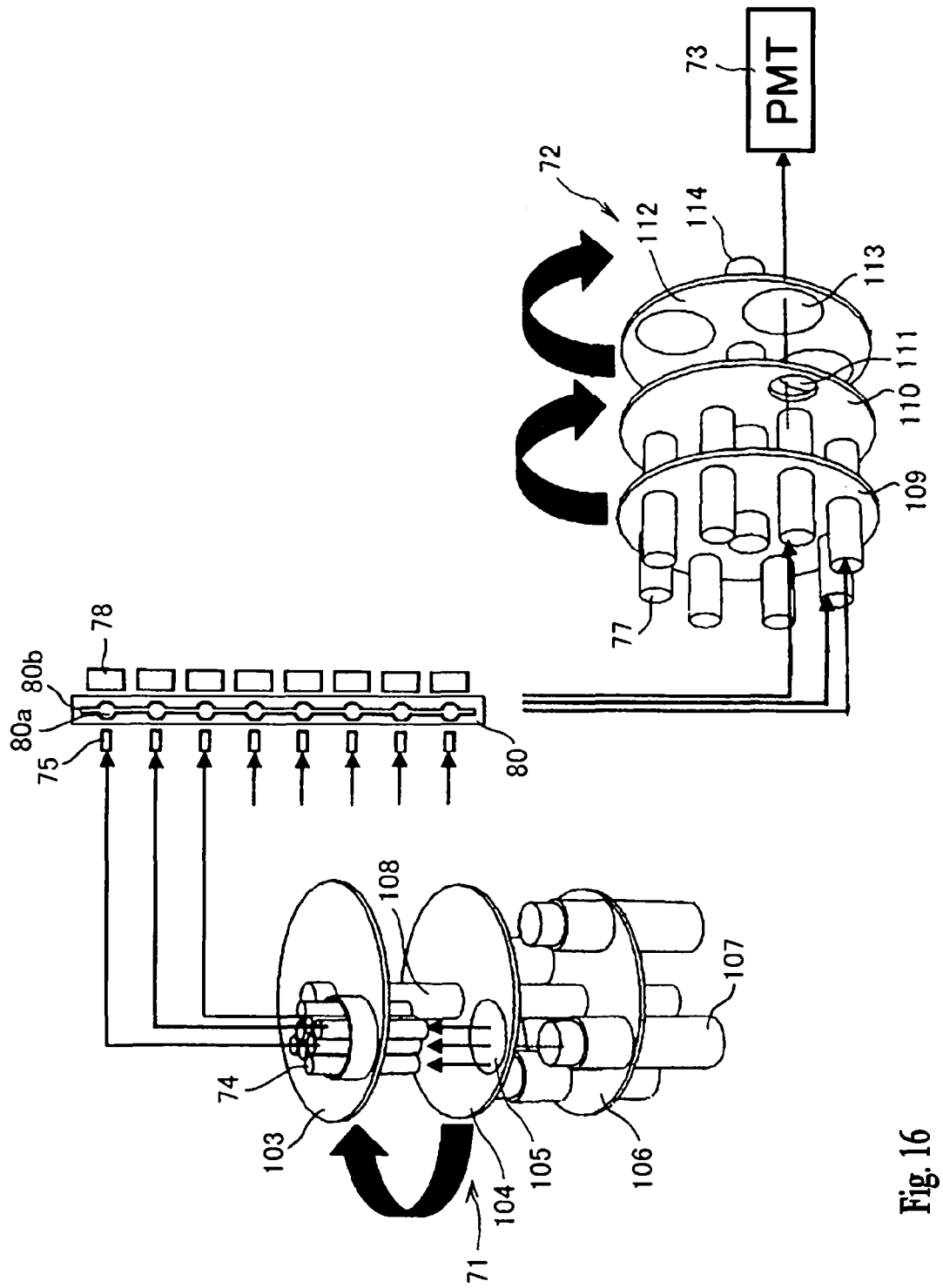
[FIG. 16] is a drawing showing an example of a trigger light source and a light receiving section according to an embodiment of the present invention.

FIG. 16 shows a specific example of the trigger light source 71 and the light receiving section 72. The trigger light source 71 comprises; a rotating plate 103 which supports a bundle of optical fibers 74 that extend to the irradiation end sections of the eight reaction sections 14, a rotating plate 104 to which an optical lens 105 has been fitted into a hole that has been pierced in a location corresponding to the bundle of optical fibers 74, a supporting plate 106 onto which optical fibers 107 which introduce laser light from laser light sources (not shown in the drawing) that emit laser light having a plurality of wavelength types (four types in this example), are arranged at equal space intervals around the circumference along the traveling path of the optical lens 105, and a shaft 108 that rotatably supports the rotating plate 103 and the rotating plate 104 in a state where they are connected, while supporting the supporting plate 106 such that it becomes unrotatable. According to the trigger light source 71, the lights from the four types of light sources which generate laser light having a plurality of wavelength types, are temporally switched, and light can be simultaneously irradiated in the eight reaction chambers 15 at the irradiation end sections. Hence the trigger light source 71 has a light source selection section. The rod lens 75 is provided on the end sections of the optical fibers 74.

The light receiving section 72 comprises; a supporting plate 109 that supports eight optical fibers 77 which extend to the light reception end sections 78 of the eight reaction chambers 15, such that they are arranged at fixed space intervals, a rotating plate 110 in which a hole 111 with an area corresponding to the diameter of the optical fibers 77 has been pierced on the circumference corresponding to the arrangement positions of the optical fibers 77 of the supporting plate 109, a rotating plate 112 that is rotatably provided independently of the rotating plate 110 on which a plurality of types (four types in this example) of filters 113 have been arranged, and a shaft 114 that unrotatably supports the supporting plate 109, and independently rotatably supports the rotating plate 110 and the rotating plate 112. Hence this light receiving section 72 corresponds to a light reception position selection section and an optical filter selection section. The selection of the optical fibers 77 from the light reception end sections 78 corresponds to a light reception position selection section.

According to the optical information measuring section of the present embodiment, by rotating the trigger light source 71 by a predetermined angle at a time in a state where the rotating plate 103 and the rotating plate 104 are connected, and by intermittently rotating the four types of light sources at a fixed time interval, they are simultaneously irradiated one type at a time into the eight reaction chambers 15 of the reaction vessels. Then, the fluorescence excited in the reaction chambers 15 of the reaction vessels 11 are introduced from the light reception end section 76 at the wall of the reaction chambers 15 with a narrow area, to the light receiving section 72 via the optical fiber 77. Then, the rotating plate 110, during the persistence time of fluorescence during the irradiation of the one type of excitation light, sequentially leads the light from the reaction chambers of the eight reaction vessels 11 to the rotating plate 112 by intermittently rotating the rotating plate 110 by one revolution, and furthermore, while the fluorescence from a single reaction vessel 11 is being received, by rotating the rotating plate 112 by one revolution, the light is introduced to the PMT 73 by sequentially passing it through the four types of optical filters 113. This operation is sequentially performed with regard to the four types of excitation light.

Figure 17:
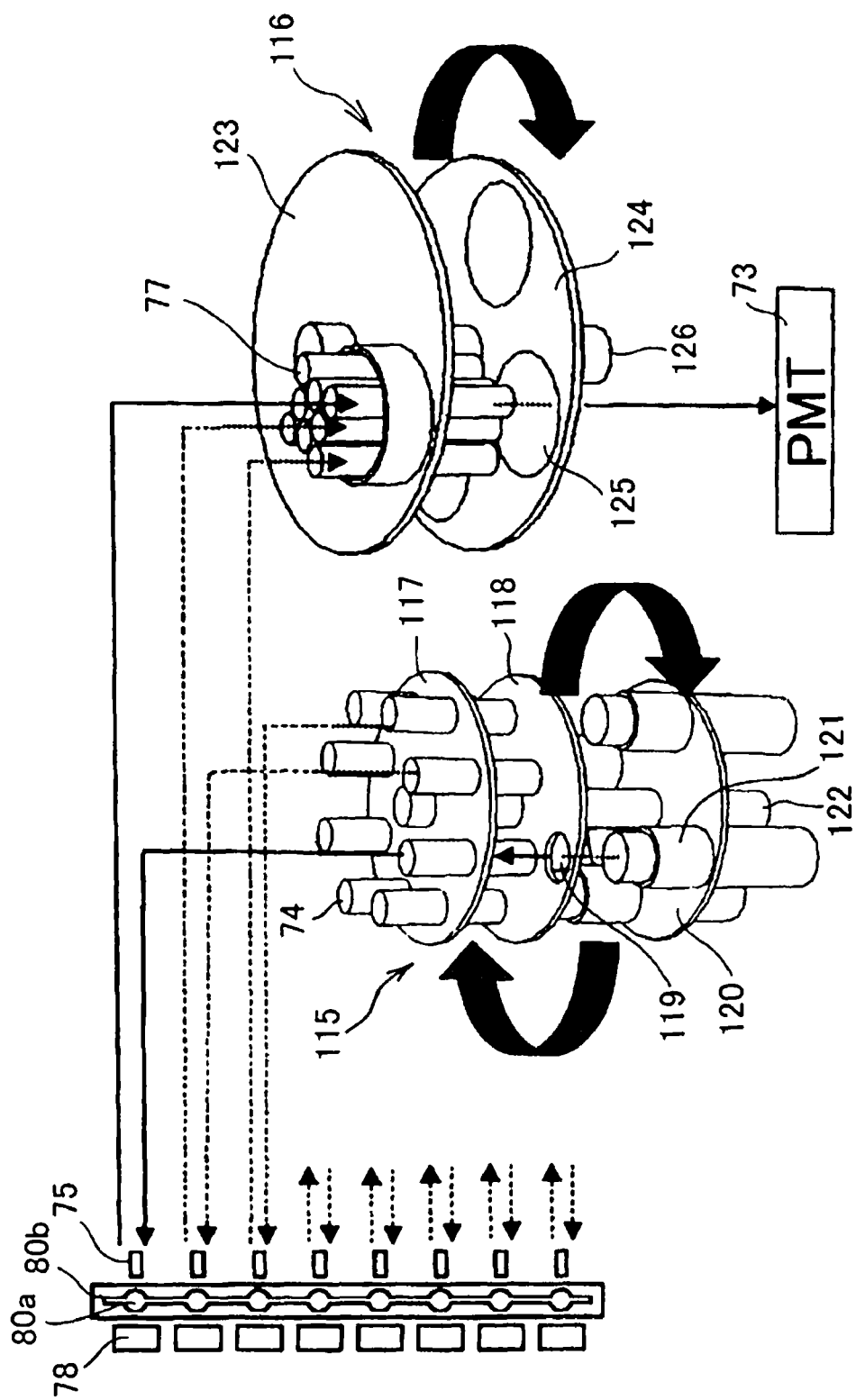
[FIG. 17] is a drawing showing an example of a trigger light source and a light receiving section according to another embodiment of the present invention.

FIG. 17 shows the trigger light source 115 and light receiving section 116 according to another embodiment.

The trigger light source 115 comprises; a supporting plate 117 that supports the eight optical fibers 74 which extend to the rod lenses 75 that are the irradiation end sections of the eight reaction sections 14, such that they are arranged at equal space intervals, a rotating plate 118 in which a hole 119 with an area corresponding to the diameter of the optical fibers 74 has been pierced on the circumference corresponding to the arrangement positions of the optical fibers 74 of the supporting plate 117, a supporting plate 120 that is rotatably provided independently of the rotating plate 118 and on which optical fibers 121 from a plurality of types (four types in this example) of light sources are arranged at equal space intervals, and a shaft 122 that unrotatably supports the supporting plate 117 and rotatably supports the rotating plate 118. Hence the trigger light source 115 has a light source irradiation position selection section.

Furthermore, the light receiving section 116 comprises; a supporting plate 123 that supports the eight optical fibers 77 that extend from the light reception end sections 76 of the eight reaction chambers 15 as a bundle, and a shaft 126 that rotatably supports the four types of optical filters 125 by piercing a plurality (four in this example) of holes in a rotating plate 124 having positions and sizes corresponding to the bundles of optical fibers 77 of the supporting plate 123. Accordingly, the light receiving section 116 has an optical filter selection section.

According to the optical information measuring section of the present embodiment, the excitation light for fluorescence generation from the four types of light sources, by intermittently rotating the rotating plate 118 by one revolution, passes through the hole 119 provided in the rotating plate 118, and the excitation light is introduced to the reaction chambers 15 of the eight reaction vessels 11 through the optical fibers. Then, the fluorescence that has been excited in the reaction chambers that have been irradiated with the excitation light is introduced to the light receiving section 116 via the optical fiber 77. By sequentially rotating the rotating plate 124 during the time the excitation from a single reaction chamber 15 is sustained, it is sequentially passed through four types of optical filters 125, and it is introduced into a photomultiplier 73.

Figure 18:
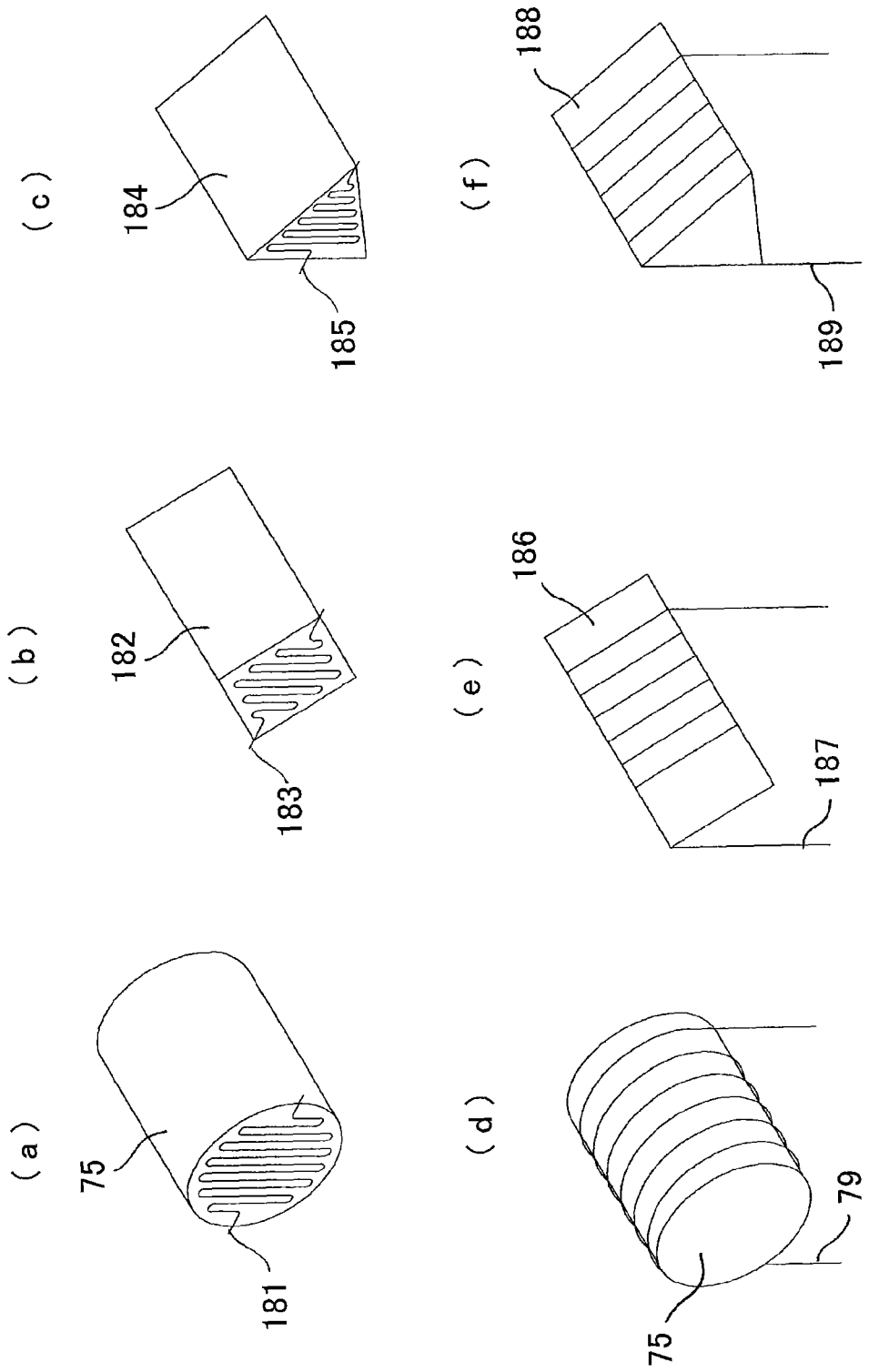
[FIG. 18] is a drawing showing an example of a rod lens according to an embodiment of the present invention.

FIG. 18 shows an example of a rod lens, which is the irradiation end section.

Returning again to FIG. 13, the reaction measuring area 52 has a liquid introducing section 200 provided with eight vessel storing sections 204, which correspond to the rotating bodies which store and rotate the reaction vessels 11. The liquid introducing section 200 comprises a chassis 201 in which the eight vessel storing sections 204 are stored, a hole section 202 for storing the reaction vessel 11 that is to be rotated in the vessel storing section, which is pierced through the upper portion of the chassis 201, and a slit section 203 for easily storing the protruding portions, such as the reaction sections 14 of the reaction vessels 11.

Figure 19:
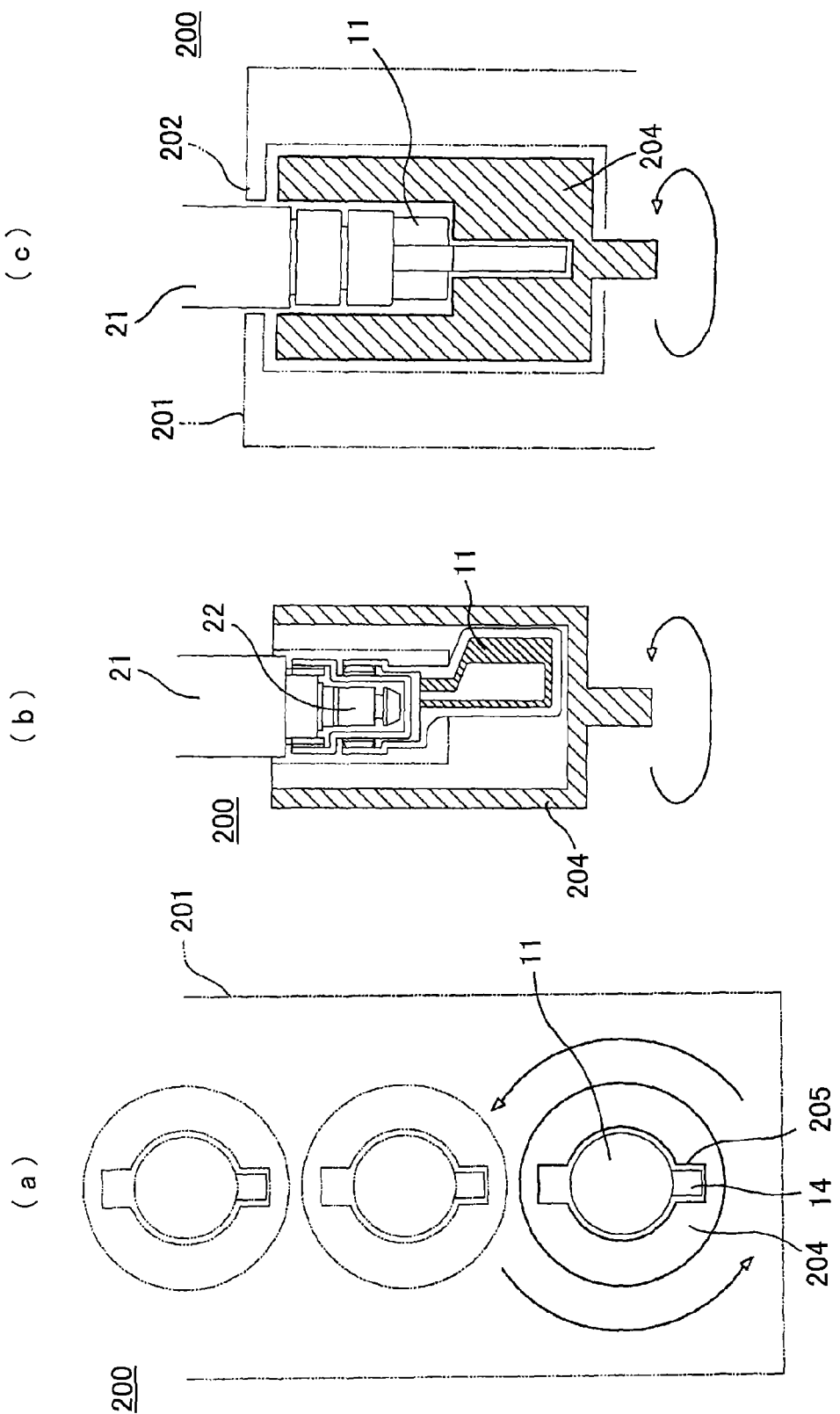
[FIG. 19] is a drawing showing a rotation mechanism according to an embodiment of the present invention.

FIG. 19(a) shows a plan view of the eight vessel storing sections 204 that are provided within the chassis 201. A concave section 205 is provided in the vessel storing section 204, which is the portion into which the reaction section 14 of the reaction vessel 11 that is to be stored is inserted.

FIG. 19(b) shows a front cross-sectional view of the vessel storing section 204 in which the schematically shown reaction vessel 11 has been stored. FIG. 19(c) shows a cross-sectional side view of the chassis 201 of the liquid introducing section 200, and the vessel storing section 204 that has been provided therein.

The vessel storing section 204 is rotated in a state storing the reaction vessel 11. The rotation axis of the vessel storing section 204 is provided such that it passes through the stored vessel. According to the present embodiment, since the liquid introducing section 200 is provided in addition to the liquid introducing device 50, processing can be performed with a good efficiency.

Figure 20:
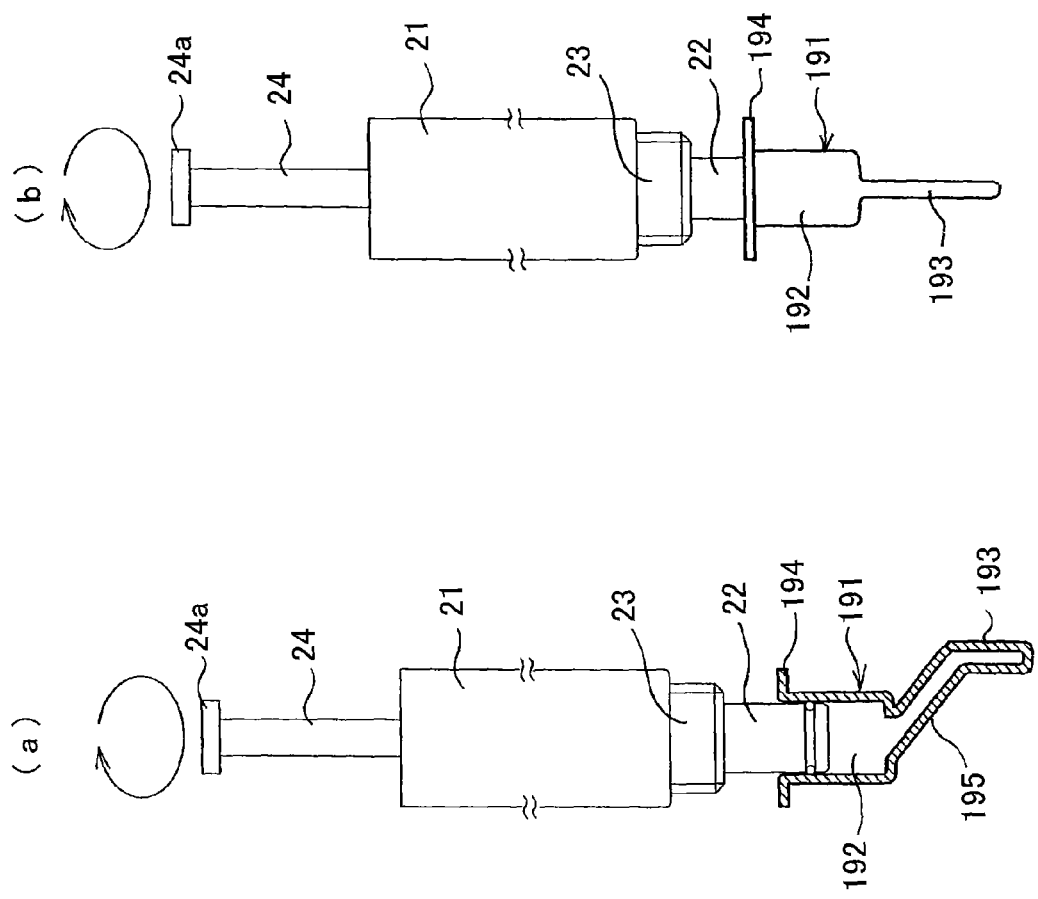
[FIG. 20] is a drawing showing a reaction vessel according to a tenth embodiment of the present invention.

FIG. 20 is an example of a reaction vessel 191 according to a tenth embodiment for capillarating the liquid instead of thinning the liquid. The reaction vessel 191 comprises a storage chamber 192 that has an opening part, in which a liquid is storable, and a reaction chamber 193 that is formed narrower than the storage chamber 192. The opening part of the reaction vessel 191 is formed connectable to the lower end section of the nozzle 22 provided to the exterior, which is a liquid introducing section, and by connecting to the nozzle 22, liquid is introducible into the reaction chamber 193. Here, reference symbol 194 denotes a flange for making it detachable by means of the tip removal plate 23a, and reference symbol 195 denotes a flow passage.

FIG. 21 shows the dynamic PCR unit 90 and the reaction vessel 221, which receives processing at the PCR unit 90.

The PCR unit 90 is, as mentioned above, provided with two movable walls 90a and 90b, which are formed by adiabatic bodies, such that they sandwich the eight movement routes, through which the eight reaction vessels 221 move, from both sides. The vertical direction movement of the reaction vessel 221 is driven by the motor 58 mentioned above, in a state where it is installed on the nozzle 22. The movement route direction is the vertical direction. The PCR unit 90 comprises, as shown in FIG. 13, eight pairs of region groups that are arranged in the horizontal direction, and a single region group comprises, as shown in FIG. 21(a), four regions 91, 92, 93 and 94 that are arranged in the vertical direction. The regions 91, 92, 93 and 94 are arranged within the reaction vessel 221 and in a position through which the portion of the thin layer reaction chamber 225 passes. The cylindrical portion that includes the nozzle 22 of the reaction vessel 221 is formed such that it passes through the space between adjacent region groups.

Furthermore, the region 94 is transparently formed, and at the region 94 provided on one of the movable walls 90a thereof, a fiber end 95 that corresponds to an irradiation end section that irradiates the light from the trigger light source 71 is provided, and at the region 94 provided on the other movable wall 90b, a light reception end section 78 is provided. At that time, the optical axis of the fiber end 95 and the optical axis of the light reception end section 78 are provided such that they are inclined at a predetermined angle. Alternatively, in regard to the irradiation end section and the light reception end section, by providing fiber rod glass 95a and 78a to either or both thereof, and by deviating the irradiation direction and the light reception direction of the light thereof by a predetermined angle, the effect of the light from the irradiation end section towards the light reception end section can be reduced.

Furthermore, in regard to the region 91 to the region 93, in response to the temperature control of PCR processing, for example, a heating end section that achieves a constant temperature of 94° C. is provided for the region 91, and a heating end section that can raise or lower the temperature in a range, for example, from 50° C. to 60° C. is provided for the region 92, and a temperature that meets the processing content is set. Furthermore, in regard to the region 93, a heating end section that achieves a constant temperature of 72° C. is provided. Moreover, the time for the reaction chamber 225 to pass through a single cycle from the region 91 to the region 94 is, for example, approximately 15 seconds, and it is made to repeat the movement a plurality of times.

Figure 22:
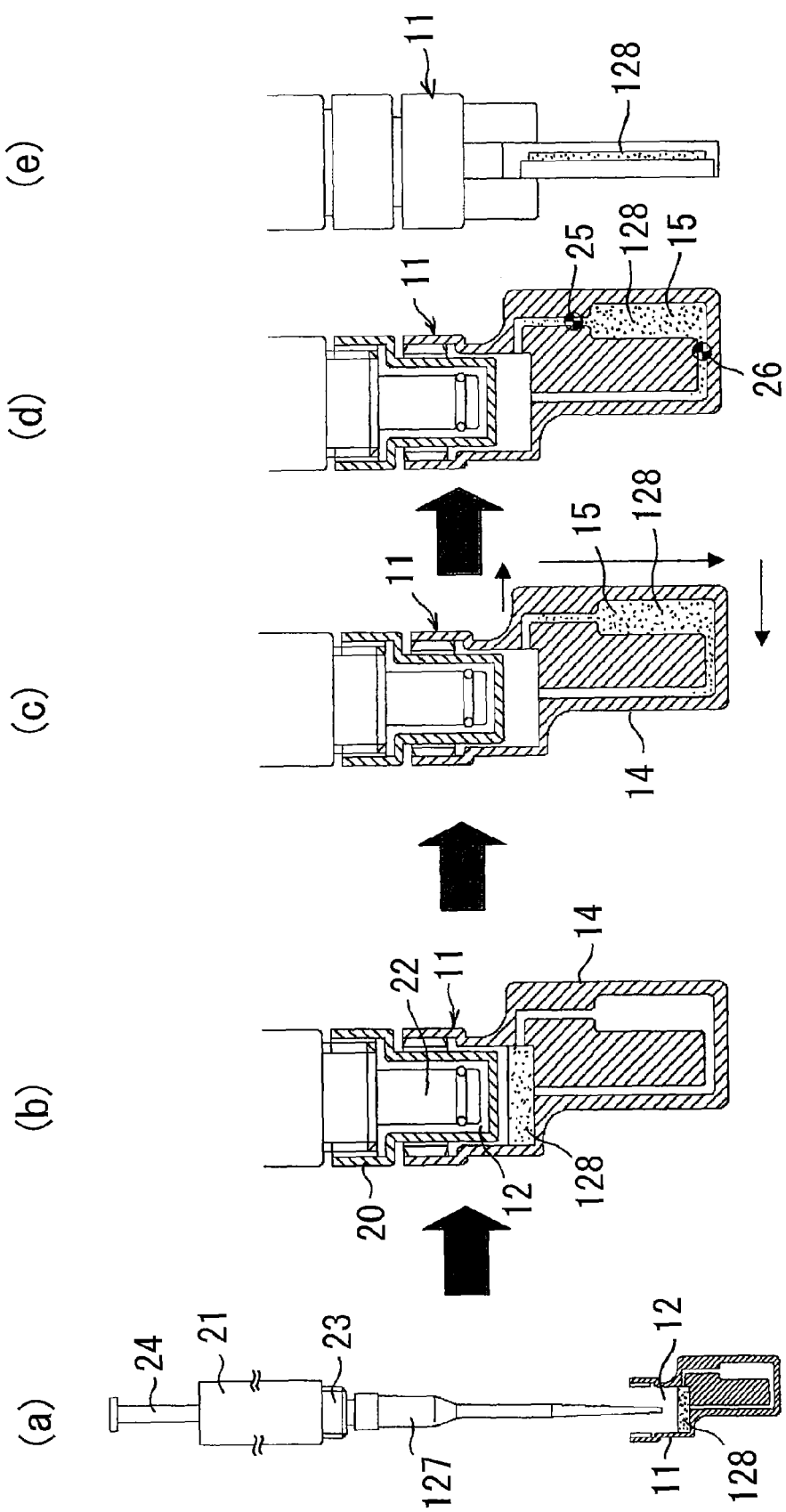
[FIG. 22] is a process flow diagram according to an embodiment of the present invention.

Next, the process flow using the reaction measurement processing system 10 explained above is explained based on FIG. 13 and FIG. 22, which shows the process flow conceptually.

Here, a case in which measurement is performed by using the real time PCR method to measure the quantity of DNA contained in a fixed specimen is explained. Real time PCR is a method for measuring the concentration of nucleic acids by using a nucleic acid probe. The method thereof utilizes, for example, a phenomenon wherein at the time the nucleic acid probe that has been labeled with a fluorescent dye hybridizes into the target nucleic acid, the light emission of the fluorescent dye decreases by a level that depends on the type and base sequence of the base to which the fluorescent dye has bonded, or a phenomenon wherein the light emission strength increases as a result of removing the nucleic acid probe from the target nucleic acid (light emission and light extinction phenomena), or utilizes a method in which a test reagent that emits fluorescent light as a result of the insertion of double-stranded DNA, is added to the reaction system, then a method of detecting the fluorescent light accompanying amplification is utilized, and the determination is performed by detecting the fluorescent light strength thereof (the intercalator method).

In the cartridge vessel 62 of the reaction measurement processing system 10, eight specimens comprising suspensions in which biological tissue, such as skin that has been obtained from patients or the like is suspended, are stored in advance. Furthermore, in the wells 69 and the cartridge vessels 70, for example, test reagents necessary for PCR, DNA polymerase, reaction buffer liquids, fluorescent test reagents, primers, other test reagents thereof, and the like, are stored in advance. The nozzles 22 of the liquid introducing device 50 are, by means of a raising and lowering mechanism not shown in the drawing, simultaneously connected by engagement to the eight dispensing tips that are retained by a tip rack not shown in the drawing as a result of being depressed with respect to the eight dispensing tips. Then by simultaneously repeating the suction and discharging in regard to the sample stored in the cartridge vessels 62, the biological tissue, which is a solid contained in the suspension, is crushed or homogenized to the cellular level thereof. Next, the liquid introducing device 50 is moved in a state where the suspension is suctioned into the dispensing tips, to the location at which the eight filter built-in vessels 161 are stored, that is to say, moved to the position of the third row from the left in the drawing of the matrix form vessel 65, and the suspensions stored in the dispensing tips are discharged into the storage chambers 162 of the eight filter built-in vessels 161.

Connection is performed by inserting the lower end sections of the nozzles 22 into the opening parts of the storage chambers 162. In this state, the filter built-in vessels 161 are lifted to the upper side of the matrix form vessel 65, and the filter built-in vessels 161 are simultaneously rotated together with the nozzles 22 by simultaneously rotating the eight nozzles 22. Then, the homogenized suspensions stored in the storage chambers 162 of the filter built-in vessels 161 move from the storage chambers 162, pass through the filters 100 within the filter chambers 164, to the housing chambers 166, by means of centrifugal force resulting from rotation. As a result of the filters 100, the impurities are captured, and solutions without impurities that contain the target DNA can be obtained in the housing chambers 166. The housing chambers 166 are detached from the filter chambers 164 of the filter built-in vessels 161, the dispensing tips are connected, the solution is suctioned, and it is transported and discharged in a predetermined well 69 of the cartridge vessel 70 in which the necessary test reagents, for example, a probe that has been labeled with a fluorescent material. and the like, is stored, and a solution that is mixed with the necessary test reagents is produced.

Next, the eight nozzles 22 are moved to the tip rack (not shown in the drawing) by moving the nozzle heads of the liquid introducing device 50, and by operating the raising and lowering mechanism of the nozzles 22, the nozzles 22 are connected by inserting into and engaging the eight unused dispensing tips 127 stored in the tip rack. Next, the dispensing tips 127 are moved to the eight wells 69, and the solutions 128 stored within the wells 69 are simultaneously suctioned into the unused eight dispensing tips 127. Then, as conceptually shown in FIG. 22(a), they are transported to the eight reaction vessels 11 that are retained by the holding rack 70a, and the solutions 128 are discharged into the storage chambers 12 thereof Following discharging, the eight dispensing tips 127 are removed from the nozzles 22 of the liquid introducing device 50 by the tip removal plate 23a, and are discarded.

Next, the liquid introducing device 50 is moved to the position of the holding rack 70a in which the eight caps 20 are stored, the nozzles 22 are simultaneously inserted into the eight caps 20, and by rotating the nozzles 22, the eight caps 20 are connected to the threaded sections 23.

Next, as shown in FIG. 22(b), the nozzle heads of the liquid introducing device 50 are moved to the position at which the reaction vessels 11 of the holding rack 70a are retained, the caps 20 installed on the nozzles 22 are inserted within the opening parts 13 and the storage chambers 12 of the reaction vessels 11, in which the solutions have been stored, and as a result of simultaneously rotating the nozzles 22, they are connected by threading the caps 20 and the opening parts 13. Next, following raising of the reaction vessel 11 to the upper side of the retention rack 70a, the nozzle 22, and accordingly the reaction vessel 11 connected to the nozzle 22, are simultaneously rotated at a high speed in the same direction as the rotation for threading at the cap 20 and the opening part 13. In regard to the reaction vessel 11, in a state where it is stored in the retention rack 70a, since the reaction chambers 15 thereof are retained in a state where they are respectively inserted into a slit-shaped space provided in the retention rack 70a, the reaction vessel 11 does not rotate during the rotation of the nozzle 22.

Then, as shown in FIG. 22(c), the solutions 128 stored within the storage chambers 12 move to the reaction chambers 15 by centrifugal force, and are introduced into the reaction chambers 15.

The reaction vessels 11 in which the solutions have been introduced to the reaction chambers 15 are transported to the PCR unit 80 by the liquid introducing device 50 in a state with the caps 20 installed, and they are retained such that they are supported by the hole 80a and the slit 80b portions of the PCR unit 80.

As shown in FIGS. 22(d) and (e), the light reception end section 78 is brought close to the reaction chambers 15 by the opening and closing mechanism 81, and inside of the reaction chambers 15 are simultaneously made a sealed state by pushing the protrusion sections 101 and 102 against the corresponding closing positions 25 and 26, and deforming blocking positions, that is to say, the elastic valves 16a and the plates 18.

Next, not only the light reception end section 78, but the rod lens 75 in which the heating body 79, which corresponds to the heating and cooling end section, is wrapped around, is simultaneously brought close to, or in contact with, the reaction chambers 15 from the back side of the reaction section 14 by the opening and closing mechanism 81, and temperature control is performed based on the PCR method. At that time, in the present embodiment, since the rod lens 75, to which the heating body 79 has been wrapped around, is directly brought close to, or into contact with, the reaction chambers 15, it becomes possible to supply a vessel for PCR with faithful responsiveness with respect to temperature changes.

In this PCR amplification process, for example, as shown in FIG. 16, in regard to the trigger light source 71 serving as the light for excitation that excites the fluorescent material which is the labeled material used in the reaction chambers 15, light from the light source of the wavelength selected by the rotating plate 104 is simultaneously irradiated into the reaction chamber 15 through the optical fibers 74 at the rod lenses 75, which are irradiation end sections. At that time, the light receiving sections 72 simultaneously irradiate the eight reaction chambers 15. At that time, at the light receiving sections 72, in regard to the eight reaction chambers 15, the emitted lights received at the light reception end sections 76 at the light reception positions are sequentially selected by the rotating plate 110, and in regard to the intermittent rotation of the rotating plate 110, within the time the received light from a single light reception end section 76 is selected, the rotating plates 112 are sequentially intermittently rotated one rotation, and in a case where the corresponding optical filter 113 is selected, data regarding the light input into the PMT 73 is obtained. The operations above, in regard to all four types of light wavelengths, measure by converting the light received from all the reaction chambers 15 into an electrical signal. As a result, the state of the light emission strength of the fluorescent material is measured in real time, and the quantity of DNA that is the subject thereof, can be measured.

Furthermore, in a case where the reaction chamber 15 is cooled by separating the rod lens 75, which is wrapped around the heating body 79, from the reaction chamber 15. Then as well as separating the rod lens 75, by simultaneously subjecting the reaction vessels 11 to cold air by means of a fan 80c, heat can be efficiently released from the reaction chamber 15.

According to the present embodiment, it is possible to homogenize the suspension containing the specimen, extract a solution containing the target DNA from the homogenized suspension, thin the solution to which all test reagent types have been mixed with the DNA, and efficiently and consistently automatically perform the operations until the optical information is obtained, while performing accurate and highly responsive temperature controls of the thinned solution, in a compact device.

In the above explanation, in regard to the liquid introducing device 50, as the liquid introducing section, although the liquid stored in the storage chamber was introduced to the reaction chamber by connecting the reaction vessel to the nozzle 22 serving as a rotating body, it is in no way restricted to this, and as the liquid introducing section, it is acceptable if the reaction vessel 11 is connected to the nozzle of the liquid introducing device 50 within the vessel storage section 204 of the liquid introducing section 200, the reaction vessel 11 is stored within the vessel storage sections 204 of the liquid introducing section 200, and the introduction is performed by rotation. In particular, in regard to the production of the liquid that is stored within the reaction vessel, the movement of the liquid introducing device 50 is simplified by using the liquid introducing section 200.

As the reaction vessel, it is acceptable that by connecting the tip-shaped reaction vessel 41 to the nozzle 22 of the liquid introducing device 50 via the cap 42, the liquid is introduced into the gap section 41a serving as the reaction chamber, not as a rotating body, but by using the suction and discharging function of the nozzle 22.

In this case, in regard to the liquid introduced into the gap section 41a, following sealing of the gap section 41a and following reaction, as a result of opening the hole section 42f by moving the cap engaging sections 47a and 47b in the somewhat upper direction with respect to the tip removal plate 23a, the nozzle 22 and the gap section 41a is communicated, the sealed state is released, and by discharging with respect to the nozzle 22 through the thin diameter section 46, the product can be collected.

The embodiments above have been specifically explained in order to better understand the present invention, and do not restrict other embodiments in any way. Accordingly, they are changeable within a scope that does not depart from the gist of the invention. For example, in regard to the optical information measuring device, it is acceptable for optical systems such as a half mirror, a mirror, or an optical filter, to be used to distribute the light, rather than selecting the light by temporal switching as mentioned above.

Furthermore, the various mechanisms are not restricted in any way to those mentioned above, and, for example, as a rotation mechanism of the nozzles, it is possible to use a gear mechanism instead of a belt mechanism Furthermore, for example, it is possible to use the rotation mechanism achieved by the present inventor that has been disclosed in PCT/JP02/01147 (WO02/063300 A1).

The shape of the reaction vessels is not restricted to that explained above, and it is acceptable if they are not cylindrical, but are a prismatic shape or a spherical shape. Furthermore, although an example is described where they are connected to the nozzles via the cap, it is acceptable if they are directly connected to the nozzles without including the cap. In regard to the rotation mechanism and the suction and discharge mechanism of the nozzles of the liquid rotating treatment device 50, the number of nozzles, and the number of the various vessels, they are not restricted by the above explanation in any way. Cases where the number of nozzles and vessels is one, or a number other than eight, are acceptable. Furthermore, although the filter was used to remove the impurities within the suspension, it may be used to capture the target material.

In regard to the rotation supporting axle, not only a case where it is provided along the axis of the opening part 13 of the storage chamber 12 as shown in FIG. 5 is possible, but it acceptable for it to be provided such that it is parallel to the axis of the opening part 13. Since this rotation supporting axle is a portion of the vessel, the rotation of the vessel of this case about the rotation supporting axle corresponds to rotation of the vessel about its own axis.

Furthermore, although the explanation above used the optical information measuring section of FIG. 16, it is acceptable to use the optical information measuring section of FIG. 17. Moreover, although the heating and cooling section was provided on both sides of the reaction chamber, it is acceptable to provide it on only one side. Furthermore, it is acceptable for the heating and cooling section to involve a liquid or a gas, rather than a solid. Moreover, in the explanation above, although embodiments regarding the thinning of a liquid were mainly given, capillaration of a liquid can also be performed.

Furthermore, in the explanation above, in FIG. 13, although both a static PCR unit and a dynamic PCR unit have been provided and switchingly used, it is acceptable if only one of the PCR units are provided.

Moreover, components such as the reaction vessels, the storage chambers, the reaction chambers, the flow passages, the reaction sections, the rotating body supporting axles, the dispensing tips, the light measuring sections, the caps, all vessel types, the test reagents, the rod form members, the nozzles, and the heating and cooling sections, and the liquid introducing section, and all mechanism types mentioned above can be arbitrarily combined while appropriately modifying them.

INDUSTRIAL APPLICABILITY

This relates to the reaction vessel, the reaction measuring device, and the liquid rotating treatment device according to the present invention. The present invention is, for example, related to fields in which processing, testing, and analysis related to genes principally in regard to, for example, DNA, RNA, mRNA, rRNA, tRNA, and plasmids, is required, and is related to all fields, for example, industrial fields, agricultural fields such as food products, agricultural products, and seafood processing, health care fields such as drug fields, sanitation, health, disease, and genetics, and scientific fields such as biochemistry or biology. The present invention can particularly be used in various DNA-handling analysis and tests, such as PCR, and real time PCR.

BRIEF DESCRIPTION OF THE REFERENCE SYMBOLS

10 Reaction measurement processing system
11, 11a, 31, 41, 131, 141, 151, 191, 211, 221 Reaction vessel
12, 32, 66, 132, 142, 152, 212, 222 Storage chamber
14, 14d, 134, 144, 154, 214, 224 Reaction section
15, 135, 145, 155, 215, 225 Reaction chamber
18 Film
20 Cap
22 Nozzle (rotating body)
16, 133, 143, 153, 212, 223 Liquid introduction flow passage
17, 137, 147, 217, 227 Discharge flow passage
16a Elastic valve (blocking position)
17b Hole section (blocking position)
138, 136, 148, 146, 156, 213, 216, 226, 228 Blocking position
41a Gap section (reaction chamber)
50 Liquid introducing device
51 Liquid treatment area
52 Reaction measuring area
71 Trigger light source
72 Light receiving section
73 PMT (photomultiplier)
75 Rod lens (irradiation end section)
76, 78 Light reception end section
79 Heating body (heating and cooling section)
200 Liquid introducing section

The invention claimed is:

1. A reaction vessel being a vessel that has:
   a storage chamber in which a liquid is storable, that has an opening part, said opening part defining a first axis passing therethrough;
   a reaction chamber that is formed thinner or narrower than said storage chamber, and wherein at least a portion of said reaction chamber has a translucence or a semi-translucence; and
   at least one flow passage that communicates between said storage chamber or the exterior and said reaction chamber,
   wherein the liquid can be introduced into the storage chamber via said opening part or said flow passage,
   wherein, when the liquid is introduced into the storage chamber via said opening part, the liquid passes through said opening part in a first direction that is parallel to the first axis,
   wherein said storage chamber extends from the first axis in a second direction that is perpendicular to the first axis,
   wherein said reaction chamber is spaced from the first axis in the second direction so that said reaction chamber is positioned farther away from the first axis than said storage chamber,
   wherein said vessel is formed such that it is connectable to a rotatable rotating body, the rotatable rotating body defining a second axis and serving as a liquid introducing section provided externally, and
   wherein, when said vessel is connected to said rotatable rotating body, the first and second rotation axes coincide, and said reaction chamber is rotatable together with said rotating body about the coinciding first and second rotation axes.

2. A reaction vessel according to claim 1, wherein said opening part has a cap that is connectable to said opening part such that it is detachable.

3. A reaction vessel according to claim 1, wherein said flow passage and said reaction chamber are formed by a tabular frame having grooves or holes, and a film of a soft material that covers said frame from one side or from both sides.

4. A reaction vessel according to claim 1, wherein said rotating body is a rotatable nozzle in which suction and discharge of gas is possible, and said nozzle has a rotation axis along an axial direction thereof.

5. A reaction vessel according to claim 1, wherein said reaction chamber is formed in an approximate cylindrical shape.

6. A liquid introducing and reaction measuring method comprising the steps of:
   storing a liquid which becomes a processing subject, in a storage chamber of a reaction vessel according to claim 1;
   introducing said liquid from said storage chamber to the reaction chamber of said reaction vessel;
   sealing said liquid in the reaction chamber by blocking an opening provided in said reaction chamber, or a flow passage;
   performing heating and cooling of the liquid sealed in said reaction chamber; and
   measuring optical information from said reaction chamber.

7. A reaction vessel according to claim 1, wherein; said flow passage comprises a liquid introduction flow passage for introducing the liquid from said storage chamber to the reaction chamber, and a discharge flow passage for discharging gas from said reaction chamber.

8. A reaction vessel according to claim 7, comprising, at the time where said reaction vessel is connected to said rotating body, a rotation supporting axle along said second axis of said rotating body.

9. A reaction vessel according to claim 7, wherein said opening part is, in a state where the second axis of said rotating body is passed therethrough, connectable such that it is detachable by means of a lower end section of said rotating body or a detachable cap that is detachable on the lower end section of said rotating body.

10. A reaction vessel according to claim 7, wherein said rotating body is a nozzle in which suction and discharging of gas is possible, and said nozzle has a rotation axis in an axial direction thereof, or parallel to the same.

11. A reaction vessel according to claim 7, wherein a deformable soft material is provided for at least a portion of said flow passage or said reaction chamber, and said reaction chamber is sealable by deforming said soft material.

12. A reaction vessel according to claim 11, wherein said soft material is an elastic block material that is deformable by means of a pressing force, and the interior has a void through which passage of liquid and gas is possible.

* * * * *